United States Patent [19]

Cobb

[11] Patent Number: 4,893,286

[45] Date of Patent: Jan. 9, 1990

[54] SYSTEM AND METHOD FOR PREPROCESSING AND TRANSMITTING ECHO WAVEFORM INFORMATION

[75] Inventor: Wesley N. Cobb, University Heights, Ohio

[73] Assignee: Standard Oil Company, Cleveland, Ohio

[21] Appl. No.: 116,309

[22] Filed: Nov. 4, 1987

[51] Int. Cl.$^4$ ............................................. G01S 15/02
[52] U.S. Cl. ...................................... 367/87; 367/99; 367/35; 181/105; 73/598
[58] Field of Search ............... 367/99, 87, 35, 81–85; 340/853–859; 181/105; 73/592, 598, 600; 381/29, 34, 35, 106

[56] References Cited

U.S. PATENT DOCUMENTS

| | | |
|---|---|---|
| 3,369,626 | 2/1968 | Zemanaek, Jr. . |
| 3,407,650 | 10/1968 | Dickinson, III . |
| 3,503,038 | 3/1970 | Baldwin . |
| 3,518,679 | 6/1970 | Baldwin et al. . |
| 3,754,472 | 8/1973 | Dory . |
| 3,815,124 | 6/1974 | Brewer .......................... 381/31 X |
| 3,944,942 | 3/1976 | Chudleigh, Jr. .................. 330/86 |
| 3,961,683 | 6/1976 | Delignieres . |
| 3,996,791 | 12/1976 | Niklas et al. . |
| 4,027,281 | 5/1977 | Greve et al. . |
| 4,219,810 | 8/1980 | Joosten ............................. 340/853 |
| 4,254,479 | 3/1981 | Wiley ............................... 367/35 |
| 4,255,798 | 3/1981 | Havira ............................. 367/35 |
| 4,274,288 | 6/1981 | Tittmann et al. ................. 73/602 |
| 4,290,308 | 9/1981 | Dau .................................. 73/602 |
| 4,340,944 | 7/1982 | Dory ............................... 367/96 |
| 4,385,255 | 5/1983 | Yamaguchi et al. ............ 310/335 |
| 4,389,893 | 6/1983 | Ophir et al. .................... 73/600 X |
| 4,399,704 | 8/1983 | Gardineer et al. ................ 73/642 |
| 4,409,838 | 10/1983 | Schomberg . |
| 4,412,315 | 10/1983 | Flournoy .......................... 367/99 |
| 4,415,895 | 11/1983 | Flagg . |
| 4,428,235 | 1/1984 | Sugiyama . |
| 4,428,237 | 1/1984 | Zeger et al. ...................... 73/592 |
| 4,435,985 | 3/1984 | Wickramasinghe ............... 73/642 |
| 4,552,020 | 11/1985 | Auphan ............................ 73/602 |
| 4,586,380 | 5/1986 | Patterson ......................... 73/623 |
| 4,587,641 | 5/1986 | DiFoggio ......................... 367/30 |
| 4,591,983 | 5/1986 | Bennett et al. ................... 364/403 |
| 4,641,529 | 2/1987 | Lorenzi et al. ................... 73/601 |
| 4,670,848 | 6/1987 | Schramm ......................... 364/513 |
| 4,698,793 | 10/1987 | Wu .................................. 367/32 |
| 4,741,018 | 4/1988 | Potratz et al. .................. 381/106 X |
| 4,744,030 | 5/1988 | Carlson et al. .................... 367/35 |

FOREIGN PATENT DOCUMENTS

| | | |
|---|---|---|
| 0075997 | 4/1983 | European Pat. Off. . |
| 2160375 | 6/1973 | Fed. Rep. of Germany . |
| 1302889 | 7/1962 | France . |
| 1595825 | 7/1970 | France . |
| 2172400 | 9/1986 | United Kingdom ............ 181/105 |

OTHER PUBLICATIONS

Benoit Froelich et al., "Cement Evaluation Tool—a New Approach to Cement Evaluation", SPE 10207, 1981.

Alain Dumont et al., "A Single Tool for Corrosion and Cement Evaluation", Society of Petroleum Engineers of AIME, SPE 13140, 1984.

(List continued on next page.)

Primary Examiner—Thomas H. Tarcza
Assistant Examiner—Daniel T. Pihulic
Attorney, Agent, or Firm—Saidman, Sterne, Kessler & Goldstein

[57] ABSTRACT

In the field of the echography, the present invention is a system and method of preprocessing and transmitting information (such as echo waveform information) from a source (such as a transducer) to a destination (such as a rule-based computer system). The present invention reduces the absolute amount of information that is transmitted without reducing the amount of meaningful information that is conveyed. In this way, the present invention is effectively able to transmit more meaningful information than would be expected for conventional transmission systems. It also acts to reduce the amount of information processing that must be done at the destination.

14 Claims, 18 Drawing Sheets

OTHER PUBLICATIONS

C. C. Carson & T. Bauman, "Use of an Acoustic Borehole Televiewer to Investigate Casing Corrosion in Geothermal Wells", *Corrosion* 86, Mar. 17–21, 1986, Pr. 408.

Maksym et al., "Machine Analysis of Acoustical Signals", *Pattern Recognition*, vol. 16, No. 6, pp. 615–625 (1983).

H. Penny Nii, "Blackboard Systems", The Blackboard Model of Problem Solving and the Evolution of Blackboard Architectures, *The AI Magazine*, Part One, pp. 38–53 (1986).

H. Penny Nii, "Blackboard Systems, Blackboard Application Systems, Blackboard Systems from a Knowledge Engineering Perspective", *The AI Magazine*, Part Two, pp. 82–106 (1986).

SYSTEM AND METHOD FOR PREPROCESSING AND TRANSMITTING ECHO WAVEFORM INFORMATION

CONTENTS

BACKGROUND OF THE INVENTION
1. Field of the Invention
2. Related Art
   a. The Corrosion Problem
   b. Known Detection and Analysis
      i. The Kinley Caliper
      ii. Ultrasonics
         A. The BHTV
         B. Pulse Echo Resolutions
         C. Full Echo Waveforms
         D. Frequency Domain vs. Domain Analysis
SUMMARY OF THE INVENTION
BRIEF DESCRIPTION OF THE DRAWINGS
DETAILED DESCRIPTION OF THE PREFERRED EM
1. Generation of Full Echo Waveform
   a. Curved Transducer
   b. Coverage of the Target Surface
   c. Bandwidth Reduction
   d. Full Echo Waveforms
      i. A Simple Example
      ii. Actual Example
2. Principles of Analysis of Full Echo Waveform
   a. Pit Depth
   b. Pit Area
3. Transmission of Full Echo Waveform Information
4. Rule-Based Analysis of Full Echo Waveform
   a. Terminology
   b. General Introduction to Artificial Intelligence
   c. Overall Software Flow
      i. Echo Feature Extraction
      ii. Initialization and
      iii. Firing of Rules in Base
      iv. Output of Corrosion User Interface
   d. Structure of the Knowledge Base
      i. The Control Function
      ii. MULTIPLE KS
      iii. ECHOS KS
         a. Dominant Echo Identification (E1)
         b. Identification of Echo Other than an Identified Multiplied Structure (E2)
         c. Identification Echos in the Absence of Identified Multiplied Structures (E3)
      iv. ULTRASONICS KS
   e. Processing Example
APPENDIX
CONCLUSION
CLAIMS

BACKGROUND OF THE INVENTION

1. Field of the Invention

This invention relates to and methods for detecting and analyzing surface imperfections using ultrasonic techniques. More specifically, the invention relates to measurement of corrosion pits on the surfaces of metal tubulars within the boreholes of oil wells and subsequent analysis of ultrasonic echos using a rule-based artificial intelligence technique.

2. Related Art a. The Corrosion Problem

Corrosion in oil well tubulars has long been a source of difficulties for the oil production industry. In a typical oil well, the metallic tubular is disposed within a casing. The interior of this metal tubular passes crude oil from a subterranean formation to the surface. Often, these formations contain three layers. The top layer is a "gas cap" which is situated above a layer of oil, which is in turn situated above a layer of water at the bottom of the formation. Typically, the oil is expelled to the surface by the naturally available pressure of the "gas cap." The production of oil may be artificially enhanced during "artificial lift" by pumping gas down the exterior of the tubular within the casing to replenish the gas cap.

Corrosion pits can grow to eat through the side of the tubular so that the seal between the oil in the interior of the tubular and the gas exterior to the tubular is broken. Gas penetrates into the oil passageway instead of going to the "gas cap." The escaping gas (or fluids within the casing) frustrate the replenishment of the gas cap. Depending on the severity of the corrosion-caused hole in the tubular, the ability of the pumping mechanism to pump oil from beneath the earth is diminished or even prevented.

When a corrosion pit has eaten completely through a tubular, it was once necessary to replace the tubular. This was obviously a very expensive process, considering both the direct cost of the replacement as well as the lost revenues due to "downtime" of the oil well. Chemical treatment methods were then developed to inhibit the further progress of existing corrosion pits. Although chemical treatments proved less expensive than the actual replacement of a downhole tubular, significant costs were still incurred from the application of the chemical process itself, in addition to the lost revenues due to downtime of the oil well.

Therefore, even given the ability to prevent and repair corrosion pits before they become fatal to the operation of the oil well, it is crucial from a cost standpoint that the chemical treatment be applied only in circumstances when such chemical application is necessary, so as to prevent needless downtime of the oil well.

b. Known Detection and Analysis Methods

There are various known devices which attempt to monitor the condition of the interior of oil well tubulars.

i. The Kinley Caliper

A first known device, commonly known as the Kinley Caliper, is a device which is drawn up the interior of the tubular. The Kinley Caliper comprises a plurality (usually less than 48) of wire probes which extend radially from the caliper device to contact the inner walls of the tubular. Springs provide outward force on these wire probes to maintain their contact with the tubular face as the device is drawn up the tubular. As a corrosion pit is encountered by one or more of the wire probes, the spring which urges the probe(s) outward causes displacement of the probe(s). A quantitative measurement of the displacement of these probe(s) is made in the device, and this displacement measurement is internally recorded on a metal drum.

The Kinley Caliper had the disadvantages that, as the probes were drawn along the borehole's interior, the probes' outward pressure caused scratches on the tubular surface. Also, depending on the draw rate and spring strength, the wire probes had a tendency to "skip over" smaller corrosion pits or give misleadingly shallow indications of deeper corrosion pits. Finally, the effective coverage of the probes was limited, in the sense that the surface area of the tubular which happened to fall between the probes was not tested for corrosion pits.

ii. Ultrasonics

Advances in the fields of ultrasonics and microelectronics allowed more thorough, less damaging measurement of corrosion pits, as well as the ability to transmit greater amounts of information uphole in a limited amount of time so as to speed the logging process.

A. The BHTV

An acoustic logging device is disclosed in U.S. Pat. No. 3,503,038 to Baldwin. One embodiment of this device has become known as the Borehole Televiewer (BHTV). The BHTV is a device which is designed to be drawn up the interior of an uncased borehole. The BHTV comprises a rotating transducer which defines a helical pathway as the entire device is drawn up the borehole. Although the BHTV was originally intended for use in detecting fractures in uncased boreholes, the device has been tested for measurement of casing corrosion. [C. Carson and T. Bauman, "Use of an Acoustic Borehole Televiewer to Investigate Casing Corrosion in Geothermal Wells," Paper #408, *Corrosion* 86, Houston, Tex., Mar. 17-21, 1986]. The following description presents an explanation of the ultrasonic operation of the device, as it could be applied to detection of corrosion in tubulars.

B. Pulse Echo Resolution

Referring to FIG. 1, a known transducer 102 having a flat surface 104 is enclosed within a sonde body 106. The sonde 106 is located within a circular tubular 100, a portion of which is indicated in FIG. 1. Transducer 102 is excited by an excitation pulse. The excitation pulse causes an acoustic wave to emanate from transducer surface 104 toward the inner surface 108 of tubular 100 radially along lines 110, 112, and 114. After striking the inner surface 108 of tubular 100, a portion of the acoustic energy is reflected from the tubular (as an "echo") back toward transducer surface 104. This echo is detected by transducer 102. Electronic circuitry within the sonde body 106 converts the echo's acoustic energy into electrical signals indicative of the instantaneous magnitude of the returned acoustic energy for transmission uphole.

It can be seen from FIG. 1 that the path traversed by the portion of the acoustic wave along paths 110 and 112 in its round-trip from transducer surface 104 to the surface 108 of tubular 100 is shorter than the round-trip path traveled by the portion of the acoustic wave traveling along path 114. The difference in path lengths is due to the curvature of the inner surface 108 of tubular 100 which is not matched by the flat surface 104 of transducer 102.

The difference in distance traversed by different portions of the acoustic pulse results in a returned echo which is dispersed in time. The dispersed echo pulse is smaller in magnitude and longer in duration than the original pulse emitted by the transducer. This dispersion results in increased uncertainty as to the distance traversed by the acoustic wave. This increased uncertainty results, first, from the reduced amplitude of the received echo, since an echo of smaller amplitude is inherently more difficult to detect. Second, the increased uncertainty as to the exact time of arrival of the pulse is also caused by the widening of the returned echo.

To those skilled in the art of acoustics, it is well known that the degree of attenuation of an acoustic pulse is proportional to its frequency. (As is known in the art, "pulse" actually denotes a pulse-modulated sinusoid; the "pulse" is actually the envelope determined by the peaks of the modulated sinusoid. It is the frequency of the sinusoid, and not of any pulse train, which is referred to when speaking of "frequency" in this discussion. FIG. 8, described in greater detail below, illustrates pulse-modulated sinusoids 804 of returned echo pulses with their accompanying envelopes 802.) It is also known that, in 15 acoustic echography, a higher degree of resolution can be attained using pulses composed of higher frequency acoustic waves. Therefore, in selecting acoustic frequencies, there has traditionally been a tradeoff between the competing desires for high resolution and for low attenuation.

It is therefore desirable to produce acoustic pulse echos which are large in magnitude and short in duration, and which are capable of improved resolution.

C. Full Echo Waveforms

The rotating transducer emits periodic ultrasonic excitation pulses which impact the tubular surface and cause a series of echos to be returned to the transducer. A "full echo waveform" comprises the set of all echos which are returned from a target surface in response to a single incident excitation pulse. (The process by which a *series* of echos, or "full echo waveform", is formed from a single excitation pulse is described in detail in the discussion of FIG. 9, below.)

The present discussion serves as an exposition of the limitations of known devices which do not utilize the full echo waveform. In the known device described above, only the first of the series of echos was used to determine the distance of the transducer from the tubular surface. The information in the full echo waveform beyond the first echo is not utilized. The distance determination was made by means of a simple multiplication of (1) the known speed of the acoustic pulse (and echo) in the liquid medium within the borehole by (2) the measured one-way travel time of the first-received acoustic pulse.

If the transducer were situated adjacent a corrosion pit larger than the transducer surface, the round-trip travel time, and therefore the measured distance between the transducer and the bottom of the pit, would be larger than would be the case if the transducer were situated above a non-corroded area of tubular.

For this known device, a small pit is detected only if the entire ultrasonic beam enters the pit. In this case, the first echo comes from the bottom of the pit and the increase in arrival time can be used to measure the depth. If, however, *any* portion of the beam intercepts the tubular beyond the edge of the pit, an echo will be generated by the uncorroded inner wall of the pipe. If this echo is large enough to trigger the device's timing circuits, it will be recorded as the first echo, and the pit will go undetected. Since a smooth area of uncorroded inner wall will generate a strong reflected echo, very little of the beam has to intercept the inner wall for a significant echo to be generated. Thus, for this known device, the ultrasonic wave must impact totally within the pit area for pit detection to occur.

Similarly, if the transducer were positioned adjacent a corrosion pit which was smaller in area than the area of the transducer, then (assuming for simplicity that the bottom of the pit is flat) two echo signals would be received by the transducer. The two echo signals would correspond to the two different round-trip travel times of the acoustic pulse in reflecting off the uncorroded tubular surface and the corrosion pit surface. The analysis of only the front-surface echo, even in the presence of an "ideal" (flat) pit, wastes a great deal of information regarding the progress of corrosion. This waste of information is a limitation characteristic of the BHTV, described above.

As will be seen in the discussion of FIG. 10, below, the complexity of the "full echo waveform" occurring after the front surface echo also shows the dispersion effects of the rough surface of real-world corrosion pits. The acoustic energy which falls on a surface which is not flat and perpendicular to the incident acoustic wavefront follows a path which is less predictable.

Referring to FIG. 3, paths of various portions of an acoustic pulse emanating from a transducer are illustrated. Element 102 (also in FIG. 1) designates a transducer according to a known device, whereas element 202 (also in FIG. 2) designates a transducer according to the preferred embodiment of the present invention. Since the following discussion relates to the reflective properties of a corroded tubular 100, the particular transducer chosen has little bearing on this conceptual discussion.

It is common to have the complex pit surfaces reflect the acoustic energy in a way which simply disperses the returning echos over a greater time period so that a single, detectable peak is not formed at all. Path 308 illustrates this occurrence. This complex surface roughness is indicated in a full echo waveform only as a reduction in the amplitude of existing peaks, and a corresponding rise in the "noise floor." This dispersion, of course, makes it more difficult to discriminate returned echo pulse peaks from the noise which is superimposed on the full echo waveform.

In instances of actual corrosion, then, the surface of the pit is very seldom flat. Therefore, a second "clean" echo is unlikely to be produced because of the sideways deflection (and eventual absorption) of much of the acoustic energy which is incident upon the rough surface of a real world corrosion pit.

Furthermore, some acoustic energy is lost altogether, such as that which travels path 310. This energy might otherwise have positively contributed to an echo peak. The loss of this energy makes detection and discrimination of peaks more difficult.

The echos received by the transducer will thus be much more complicated than that received from an "ideal" (flat) corrosion pit. Information is therefore lost unless a more sophisticated means of interpreting the full echo waveform, including the plurality of echos which follow the first, "front surface" echo.

Human error may result in lack of proper diagnosis of corrosion, especially when considering the massive number of full echo waveforms which are produced in a single "run" up a 20,000-foot oil well.

It is therefore desirable to perform expert, reliable, automated analysis of an extremely large number of waveforms comprising echos which arrive after the front-surface echo.

D. Frequency Domain versus Time Domain Analysis

Analysis techniques may roughly be divided into two classes.

The first class analyzes echos in the time domain. A measurement of the amplitude of the front-surface echo (described above) to determine the presence of fractures (and, perhaps by implication, pits) is probably the simplest example of a time-domain technique. A smaller front-surface echo presumably indicates a larger fracture (or pit), since any acoustic energy which entered a fracture (or pit) would not be returned to the transducer surface coincident in time with the front surface echo. See *Carson et al., Corrosion 86*, cited above.

The second class of analysis is that which converts the incoming echos into functions of frequency. Frequency domain analysis techniques involve the analysis of the spectral components of a returned echo signal to deduce information about the reflection surfaces which must have caused that particular array of spectral components.

Frequency-domain techniques have been used in order to avoid certain problems in the analysis of the raw, returned echos in the time domain. Raw, time-domain echos were often indistinct due to diffusion of the wavefront caused by complex and unpredictable interaction of the wavefront with the irregular surface of corrosion pits. The effect of this diffusion of pulse echos was to make it more difficult to distinguish when one echo ends and another begins, or even whether a given echographic formation constituted one echo or a sum of echos which traversed different paths but happened to arrive at the transducer at the same time.

Frequency-domain techniques have met with some success. Frequency domain techniques have been most commonly employed for measuring changes in the thickness of large areas of a wall, rather than for detection of localized pits and measuring their depth. But because a time-to-frequency transformation is necessary, the intuitive grasp of individual echo components was removed from the analysis process. What was actually analyzed was a frequency spectrum, not an untransformed representation of what was actually occurring in the physical world.

It is therefore desirable to reliably analyze pulse echos "directly," in the time domain.

In summary, it is desirable to efficiently use a full echographic waveform whose individual echo components have improved resolution so as to facilitate time-domain analysis.

SUMMARY OF THE INVENTION

In the field of the echography, the present invention is a system and method of preprocessing and transmitting information (such as echo waveform information) from a source (such as a transducer) to a destination (such as a rule-based computer system). The present invention reduces the absolute amount of information that is transmitted without reducing the amount of meaningful information that is conveyed. In this way, the present invention is effectively able to transmit more meaningful information than would be expected for conventional transmission systems. It also acts to reduce the amount of information processing that must be done at the destination.

The present invention has particular applicability to the transmission of digitized echo waveform information from a transducer used to perform pulse echo resolution of the surface irregularities of metal tubulars within the borehole of an oil well. This digitized information is transmitted up the borehole (called "uphole transmission") to a destination at the top of the borehole (such as a rule-based computer system) where it is analyzed. The preprocessing results in less data being transmitted for the information conveyed than would be the case if conventional transmission techniques were used. It should be appreciated that the present invention has applicability beyond the preferred field of use. It can be used in any environment where there would be a need or benefit for a transmission system or method where the amount of information that must be transmitted is more than can be transmitted using conventional transmission techniques and any given transmission media.

In the preferred mode, the present invention processes an echo waveform derived from the echo of an acoustic pulse launched toward a target surface. The echo waveform is converted into a monopolar waveform using an envelope detector and then smoothed using a low pass filter. The smoothed echo waveform is then passed through a logarithmic amplifier where it is compressed. The compressed and smoothed monopolar waveform is then digitized, and the digitized data is stored in a recirculating memory. The recirculating memory fills up and begins to overwrite itself. While the digitization is taking place, the echo waveform is simultaneously put through a threshold detector. Approximately 20 microsections after the amplitude of the echo waveform rises above a predetermined threshold the recirculating memory is frozen and the data within is prepared for transmission.

A binary counter measures the time period from the launching of the acoustic pulse to the time when the echo waveform reaches the predetermined threshold. This measured time period is multiplexed with the digitized echo waveform data frozen in memory and gain information from an automatic gain control within in the system.

These three data are subsequently transmitted in a multiplexed fashion uphole to the rule-base computer system.

BRIEF DESCRIPTION OF THE DRAWINGS

The invention is best understood by reading the following detailed description in conjunction with the accompanying drawings, in which like reference numerals refer to like elements throughout, and in which.

DETAILED DESCRIPTION OF THE PREFERRED EMBODIMENTS

1. Generation of Full Echo Waveform a. Curved Transducer

Figure 2:
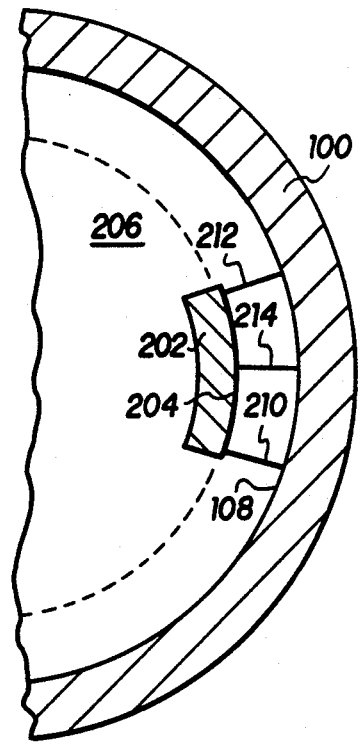
FIG. 2 represents a top plan view depicting the acoustic properties of a transducer according to the present invention.

Referring now to FIG. 2, a transducer 202 according to the preferred embodiment of the present invention is disposed in a sonde 206. The transducer 202 of the present invention is characterized in that its outer surface 204 is curved so as to match the curvature of its target surface. In the specific case of an oil well tubular 100, the transducer is curved only in a direction perpendicular to the axis of the tubular. Along lines parallel to the tubular axis, the preferred embodiment of the transducer is straight. Thus, the transducer outer surface 204 may be defined mathematically as a section of a right circular cylinder. Curved transducers suitable for embodying the present invention are commercially available from, for example, Ultran Laboratories in State College, Pa.

Figure 1:
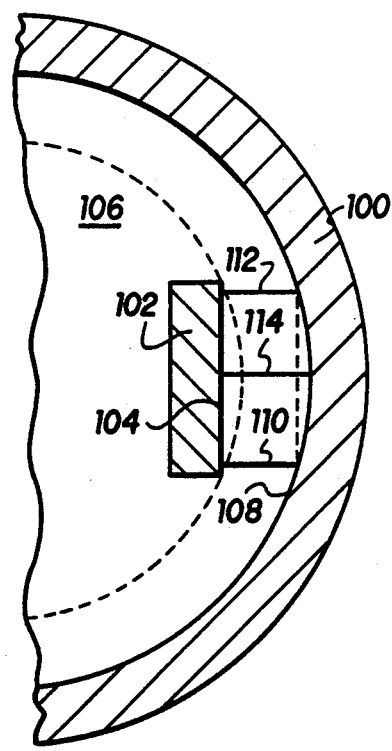
FIG. 1 represents a top plan view depicting the acoustic properties of a known transducer within a borehole tubular.

In roughly the manner described with respect to the known transducer 102 (FIG. 1), an excitation pulse causes an acoustic wave to emanate from transducer surface 204 toward the inner surface 108 of tubular 100 to cause the wave to hit the inner surface 108 "in phase." An acoustic echo is thus returned to transducer surface 204 for detection and eventual analysis. In a preferred embodiment of the present invention, a rectangular excitation pulse of 300 volt magnitude, 50 nanosecond duration, and 1-millisecond repetition period is employed for ease of detection and greater resolution of the returned echos. The transducer emits an ultrasonic wave with a center frequency of 4.5 Megahertz (MHz).

Of course, these values are typical values. The values may be varied according to the demands of particular experiments or applications. Generally, the invention may be practiced with excitation pulses anywhere in the 10–1000 volt range. Pulse durations may vary from 10–100 nanoseconds for a 4.5 MHz transducer. Repetition periods may be as long as convenience requires, and may be as short as permits noninterference of excitation pulses with returned echos from previous citation pulses. Standoffs (transducer-tubular separation) may be chosen as required, so long as a recognizable signal is returned from the target surface. The ultrasonic wave frequency may be any frequency which the environment allows, but is advantageously in excess of the 1 MHz signals used by others in ultrasonic evaluations.

A difference in performance of the transducers 104 and 204 (FIGS. 1 and 2, respectively) is that the curved transducer face 204 ensures that the round-trip travel time of all portions of an acoustic pulse is substantially identical, regardless of whether paths 210, 212, or 214 are traversed. To achieve this equality of travel time, the center of curvature of the transducer surface must be the same point as the center of curvature of the inner wall of the tubular.

The choice of identical centers of curvature results in a noticeable improvement in the "crispness" of the returned echo pulse. (A "crisp" pulse is characterized as having large amplitude and small time duration.) Increased amplitude allows easier detection of each individual echo pulse, and decreased pulse width facilitates the discrimination of pulses from adjacent pulses. (Although it is not evident from FIG. 2, the signal received by transducer 202 is comprised not only of a single echo, but rather multiple echos. The production of these other echos will be described in more detail below, with regard to FIG. 9.)

Figure 4:
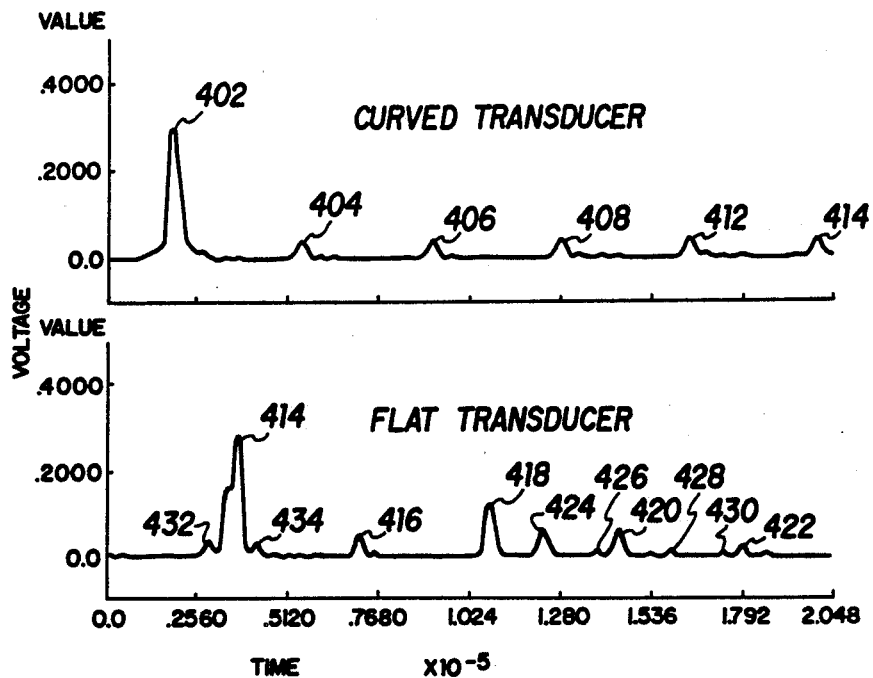
FIG. 4 presents a comparison of actual waveform envelopes of signals reflected from uncorroded pipe, illustrating the improvement in quality of signals to be expected when using a curved transducer according to the preferred embodiment of the present invention.

FIG. 4 shows waveforms reflected from uncorroded pipe with a 5.5-inch inside diameter. The top panel of FIG. 4 shows a waveform of echos in an experiment employing a curved, 0.75×0.63-inch rectangular transducer with a 5 MHz center frequency. The bottom panel of FIG. 4 shows a waveform of echos produced in an experiment employing a flat-faced one-inch diameter transducer with a 5 MHz center frequency.

The difference in the two waveforms is substantial, especially considering the fact that the target surface was smooth and uncorroded. Both waveforms demonstrate the "front surface echos" 402 and 414 which, in most circumstances, are the echos of greatest magnitude. The remainder of each full echo waveform also contains a "multiple structure". Multiple structures are formed as a result of internal reflections within the tubular (see FIG. 9). Multiple structures manifest as substantially equally-spaced sets of peaks, since the acoustic wave is presumably reflecting internally between the same two surfaces before a portion of the energy is returned to the transducer for detection. The multiple structure for the full echo waveform produced by the curved transducer is shown as peak elements 404, 406, 408, 410, and 412. They are easily discernable above the "noise floor" of the full echo waveform.

The multiple structure of the full echo waveform produced by a flat transducer is much more difficult to discern. The multiple structure (as could later have been discerned) comprises peaks 416, 418, 420, and 422. The presence of this multiple structure is masked by the presence of other "false" echos 424, 426, 428 and 430.

Although, in the present experiment, it was known a priori that the surface of the pipe was uncorroded, the presence of false echos such as 424, 426, 428, and 430 could have led an observer to believe that the tubular surface was in fact corroded. Any of the false echo peaks could reasonably have been interpreted as echos caused by reflection of acoustic energy against the bottom surface of one or more corrosion pits. As described above, the round-trip travel time of an acoustic wave which enters a pit is increased because of the greater distance over which the acoustic wave must travel in order to reach the bottom of the pit, as compared with the distance from the transducer to the uncorroded front surface of the tubular.

To interpret these false echos as pit echos would be reasonable. Such a formation of peaks could be caused by the conversion of longitudinal acoustic waves to shear acoustic waves, in a process called mode conversion which is well known in the art. Also, it would be reasonable to ascribe this formation of false echo peaks to internal reflections within the converted waves, as indicated above in the discussion related to FIG. 3.

The difference between the front surface echos 402 and 414 produced by curved and flat transducers, respectively, is also apparent from FIG. 4. A front-surface echo 402 produced by a curved transducer is shown as being a "crisp" echo with side lobes of much-reduced amplitude. In contrast, the front-surface echo 414 produced by a flat transducer exhibits the broadening effect characteristic of pulse dispersion, as described above in the Background of the Invention section. Also, the side lobes 432 and 434 are of much larger magnitude than those of curved transducer front-surface echo 402. Conceivably, in an actual downhole scenario, it would be indeterminate whether, for example, echo 432 was the front-surface echo and echo 414 was a pit echo. Although a sophisticated technique of analyzing full echo waveforms could possibly eliminate the interpretation of echo 432 as a front-surface echo, it can be seen from FIG. 4 that the quality of full echo waveform is much enhanced through the use of a curved transducer. The full echo waveform of enhanced quality allows greater reliability, regardless of the degree of sophistication of the analysis method subsequently employed.

b. Coverage of the Target Surface

Figure 5:
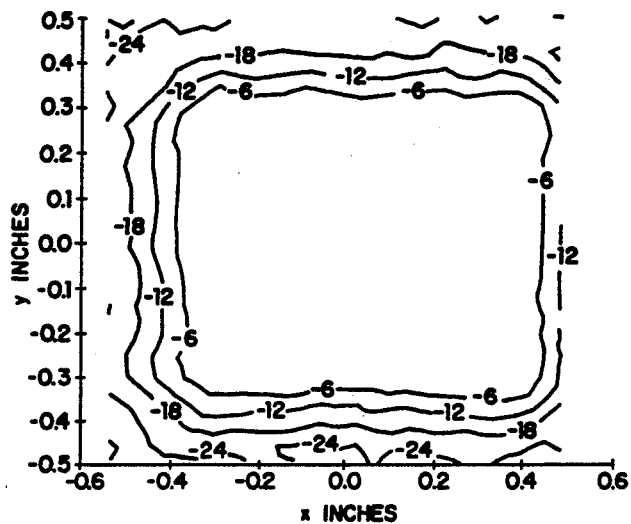
FIG. 5 represents an actual measured ultrasonic beam pattern for a curved rectangular transducer according to the present invention.

FIG. 5 portrays an ultrasonic beam pattern for a rectangular transducer having a transducer surface with a curvature matching a tubular front surface. (In actuality, FIG. 5 shows peak echo amplitude as a function of target reflector position relative to the center of this transducer. For production of data contributing to this contour plot, a 0.125-inch diameter steel rod with a rounded end was used as a target reflector.) FIG. 5 is thus essentially a map of the acoustic energy which would strike the surface of a tubular. It is to be emphasized that this diagram of acoustic energy, called the "spot size," relates to the tubular surface, and not the size of transducer itself.

The particular data shown in FIG. 5 was obtained from a 0.75×0.63 inch transducer having a "standoff" (separation from the target surface) of 1.5 inches, a convex radius of 2 inches, and a 4.2 MHz peak frequency (4.5 MHz at 6 dB down).

The numerical decibel figures indicate the reduction in amplitude from the point of maximum amplitude which is located in the center of the "spot." The degree of attenuation at which to define the edge of the spot is somewhat arbitrary, but the −12 dB contour has been found to be a reasonable choice.

An accurate determination of the size and shape of the spot is necessary in order to determine the coverage of successive applied acoustic pulses as the sonde moves up the tubular. It is also important for the calculation of pit area, as will be discussed in detail below.

Figure 6A:
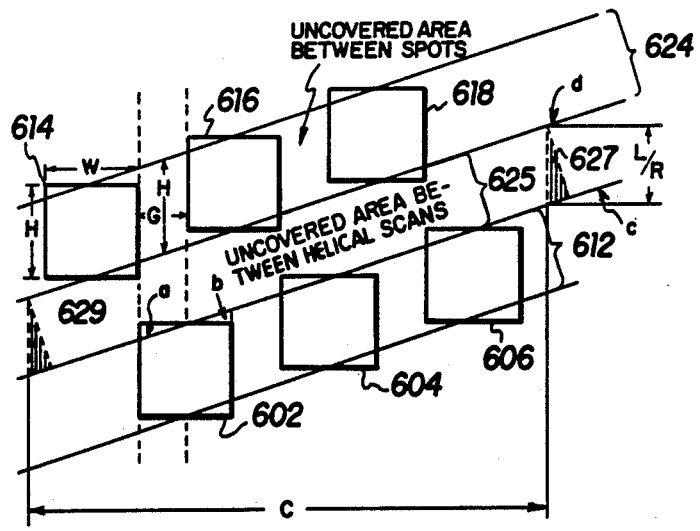
FIGS. 6A and 6B represent examples of a coverage diagram demonstrating the nonoverlapping and overlapping, respectively, of acoustic "spots" schematically superimposed on a folded-out interior surface of an oil well tubular.
Figure 6B:
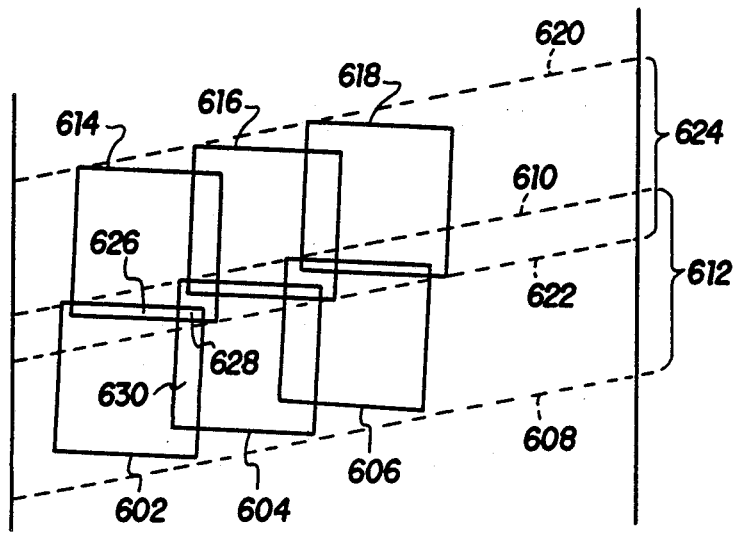

FIGS. 6A and 6B depict the folded-out inner surface of a tubular, in a way which is common in the art. The tubular is assumed to have a vertical orientation. The left and right extremes of the diagram are understood to be joined together so as to express the transverse circular continuity of the cylindrical tubular.

Spots of successively applied acoustic pulses are represented on the inner surface of the tubular. The transducer (and therefore the spot) according to a preferred embodiment of the present invention may traverse what (in three dimensions) is a helical path.

The helical path in three dimensions is represented in both FIGS. 6A and 6B as upwardly sloping paths, examples of which are indicated at 612 and 624. In FIG. 6A, an intervening strip 625 is present. Examples of a series of successive spots are shown at 602, 604, and 606. It is to be understood that the spots continue to be applied across the entire pathway 612 and then continue on pathway 624, where further exemplary consecutive spots 614, 616, and 618 are depicted. Intervening spots, and additional pathways beneath 612 and above 624, have been omitted for purposes of simplicity. Also, it is to be recognized that the figure is not drawn to scale, but the spots are drawn disproportionately large in comparison to the tubular for diagrammatic clarity.

The calculation of the coverage of the sequence of spots can be accomplished readily, as follows. We first define the appropriate variables:

| | |
|---|---|
| Rotation rate (rev/sec) = | R |
| Transducer height (inches) = | H |
| Transducer width (inches) = | W |
| Excitation Pulse Frequency (cyc/sec) = | F |
| Tubular Inner Circumference (inches) = | C |
| Logging Rate (inches/sec) = | L |

Assume for now that the spot areas do not overlap. This case is shown in FIG. 6A.

First, the area of the uncovered patch 625 formed by the non-overlapping tops and bottoms of the spot-areas (bounded by lines c & d) may be calculated. We first note that the upward travel of the sonde per revolution=L/R. Triangular portions of the spot-area on either side of the horizontal center, labeled a & b in FIG. 6A, can be reflected through the center of the top of the spot to give an uncovered strip bounded by the scan lines c & d. The Vertical dimension of the strip 625 is equal to:

Upward travel−spot height=(L/R−H)

For each revolution we can make the strip a perfect rectangle by drawing a line at the bottom which is at the lower end of, and perpendicular to, the upper helical path (d). The resulting triangle 627 is moved to the other end to 629 to form a rectangle between lines c, d, and triangles 627 and 629.

The area of this strip, per revolution, is just the vertical dimension times the circumference, (L/R−H)*C.

Now for the area uncovered between (horizontally) successive spot areas:

Time to move to next spot-area=1/F

Rotation velocity=Rev/sec*inch/rev=R*C
Distance between spot centers=(R*C)/F
G=Width of area uncovered per spot=((R*C)/F)−W
Number of spot areas per rotation=

(#spots/sec)/(Rev/sec)=F/R

Area uncovered per spot=G*H

Area of patches not covered between successive spots per rev.=G*H*F/R

The total area available to be covered per revolution is the product of the upward distance and the circumference:

Area available for coverage per rev.=C*L/R

Thus the total uncovered area as a fraction is:

$$\frac{(L/R - H)*C + (R*C/F - W)*H*F/R}{C*L/R}$$

Dividing through by the denominator gives:

Fraction uncovered =                                             (Eq. 1)

(1 − H*R/L) + (1 − F*W/(R*C))*H*R/L

Also, the fraction covered = 1 − fraction uncovered =           (Eq. 2)

1 − (1 − H*R/L) + (1 − F*W/(R*C))*H*R/L

Now let A=H*R/L and B=F*W/R*C. The covered area can be expressed as a percentage of the total area:

Covered Area (%)=100. * [1−[(1−A)+A*(1−B)]]    (Eq. 3)

The first factor, A, is a dimensionless number determining the amount of vertical gap (or overlap). The second factor, B, is a dimensionless number determining the amount of horizontal gap (or overlap). The interaction of these two numbers determines the amount of coverage.

Note that if A=H*R/L=1 and B=F*W/(R*C)=1 then there are no uncovered areas. This corresponds to the case of adjacent spot-areas which touch at top and bottom. In this case, the values for H and W are the minimum values for which there is 100% coverage, given R, L, C and F.

Note also that if $A>1$, $B>1$ then there is more than 100% coverage. The terms in parenthesis in Eq. 3 become negative and add to the coverage.

Eq. 3 can be further simplified by canceling the unity and A terms. This leaves the following equation for the coverage.

$$\begin{aligned} \text{Covered Area (\%)} &= 100. * A * B \\ &= 100. * \frac{H*R*F*W}{L*R*C} \\ &= 100. * \frac{H*F*W}{L*C} \end{aligned} \quad \text{(Eq. 4)}$$

This equation implies there is no dependence of coverage on the rotation rate. This lack of dependence on R is due to the way coverage has been defined. For these equations, any time an additional area is probed, it is included in the coverage calculation, regardless if this area had already been probed by another spot-area. Thus, Eq. 4 shows that 100% area coverage can be obtained by rotating the transducer at any speed so long as $H*F*W/L*C=1$. It does not imply that all areas of the pipe are covered, however. To insure 100% coverage with all areas of the pipe being scanned, term A must equal unity and term B must equal unity.

In practice, coverage in excess of 100% is desirable to gain added information about given areas of the tubular surface. However, in this context of overlapping coverage, the very concept of "coverage" becomes ambiguous. (If two spots overlap, but there is still an area completely untouched by any spots, is that greater or less than 100% coverage?) When considering overlapping spots, then, resort is best made to diagrams, such as FIG. 6B to determine the nominal transducer rotation rate R. In any event, it is possible to adjust the rotation rate, R, and excitation frequency F, in conjunction with the pull or logging rate, L, to ensure total coverage of a tubular surface during a survey.

As can be seen from the above formula, the tubular circumference (C) is the only variable which is not independently controllable by the sonde designer. Of the controllable variables, it is the transducer size which is most directly relevant to the quality of resolution which is to be expected from the device. Ideally, a small transducer height H and width W would be employed, so as to provide measurement of smaller pits on the tubular surface. In a practical system, however, the data rate of the information which must be transmitted uphole is a limiting factor on the minimum size of the transducer, even assuming that the other parameters in the equation are optimized for maximum resolution of detail. A smaller transducer surface size H*W requires a greater bandwidth of information since a greater number of full echo waveforms must be detected and transmitted in a given time period.

Referring to FIG. 6B, the concept of coverage of greater than 100% is indicated by areas such as 626, which is covered by two spots. Area 628 has been covered by four spots. Area 630, like area 626, is covered by two spots, but the overlap comprises overlap of consecutive spots, rather than by spots in the next path. Of course, the amount of coverage as shown by the overlap of paths 624 and 612 (which overlap is defined by lines 610 and 622) is easily controllable. By manipulation of any of the parameters of the above formula, the size of the overlapping zones 626, 628 and 630 can easily be chosen.

Although the transducer rotation rate R does not appear in Eq. 4, R could be adjusted to obtain desired coverage, in addition to adjusting the pulse repetition rate F and the logging rate L.

As the percentage of coverage increases, the condition of the tubular surface can be more accurately determined. This more accurate determination is made possible by the fact that information about any given area may be gained from more than one spot's acoustic echos.

Figure 7:
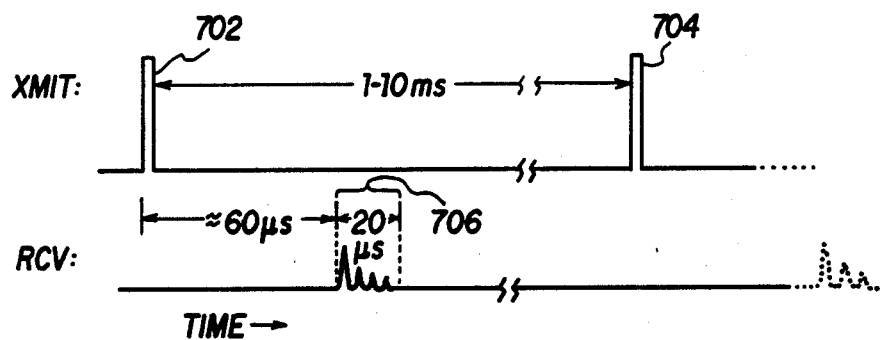
FIG. 7 is a timing diagram representing an excitation pulse and subsequent returned echos according to the present invention.

Referring now to FIG. 7, a timing diagram indicating the occurrence of a typical sequence of excitation pulses and the envelopes of the resultant acoustic echos are presented. In a preferred embodiment, an excitation pulse of typical magnitude 300 volts and duration 50 nanoseconds is applied every 1000 microseconds. This 1 kHz excitation pulse frequency has been found to be a practical excitation pulse frequency, given the fact that the returned acoustic echo pulses resulting from a first excitation pulse 702 must die out before the application of the subsequent excitation pulse 704. If the echos had not subsided, the transducer, which, in the preferred embodiment, both transmits the excitation pulse and receives the echos, would not be able to accurately receive the echos because of the overwhelming effect of the much stronger excitation pulse. Also, echos of a first excitation pulse which had not been substantially attenuated would interfere with accurate reception of the echos of a subsequent excitation pulse.

Figure 8:
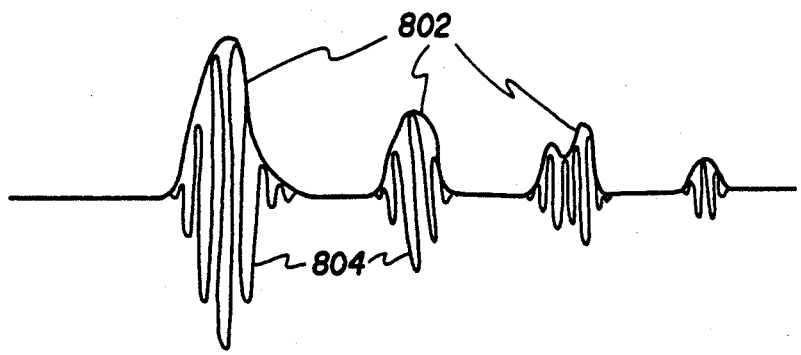
FIG. 8 details the high-frequency components and envelopes of typical acoustic signals.

It is to be understood that, regarding echo waveforms such as those illustrated in FIG. 7, the echo waveform actually comprises a set of pulse-modulated sine waves 804 (FIG. 8). What is typically represented in echo waveforms (as in FIG. 7) is merely the envelope 802 of these pulse modulated sine waves (pulse modulation as used herein need not imply a pulse of a single magnitude, but may be an analog shaped pulse). Also, it is not meant to be implied that the sine waves in the various pulses 802 are meant to be in phase, or even well-defined sine waves per se. The higher-frequency signals within the envelope may be the sum of interfering sine waves which are returned from a rough or corroded tubular surface so as to be combined in a complex way.

The present invention contemplates a particular embodiment in which 5 MHz sine waves are employed to achieve greater resolution than transducers of known systems, which used frequencies of approximately 1 MHz or below.

c. Bandwidth Reduction

The preferred embodiment of the present invention uses narrow, high-frequency pulses in conjunction with a pulse waveform analysis method which can determine the area and depth of corrosion pits much smaller than the spot size. For detecting pits of a required minimum size, larger transducers may be used than was previously possible. The use of larger transducers causes embodiments of the present invention to possess an inherent bandwidth compression, as compared with known systems.

In the preferred method according to the present invention, the full echo waveform is measured. The limitation noted above in the Background of the Invention section is avoided by recording both the front-surface and pit-surface echos in the full echo waveform. In the case where the acoustic wave intercepts both the front surface and the pit surface, the individual echos are analyzed to detect the pit and measure its depth. Thus, a very small pit can be detected even though the ultrasonic wave may impact an area beyond the perimeter of the pit itself.

One advantage of the method according to the present invention is the reduction in data rate necessary to transmit data describing a given area. Although the present method requires transmission of echo data for all significant echos in the waveform, this is still less data than that associated with known methods. In the following example, the data rates for the two methods are compared. Here, it is assumed for simplicity that the spots are square, and that the smallest pit area to be detected is a square ⅛-inch on a side. It is also assumed that successive spots are immediately adjacent (with no overlap and no gaps, either horizontally or vertically). Finally, it is assumed that any surface coincident with the "effective" edge of the spot area will be detected, whereas any just outside the edge will not be detected. In general, detection of surfaces near the spot edge will depend on the slope of the sensor response contour (FIG. 5) and the detection threshold. The "effective" size of the spot (considering the edges' possible echo characteristics) may thus be larger than the spot dimension as defined by the −12 dB contour (FIG. 5). This enlarged effective spot size may affect the following bandwidth compression calculations accordingly.

In known methods, the transducer spot area must be much smaller than the ⅛ inch × ⅛ inch square pit. For the pit to be detected, the spot area must completely fit inside the pit for at least one reading. Since, in practical downhole scenarios, there is no control over the actual placement of the spot center in relation to the pit center, the "worst-case" placement must be assumed (i.e., the beam must be assumed to be centered in the pit). Over this square pit, all 8 spots around the center spot intersect non-pit areas at the edges (pit not detected). Thus, to insure that at least one spot covering the pit does not intersect the uncorroded tubular surface surrounding the pit, the area of the spot must be at most 1/9th that of the pit area. For the square pit this gives a spot area of 0.0017 sq. inches. Two readings, (1) the first echo time, and (2) the first echo amplitude, must be recorded for each pulse. Thus, the number of readings per sq. inch is (1/0.0017)×2=1,152. This data rate will provide detection and depth measurement down to square pits ⅛ inch on a side.

For the method according to the present invention, a much larger area is sensed for each pulse. In practice, a square pit ⅛ inch on a side can be detected using a beam which is 40 times larger. Thus, the spot size for each pulse can be 40×⅛×⅛ 0.625 sq. inches. The number of readings per pulse depends on the number of echos exceeding the threshold. On average there will be about 10 echos to be recorded. Three features per echo must be measured: (1) echo time; (2) echo amplitude; and (3) echo width. Thus, there are 30 values per pulse. The number of readings per square inch is 10×3/0.625=48— a factor of 24 smaller than that of the prior method.

The reduction in data rate for the new method is achieved at the cost of spatial resolution on the pit. The prior method will give a much better localization of the pit on the pipe surface. However, for most practical applications, the maximum pit depth for a given region is of primary concern, rather than excruciatingly localized spatial resolution. The maximum pit depth has been judged to be a good indicator of the condition of the tubular and the corrosion progress in the tubular.

d. Full Echo Waveforms i. A Simple Example

Figure 9:
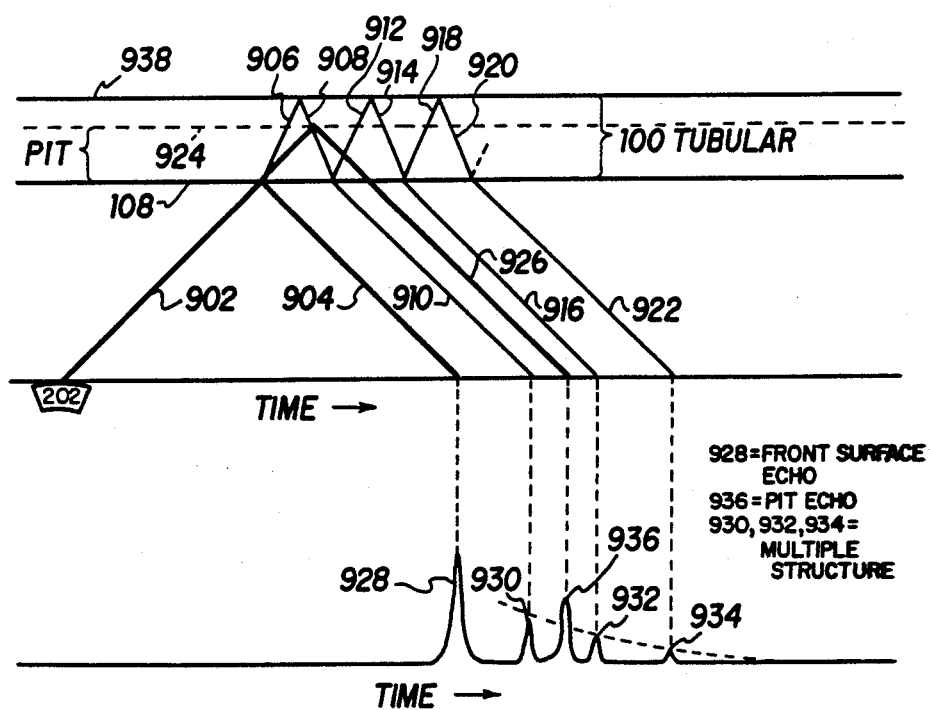
FIG. 9 represents a timing diagram indicating the full echo waveform produced from a single excitation pulse on a surface having an "ideal" (flat-bottomed) corrosion pit.

FIG. 9 is a timing diagram which illustrates with specificity the formation of a full waveform of pulse echos. The horizontal position indicates time, and the vertical position indicates the physical position of the various acoustic wavefronts travelling between the transducer surface 204 and the front surface 108 of the tubular 100. FIG. 9 also depicts the wavefronts reflected from the surface of an "ideal" (flat) corrosion pit which has eaten into the tubular to the depth indicated at 924. (It should be noted that the tubular is presented in FIG. 9 as a straight line, since this is a timing diagram. FIG. 9 is not a physical diagram as is, for example, FIG. 2.)

The full waveform of acoustic echos is formed as follows. An excitation pulse excites transducer 202 so as to cause an acoustic pulse of high amplitude and short duration to emanate from the curved surface 204 of transducer 202. Assuming a sinusoid of 5 MHz frequency, only two cycles of the sine wave are generated. The wavefront travels at its known speed (1300 m/second in oil) through the liquid medium occupying the space between the transducer 202 and the tubular front surface 108, as indicated along path 902. Much of the acoustic energy is reflected from the tubular's front surface 108, and is returned as a "front surface echo" toward the transducer 202 along path 904. The front surface echo is indicated as peak 928.

Not all of the acoustic energy incident on path 902 is reflected back toward transducer 202. Some of the acoustic energy is transferred to the tubular material itself. That energy which is transferred traverses a path 906 at a speed in metal (typically 6100 m/second) which is different than the speed of the acoustic energy in the liquid (1300 m/second in oil) internal to the tubular. Therefore, the slope of path 906, indicative of the speed of the acoustic wavefront, is different from that of path 902.

A portion of the energy which travels along path 906 is reflected at the outer surface 938 of the tubular 100 to be returned toward the tubular front surface 108 along path 908. Some of this energy along path 908 is in turn transmitted along path 910 toward the transducer 202, whereas some of it is reflected from tubular front surface 108 back into the tubular material along path 912.

A process of repeated and alternating transmission and reflection (indicated along paths 914, 918 and 920) is continued until virtually all the acoustic energy has been lost to the environment and to conversion to thermal energy.

Various acoustic echos produced by energy escaping the repeated internal reflections within the tubular 100 are transferred back toward the transducer 202 along paths 910, 916, and 922. Since energy is being continually diminished in the internal reflection process at the tubular surfaces' interfaces 108 and 938, the magnitude of acoustic pulse wavefronts are continually decreasing in power as time passes. This diminishment in energy is indicated by the roughly exponentially decreasing magnitudes of echo peaks 930, 932, and 934 which are shown as representing the acoustic energy returned along paths 910, 916, and 922, respectively. Collectively, the set of peaks 930, 932, and 934, etc. are referred to as a "multiple structure" (MS). By a convention used in this disclosure, the front surface echo is not considered a part of the multiple structure.

It is being assumed in this explanation that an ideal corrosion pit, having a flat surface located at 924, occupies an area on tubular front surface 108 which is smaller than the spot size. The acoustic energy which enters the tubular's corrosion pit to a depth indicated by 924 will take a longer time to traverse the round-trip pathway 902 and 926 than the front surface echo along paths 902 and 904. The returned "pit surface echo" produces a peak of acoustic energy at 936.

This pit surface echo 936 occurs at a point in time which is determined by the distance between tubular front surface 108 and pit surface 924. This distance is independent of the thickness of the tubular (unless, of course, the corrosion pit has eaten entirely through the tubular to actually form a hole in it). The pit surface echo can therefore occur at any point between, or even be superimposed on, the multiple structure's peaks 930, 932, and 934. The depiction in FIG. 9 of pit surface echo 936 as occurring substantially between multiple echo peaks 930 and 932 is thus arbitrary.

The acoustic energy detected by the transducer is first envelope-detected to reduce the signal bandwidth (to approximately 2 MHz in the preferred embodiment). The envelope is then sampled at a high frequency (typically 5.0 MHz) in the preferred embodiment. These discrete-time samples are digitized so as to allow formation of a full echo waveform such as that indicated in FIG. 9.

ii. Actual Example

Figure 10:
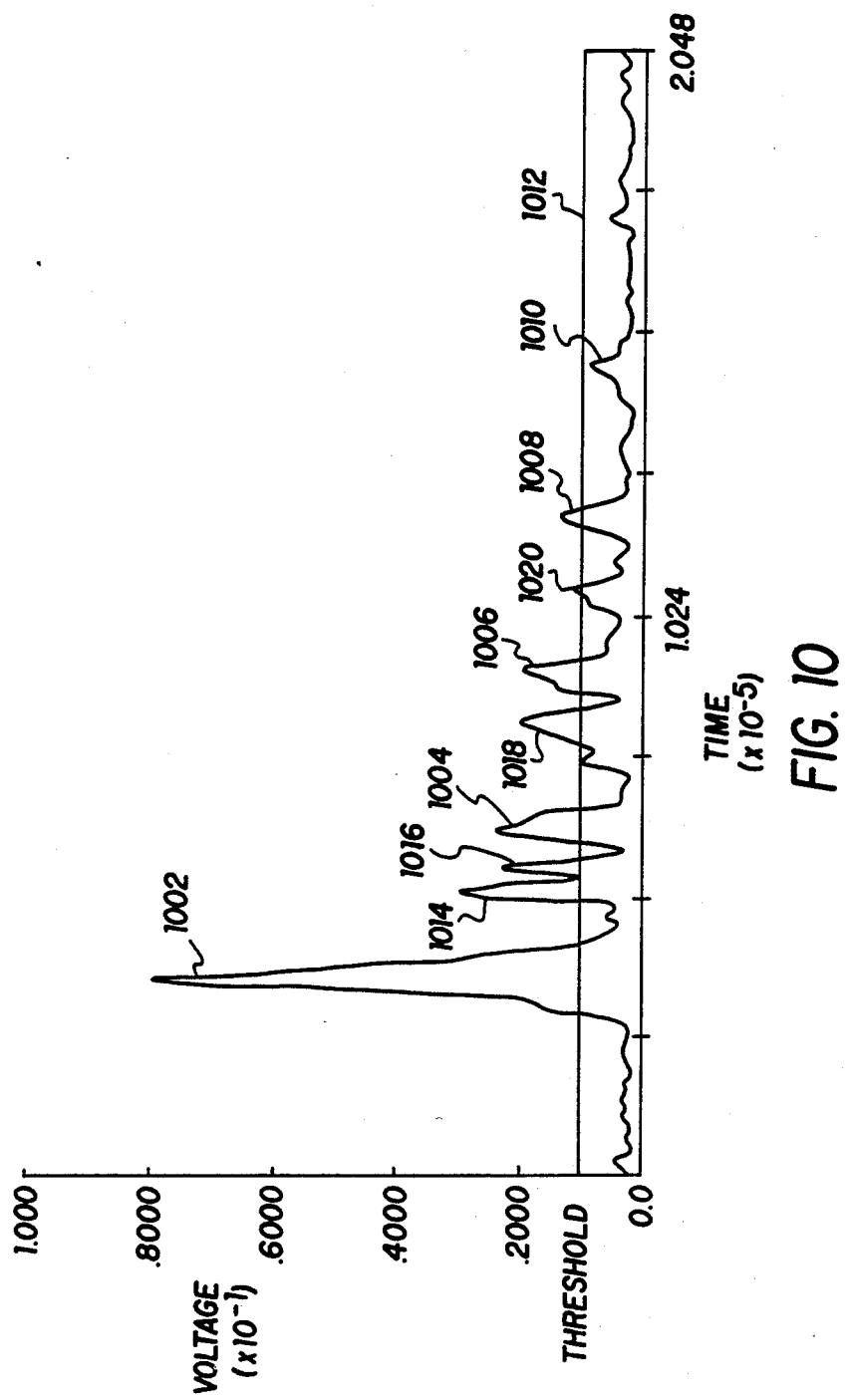
FIG. 10 represents an actual full echo waveform to be expected when a transducer according to the present invention operates on a corroded tubular surface.

FIG. 10 presents an actual full echo waveform which is characteristic of those which are likely to be encountered in practice. The difficulty in deciding whether a particular configuration constitutes a peak (and, if so, how to distinguish whether a particular formation comprises only one or a plurality of peaks), is that confounding signal structures (such as multiple structures from both the front surface echo and from any pit surface echos) are mixed in with the directly reflected surface echos. It is the collection of all these peaks, whether sharply defined or dispersed, which constitute the full echo waveform. It is the full echo waveform that is analyzed to determine which assumed peak is the front surface echo, which echo(s) are pit surface echo(s), and which echo(s) are multiple structures associated with either the front surface or pit surface(s). (If it is the multiple structures which are the signals of interest, for example, in determining remaining wall thickness, then the front surface echo and any pit surface echos would more properly be called the "confounding signal structures.")

In the preferred embodiment of the invention, the acoustic energy which is detected by transducer 202 is continuously measured and digital representations of the magnitude of the returned acoustic energy are made at regular time intervals. On the basis of this discrete-time digital information, the rule-based Expert System according to a preferred embodiment of the present invention operates to determine the most likely tubular surface condition which could be responsible for the digital full echo waveform under consideration.

Based upon analysis of the returned, full echo waveform shown in FIG. 10, echo 1002 was determine to be a front-surface echo. Regularly timed echos 1004, 1006, 1008, and 1010 form a multiple structure. Various echo peaks never achieve a threshold value 1012 which is significantly greater than the noise floor indicated by the slight perturbations above 0.0 on the vertical axis. Multiple structure echo 1010 is, in this example, one of those echos with diminished amplitude.

According to a preferred embodiment of the present invention, such a threshold 1012 may be established so as to eliminate from consideration ∓spurious" echos which are of unknown origin. If the threshold 1012 had been set slightly higher, echo 1020 would have been eliminated from consideration. Although it is known in this example that echo 1020 was in fact a spurious echo, echo 1020 could reasonably be interpreted as a pit echo. Smaller-amplitude echos are advantageously eliminated from consideration because the amount of energy which contributed to their formation is correspondingly small, and are more likely to have been caused by the dispersive effects of, for example, mode conversion.

Echos other than the front-surface echo 1002 and the known detected multiple structure echos 1004, 1006, and 1008 are first assumed not to be false echos. Echos such as 1014, 1016, and 1018 were determined to be pit echos.

A comparison of a full echo waveform of FIG. 10 with the simple full echo waveform of FIG. 9 demonstrates the utility of a more sophisticated analysis method for determining the cause of each echo in the full echo waveform.

Figure 21:
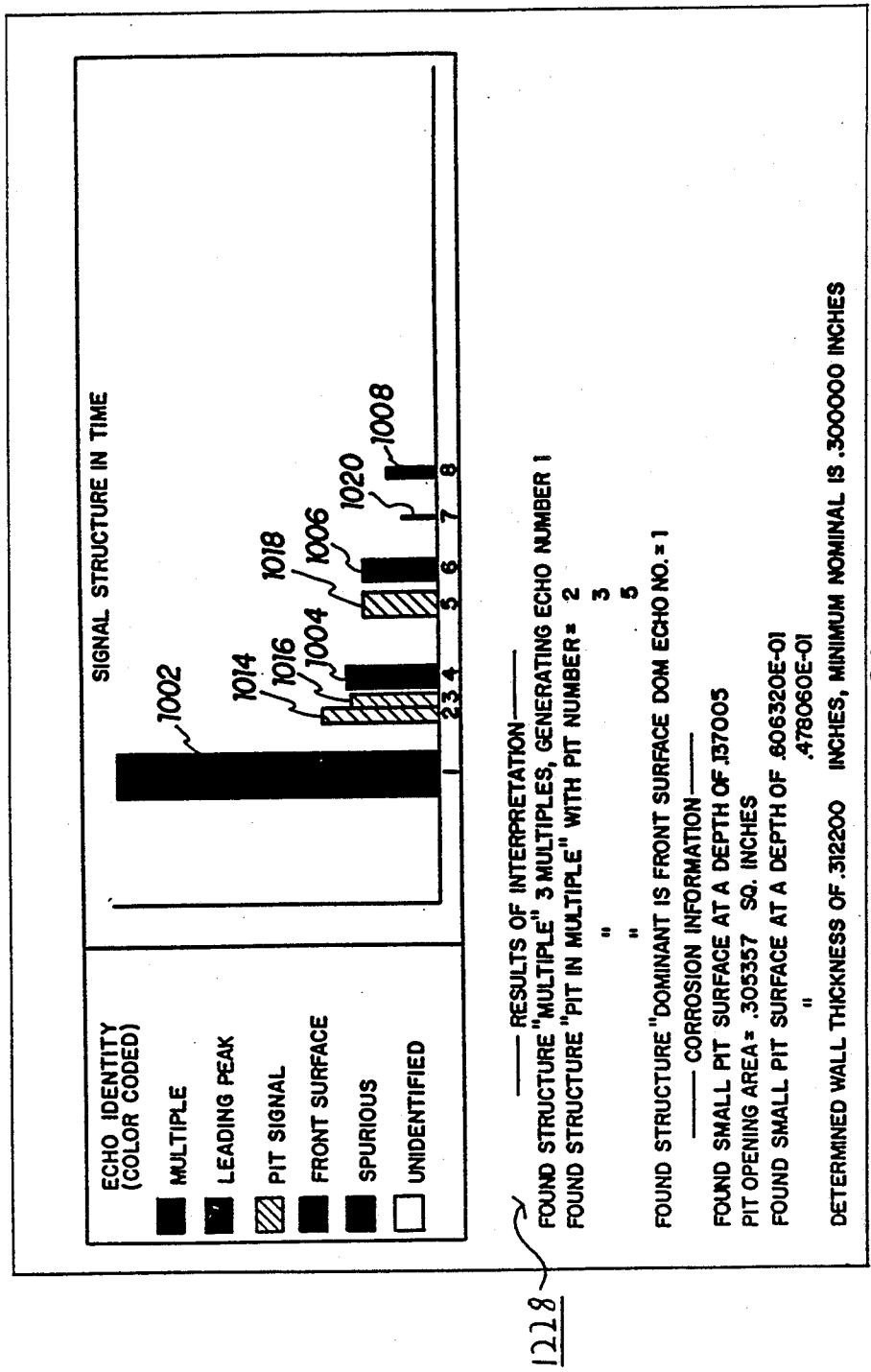
FIG. 21 illustrates a user-interface display for the processing example illustrated in FIG. 10.

In the discussion relating to FIG. 21, the full echo waveform portrayed in FIG. 10 will be used as an example to demonstrate the process by which the rule-based system, according to the present invention, isolates and identifies each echo exceeding a known or calculated threshold.

2. Principles of Analysis of Full Echo Waveform

Information about the condition of the tubular is derived from the full echo waveform. The depth and area of corrosion pits is valuable information.

a. Pit Depth

First, the depth of a pit may be derived from the time separation between the front surface echo 928 and the pit surface echo 936 (FIG. 9). The depth of the pit $D_{pit}$ is equal to one-half the product of the speed of sound in the liquid $V_1$ and the time difference $T_{p-f}$ between the front surface echo 928 and the pit surface echo 936. Symbolically, $$D_{pit} = 0.5 * V_1 * T_{p-f}$$

The tubular thickness can be determined from multiple structures which are present in the full echo waveform. The only multiple structure illustrated in FIG. 9 is that which comprises peaks 930, 932, and 934. This multiple structure is based on reflections between the inner surface of the tubular 108 and the tubular's outer surface 938. Based on this multiple structure, the tubular thickness is equal to one-half the product of the speed of sound in the tubular material (presumptively metal) and the time separation of the multiple echo peaks.

The separation of adjacent peaks in a given multiple structure should be constant, regardless of which pair of adjacent peaks are chosen; that is, the time separation between peaks 930 and 932 should be identical to the time separation between 932 and 934. A more accurate estimation of the tubular thickness can be gained by using a weighted average of the various peak separations. That is, an average of the 928–930, 930–932, and 932–934 separations could be used, with greater weighting being given to the earlier (and presumably stronger) peaks.

Determination of this average peak separation lends itself readily to solution by a rule-based system. The advantages of a rule-based solution become evident in considering the case when a pit echo 936 occurs nearly coincident in time with a multiple structure peak. In this case, the location of the multiple structure peak is indeterminate because the pit echo distorts the multiple structure peak. A rule-based system could easily analyze the multiple structure's characteristics to determine if one or more of the multiple structure peaks was anomalous. In this case, the anomalous peak could be ignored in the calculation of the multiple structure peak separation.

Although not specifically illustrated in FIG. 9, multiple structures may be associated with a pit echo 936 as well as a front surface echo 928. In order for a multiple structure to be formed by a pit, there must be present a large flat pit whose bottom is perpendicular to the incident acoustic energy. Due to the nature of "real-world" corrosion, such large, flat pits (and their accompanying multiple structures) are statistically uncommon. (Any multiple structures associated with pit echo 936 have been omitted from FIG. 9 for purposes of simplicity.) A measurement of the remaining wall thickness (RWT) (the distance between surfaces 924 and 938) behind a corrosion pit can be determined in the same manner as described above, for the case of a multiple structure defined by the front surface.

In the case of a pit multiple structure, the minimum remaining wall thickness can be determined from the multiple structure having the minimum separation of all multiple structures encountered. This minimum remaining wall thickness gives a direct indication of how close a given corrosion pit has come to the outer surface of the borehole tubular. This direct indication of RWT can be used in conjunction with the direct measurement of pit depth (described above) to determine the progress of a given corrosion pit with a higher degree of confidence. Increased (or decreased) confidence derives from an ability to verify (or contradict) one measurement by comparing it with another. This confidence consideration is ideally suited for solution by a rule-based system.

Ideally, the depth of a given corrosion pit and the remaining wall thickness associated with that corrosion pit should total the nominal thickness of the borehole tubular. Any deviations or inconsistencies between the pit depth indication and the remaining wall thickness indication may be analyzed using a rule-based system so as to quantify the confidence level in a given conclusion as to the corrosion's progress. The interaction of the pit depth measurement and the remaining wall thickness measurement in the rule-based analysis is described in greater detail below in the section on Rule-Based Analysis of Full Echo Waveform.

Although the preferred embodiment of the present invention contemplates detection of imperfections on the inner surface of a borehole tubular, information concerning the outer surface is also easily determined.

In practice, corrosion pits almost never take on the "ideal" character indicated in FIG. 9. That is, the pit surface of an actual corrosion pit is usually much more complex, as was shown in FIG. 3. A real-world corrosion pit does not have a single depth, as was indicated by the distance between surfaces 108 and 924 in FIG. 9. An actual corrosion pit is likely to have a range of depths, so that a single pit echo (936 in FIG. 9) is not to be expected.

Referring again to FIG. 3, paths of various portions of an acoustic pulse emanating from the curved surface 204 of transducer 202 are illustrated.

Paths 302 and 306 depict the paths which are followed by the acoustic energy which is incident upon a corrosion-free area of the tubular surface 108. The full waveform acoustic signals from these portions of the wave front are the same as those produced in front surface echo 928, and multiple echo structure 930, 932, and 934 (FIG. 9).

It is possible that some portion of a corrosion pit may be flat and perpendicular to the wavefront, so that a portion of the acoustic energy would be directly reflected back toward transducer face 204. This portion of the acoustic energy would travel along path 304 (FIG. 3, described above, in the Background of the Invention section), and would produce an echo signal in the same way as peak 936 (FIG. 9) was produced.

To discriminate what is a peak from what is a random noise spike, a "detection threshold" may be established. Any potential "peaks" which are smaller in magnitude than this threshold are ignored, in accordance with a preferred embodiment of the invention. In practice, it has been found that the "detection threshold" may advantageously be determined as midway between: (1) the noise level when no echo signals are present, and (2) the magnitude of the fifth echo in a multiple structure for uncorroded pipe.

This preferred threshold, as is evident from its definition, is a voltage which is derived empirically. The threshold's empirical derivation implies its calculation need not explicitly depend on such factors as excitation pulse magnitude, transducer characteristics, and attenuation of wavefronts in the liquid medium.

Figure 3:
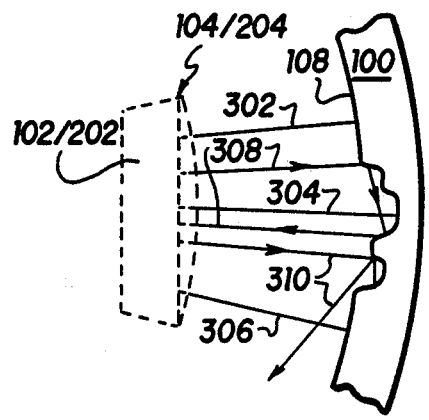
FIG. 3 represents a top plan view of the acoustic properties of an acoustic transducer when acoustic pulses are applied to a corroded tubular surface.

It is possible that the pit surface will cause acoustic energy to be finally reradiated in a direction which does not intersect the transducer face 204 at all. This eventuality is indicated as path 310 (FIG. 3, above). This loss of acoustic energy would be evidenced in a full waveform only by an apparent loss of total energy when integrating over the entire full echo waveform.

In practice, a very high correlation between pit *depth* and true depth has been observed using the above techniques. Pit depths can be determined to within a tolerance of 20 mils (0.02 inches), even for very convoluted surfaces.

b. Pit Area

The area of a given corrosion pit can also be determined from the echo waveform. Briefly, the pit area as a percentage of the transducer spot size area could be determined from the amount of acoustic energy which enters the pit as a fraction of the total acoustic energy incident upon the inner surface of the borehole tubular. However, not all the energy which enters a corrosion pit is reflected back to the transducer for detection, as was indicated in the discussion of FIG. 3. If the pit area measurement depended on the amount of energy reflected from the pit, the calculation of pit area would yield an incorrectly low value. A significant portion of the acoustic energy which enters a real-world corrosion pit is absorbed or deflected and never returns to the transducer for a reflected energy calculation.

It has been found that a much more reliable determination of pit area can be derived from the amount of acoustic energy which does *not* enter the pit. The amount of acoustic energy which does not enter the pit is, by implication, the acoustic energy which falls upon the uncorroded tubular surface. This energy which falls upon the uncorroded tubular surface is largely reflected back towards the transducer to be detected. That portion of the tubular surface which is uncorroded reflects incident acoustic waves with much more predictability than the pit surface. Therefore, the amount of reflected acoustic energy which the transducer receives from a tubular surface known to be corrosion-free provides an excellent gauge as to the maximum amount of energy which can be expected to be reflected from actual test surfaces. The amount of acoustic energy which is detected by the transducer at a time when a front surface echo is expected is therefore inversely related to the area of corrosion falling under the transducer's "spot."

The calculation of pit area $A_{pit}$ as a fraction of transducer spot size area $A_{spot}$ can be summarized as a calculation of 1.0 minus a quotient whose numerator is the measured magnitude of the front surface echo $H_{FSE}$, and whose denominator is the predetermined or precalculated magnitude of the front surface echo for a corrosion-free area of tubular $H_{FSE,O}$.

Symbolically, $$A_{pit} = (1.0 - H_{FSE}/H_{FSE,O}) * A_{spot}$$

The quotient represents the fraction of acoustic energy which is reflected from (and ideally was incident upon) the uncorroded surface. Subtracting this quotient from 1.0 therefore yields a fraction indicative of the remainder of the acoustic energy which, by implication, entered the pit and was *not* reflected in the front surface echo.

This pit area measurement technique directly measures only the area of corrosion within the transducer spot. The precise shape of the corrosion pit, (and, in some instances, *whether* there is more than one corrosion pit in the spot) is not determined. (The presence of plural pit surfaces is easily detected in most circumstances from analysis of the echos in the full waveform, provided the pit surfaces are at different depths.) But such determinations are not necessary in most practical applications, given the spot size (0.75×0.75 inches) and spot overlap capabilities of the preferred embodiment.

The denominator in the quotient (uncorroded front surface echo magnitude) may be determined by a variety of techniques. A single value may be determined either theoretically or empirically prior to a logging run. However, this method does not allow for any long-term differences in such parameters as tubular diameter and inadvertent decentering of the sonde within the tubular as it ascends. A variation in either of these parameters would cause a misleadingly large or small subsequent calculation of pit area.

Another method of calculating the maximum expected front surface magnitude is to continuously monitor what this maximum magnitude should be for uncorroded pipe at any given depth in the oil well. This maximum expected magnitude may be continuously redetermined based on, for example, a moving average (or a weighted moving average) of the most recently encountered front surface echos so as to give a continuously updated indication. Factors such as a deviation from true circularity of the tubular can be accounted for by considering only those previous front surface echo magnitudes which lie directly below the transducer spot presently under consideration. Allowance may also be made for the transition from one section of tubular to another through advance preparation for the transition, which transition may entail a measurable change in tubular diameter because of differences in diameters in different sections of tubular as they are manufactured, or misalignment as they are installed. Accounting for variations in such parameters lends itself readily to analysis by a rule-based system.

In practice, front surface echos are not always ideal in shape. Front surface echos are often distorted due to slight surface irregularities, called "surface roughness" for this discussion. Surface roughness may actually comprise the beginnings of a corrosion pit, but have caused so little deterioration in the surface that it cannot yet be called a corrosion pit. Surface roughness may cause a dispersion (decrease in magnitude and increase in width) of the front surface echo because of separate reflections from the imperfect surface, as was indicated in exaggerated form in the FIG. 3 corrosion pit.

In the case of surface roughness, two overlapping peaks may constitute the front surface echo. In this case, since all the acoustic energy arrives back at the transducer at a time when a front surface echo is expected, the magnitudes of any two peaks which occur in this time window should be added to obtain the numerator in the above quotient.

The question arises as to how to determine when an echo which is the second echo to arrive ceases to be a contribution to the front surface echo and begins to be a pit surface echo. Stated another way, the issue is how to determine when two adjacent peaks are overlapping, and when they are not overlapping.

Two peaks are defined to overlap when the time separation of the first and the second echo is less than the average width of the two echos. The width of echos in turn may be defined in terms of the width of the pulse envelope at the "detection threshold", described above, in the section entitled "Pit Depth".

When two echos overlap so as to conceal one lobe of the pulse envelope, the "edge" of the echo may be defined as the point closest to the peak at which there is a change in envelope slope polarity. A preferred method of implementing the determination of the edge of the echo pulse is described in greater detail below, in the section on Rule-Based Analysis of Full Echo Waveforms.

Less rigorous correlation has been observed with regard to the pit area measurement than with pit depth measurement, above. An uncertainty of approximately 30% of the spot size must be allowed in pit area determinations as described above. But given the small spot size (0.75×0.75 inches) in a preferred embodiment of the invention, as well as the fact that pit sizes smaller than the spot are indeed reliably detected, the improvement of the preferred embodiment of this invention over known systems is substantial.

3. Transmission of Full Echo Waveform Information

The acoustic information received by the transducer, in the form of a full echo waveform, must be transmitted to the means for analyzing the full echo waveform. This transmission of full echo waveform information may be accomplished as described in this section.

Figure 11:
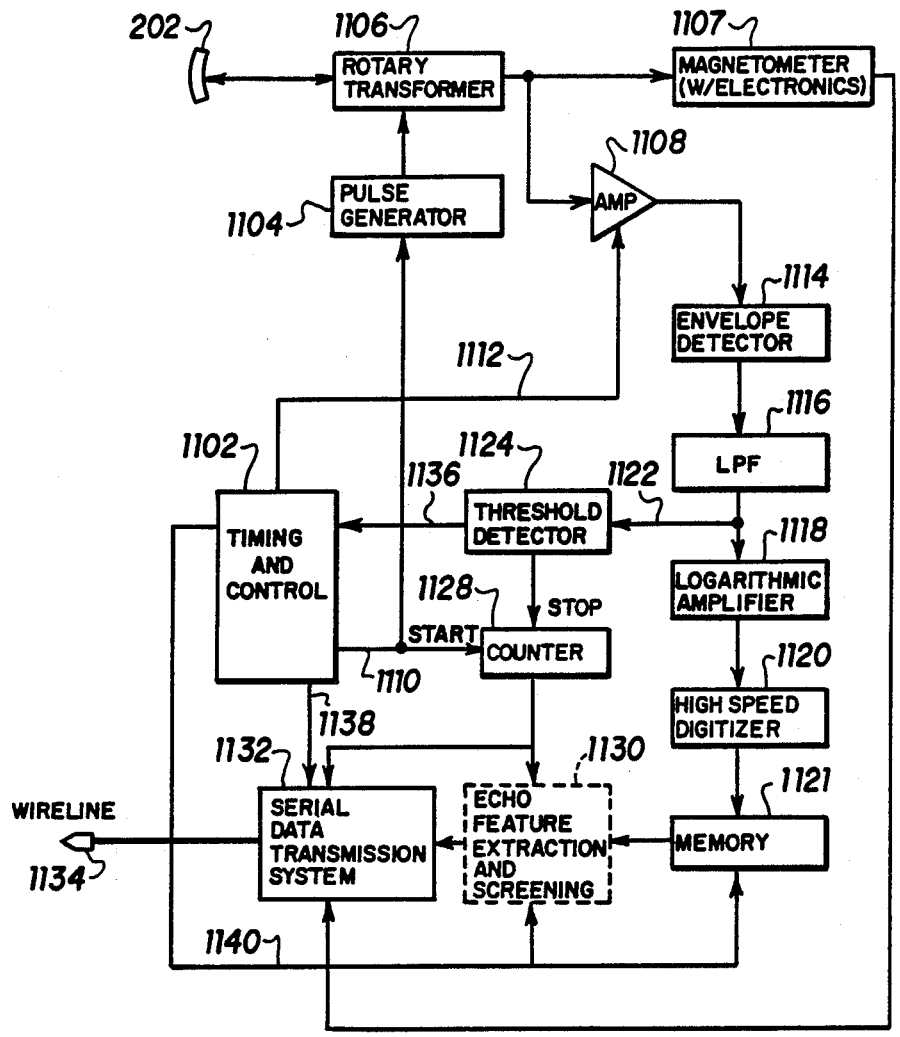
FIG. 11 is a block diagram of a preferred uphole transmission system used to transmit full echo waveform data (or extracted echo feature data) from a sonde to the rule based analysis system according to the preferred embodiment of the present invention.

Referring to FIG. 11, an uphole transmission system according to a preferred embodiment is presented in block diagram form. The illustrated uphole transmission system may be integrally connected with the means which produce the excitation pulse sequence which causes the full echo waveforms which are later analyzed.

Timing and control block 1102 emits a pulse generation signal on line 1110. The pulse generation signal on line 1110 travels to pulse generator 1104 for the generation of the short-duration, high-magnitude excitation pulse which is sent through rotary transformer 1106 to curved transducer 202. Rotary transformer 1106, known in the art, makes the bidirectional electrical connection between the transducer and the remainder of the downhole circuitry. The pulse generation signal on line 1110 is also input to the start input of counter 1128, whose purpose and function will be described below.

A motor causes both rotary transformer 1106 and transducer 202 to rotate as the entire sonde is drawn up the tubular. A magnetometer 1107 with associated electronics of a type known in the art emits a signal once per revolution. This signal is sent uphole on the wireline 1134, advantageously being sent in coordination with the full echo waveform information, through a serial data transmission system 1132. The coordination of the signal from the magnetometer 1107 with the full echo waveform information allows verification of the vertical alignment of spots on successive passes. It can also provide absolute directional orientation information. For an example of a known rotary transformer and magnetometer arrangement, see U.S. Pat. No. 3,503,038 to Baldwin.

As described above, in the section entitled "Generation of Full Echo Waveform," transducer 202 emits an acoustic pulse which strikes, and is reflected from, a target surface such as an oil well borehole tubular. The transducer senses the set of echos which comprise the full echo waveform and communicates this information in the form of an analog voltage through rotary transformer 1106 to variable-gain amplifier 1108.

The full echo waveform is passed to the timing and control block 1102 via lines 1122 and 1136. Within the timing and control block 1102, an automatic gain control circuit, (AGC) detects the peak amplitude of the wave and generates a gain control signal. The AGC circuit insures that the output from variable gain amplifier 1108 does not fall outside of the dynamic range of envelope detector 1114. The AGC circuit also insures that a waveform of relatively constant peak amplitude is applied to the input of envelope detector 1114. AGC circuitry is well known to those skilled in the art.

Timing and control block 1102 controls the gain of variable-gain amplifier 1108 by sending a gain control signal along line 1112. Advantageously, timing and control block 1102 produces a gain signal on line 1112 so that the amplifier makes full use of its dynamic range without clipping the signal input to it from rotary transformer 1106.

Line 1138 is used to send a digitized value for the gain control signal, as applied to variable-gain amplifier 1108, to the serial data transmission system 1132, where it is multiplexed with other data to be sent to the surface. This value is later used to convert the transmitted waveform voltages back to the original signal values that appeared at the input of variable gain amplifier 1108. Where the optional Echo Feature Extraction and screening block 1130 is used, the digitized gain control signal may instead be applied to block 1130 for downhole preprocessing.

The full echo waveform thus gain-adjusted is input to envelope detector 1114. In a preferred embodiment this envelope detector 1114 has a dynamic range of 60–80 dB, so that even very small peaks in the waveforms are preserved. Envelope detector 1114 effectively reduces the bandwidth of the substantially sinusoidal full echo waveform from amplifier 1108 to a monopolar waveform of substantially lower bandwidth. In a preferred embodiment, the received ultrasonic echos comprise short pulses of approximately 5 MHz center frequency. By rectifying the oscillatory pulses and smoothing the envelope-detected signal with the low-pass filter 1116, the bandwidth is reduced to approximately 2 MHz.

The smoothed monopolar full echo waveform is next input to logarithmic amplifier 1118 to reduce the effective dynamic range of values of the full echo waveform magnitude so as to optimize the use of the wireline transmission data and to ensure maximum resolution capabilities of high-speed digitizer 1120, which receives its output. Typically, the 80 dB range of envelope detector 1114 is reduced to the approximately 40 dB range of an 8-bit digitizer advantageously employed as element 1120. High-speed digitizer 1120 converts the logarithmically compressed, smoothed monopolar full echo waveform from its analog representation to a digital representation. Preferably, digitizer 1120 operates at a 5 MHz sampling rate, so that an average echo pulse encompasses about five samples.

The digitized, logarithmically compressed, smoothed monopolar full echo waveform is stored in a memory 1121 which receives the output of digitizer 1120. Advantageously, memory 1121 is a recirculating memory which continuously stores the digitized information. (The control of the memory 1121 is accomplished by the arrangement of the timing and control block 1102 and threshold detector 1124, described in greater detail below.) The memory 1121 has enough storage locations to store slightly more than the amount of data comprising one full echo waveform. The continuous storage of data from digitizer 1120 is halted at a time determined by the arbitrarily chosen "end" of the full echo waveform (an interval usually on the order of 20 microseconds, as indicated in element 706 of FIG. 7). What remains in memory 1121 when storage is halted is thus a digitized full echo waveform, including data from a small amount of "lead time" before the full echo waveform, due to the slight oversizing of the memory. It is the information in this digital representation of the full echo waveform, "frozen" in circulating memory 1121, which is transmitted uphole.

This digital representation of the full echo waveform may be transmitted uphole in at least two forms, depending on the degree of sophistication of the downhole electronics. The echo feature extraction block 1130 is indicated in dashed lines to indicate the choice which the designer has in including or omitting it before transmitting the information uphole.

In a first, preferred embodiment, echo feature extraction and screening block 1130 is present. Under control of the timing and control block 1140 block 1130 analyzes the waveform digitally according to principles presented below, in the discussion related to FIGS. 12 and 13. In this embodiment, information as to the quantity of echos in a given full echo waveform, as well as the height, width, and "location" (time of occurrence) of each echo in the waveform, is transmitted uphole. Also, waveforms which are clearly characteristic of an uncorroded tubular may be screened out downhole, so as to optimize the long-term utilization of available transmission bandwidth. After being transmitted uphole, the extracted echo features may be analyzed by the rule-based system according to a preferred embodiment of the present invention.

The first embodiment just described presumes a fair degree of computational sophistication to be inherent in the sonde body. This embodiment could be implemented using microprocessor or special purpose electronics technology well within the ability of one of ordinary skill, upon a reading of the text related to FIGS. 12 and 13.

In a second, alternative embodiment, the raw samples of the full echo waveform temporarily frozen in memory 1121 may be immediately transmitted uphole so that the echo feature extraction method and screening function may be performed there, perhaps by the same computer which executes the rules of the rule-based system. In the second embodiment, echo feature extraction and screening block 1130 is not present, and the digitized full echo waveform frozen in memory 1121 is sent via serial data transmission system 1132 up the wire line 1134 without the echo height, width, and location first being extracted.

After the digitized full echo waveform has been read from memory 1121, timing and control block 1102 sends a restart signal to the memory 1121. The restart signal "unfreezes" the circulating memory so that it begins to continuously store new digitized waveform information from digitizer 1120 in preparation for the next full echo waveform.

In the first embodiment, the restart signal is generated after echo feature extraction and screening block 1130 has finished reading the current digitized full echo waveform from the memory for analysis. In the second embodiment, the restart signal is generated after the serial data transmission system has read the raw digitized full echo waveform for transmission uphole.

Timing and control block 1102 is advantageously constructed of a microprocessor, but may also be implemented using large-scale integrated circuit (LSI) hardware. A hybrid of microprocessor, LSI and discrete components also lies within the scope of the present invention. Advantageously, the same processor hardware which implements the timing and control circuit 1102 may also execute the same functions as echo feature extraction and screening block 1130.

Generally, the functions performed within the echo feature extraction and screening block 1130 are more complex and timewise demanding than those functions performed within timing and control block 1102. Timing and control block 1102 serves the main purposes of the comparatively long-duration timing functions, such as generating the excitation pulses on line 1110 or the choice of the gain factor on line 1112. Block 1102 also performs the timing delay measurement commenced upon receipt of an input signal from threshold detector 1124 so as to produce signals which "freeze" and "unfreeze" the contents of memory 1121. The ability to implement these functions using existing technology lies well within the scope of one of ordinary skill, and will not be discussed further.

Referring again to FIG. 11, the following discussion describes the interaction of timing and control block 1102, threshold detector 1124, and counter 1128 with the blocks already described. The main purpose of threshold detector 1124 and counter 1128 are to ensure that only the full echo waveform itself is sent uphole, and not the generallY flat signal before it. Referring briefly to FIG. 7, there is a delay on the order of (in one particular example) 60 microseconds between the excitation pulse 702 and the earliest possible arrival time of an echo from the target surface. During this time, no meaningful information could be received from the transducer so that its output (and the output of digitizer 1120) should be ignored by serial data transmission system 1132. It is only during the time of the full echo waveform 706 that meaningful information can be received from the transducer.

In operation, timing and control block 1102 (FIG. 11) sends a pulse generation signal along line 1110 to start counter 1128 counting. Counter 1128 counts so as to measure the time interval between the pulse generation signal (which creates the excitation pulse) and the time when the first echo rises above a threshold. The time when this first echo rises above a threshold is determined by threshold detector 1124 upon analysis of the smoothed monopolar full echo waveform input to it along line 1122 from low pass filter 1116. The threshold detector output stops counter 1128 at a time when the useful information has started to be received. The value of counter 1128 at this time thus marks the time of the first-received echo in relation to the original excitation pulse.

This information from counter 1128 is useful in determining, in real terms, how far away from the transducer the nearest portion of the target surface was. The threshold detector's signal indicates that the period of useful information on the full echo waveform has begun. Time period 706 (FIG. 7) indicates this period of useful information to be approximately 20 microseconds.

Regardless of which embodiment is chosen (reflecting the inclusion, or exclusion, of the echo feature extraction and screening block 1130 in the downhole electronics), the information reflecting the delay between the excitation pulse and the rising of the first returned echo above the threshold must be transmitted uphole. If the first embodiment is employed (echo feature extraction and screening block 1130 being present downhole), then the value of counter 1128 is effectively incorporated into the location and data entries output from echo feature extraction block 1130. If the second embodiment is employed (echo feature extraction and screening block 1130 being uphole), then the value of counter 1128 is multiplexed with the raw digitized full echo waveform information passed directly from digitizer 1120 to the serial data transmission system 1132.

Serial data transmission system 1122 involves communications apparatus, and modulation and multiplexing schemes which are within the ability of one of ordinary skill in the art. See, for example, U.S. Pat. No. 4,415,895 to Flagg, entitled "Well Logging Transmission System." The ability to perform the uphole transmission of full echo waveform data, in whatever form, is within the ability of one of ordinary skill, reference being made to the present discussion and the related discussions referenced within it.

As described above in the section on Bandwidth Reduction, the present invention utilizes an amount of bandwidth which is much smaller than would be used by known systems, for a given requirement as to minimum-sized detectable corrosion pit. Thus, for a given bandwidth restriction imposed on the downhole-uphole comaunications channel and a given minimum detectable corrosion pit size, the use of the present invention's larger transducer size and optional downhole echo feature extraction and screening functions allows more rapid coverage of the tubular surface than would have been possible by using the smaller transducer necessitated by use of the known system described in the Background of the Invention section.

Standard transmission methods may be employed. If the transmission bandwidth imposed by the physical configuration of the downhole-uphole transmission channel proves a burdensome limitation, various parameters may be changed so that the desired amount of information may be transmitted uphole. For example, the logging rate L may be reduced, perhaps in conjunction with a reduction in the excitation pulse frequency F. Also, the frequency at which the analog full echo waveform is sampled could be reduced so that, in the embodiment in which the raw digitized samples are transmitted uphole, an effective reduction in the amount of data may be achieved.

Alternatively, if the extracted echo features are the information which is actually transmitted uphole, the threshold below which echos are to be ignored may be raised, so that, statistically, less information will have to be transmitted uphole. Of course, any of these methods of reducing the amount of bandwidth will compromise some other performance feature, such as downtime of the oil well (because of a slower logging rate), or reduced sensitivity to smaller corrosion pits (due to raising of the threshold). Arbitration among these various competing factors is well within the ability of one of ordinary skill in the art and will not be detailed further here.

4. Rule-Based Analysis of Full Echo Waveforms

What follows is a description of the preferred embodiment of the rule-based system which reliably and automatically analyzes and interprets the sampled full echo waveforms returned from the transducer.

a. Terminology

The following table is offered to present to the reader the meaning of various terms which will be used throughout the discussion of the rule-based system according to a preferred embodiment of the present invention.

TABLE 1

List of Terms Used to Describe Echos and Echo Structures

| Term | Definition |
|---|---|
| Signal | Response of sensor (transducer) for a single location with respect to the pipe tubular wall. Composed of a series of echos at various times. Signal contains information on corrosion only over a localized area on the pipe (typically ¼" by ¼") equal to the "spot area". |
| Echo | A distinct portion of the signal characterized by a rapid increase in values with time, a peak value, and a following rapid decay in value. |
| Echo Location | Index (e.g. "sample #26") of the peak value within the echo. The term implies a "location" in time, not physical location on the target surface. |
| Echo Height | Maximum value within echo width. |
| Echo Width | The number of sample points between the start and end samples of the echo as defined by the echo extraction program. |
| Pit | A surface of the inner pipe wall which is deeper than the uncorroded surface. There can be several pits identified from one signal. |
| Front Surface Echo | An echo which is generated by a reflection from the first surface encountered by the ultrasonic signal. This echo will be generated by the uncorroded inner-surface except in the case where an area larger than the spot size is corroded away. |
| Leading Echo | An echo which is the first echo in a multiple structure. It is generated by the front side of the surface causing the multiple structure. |
| Dominant Echo | A "dominant echo" must be some factor (typically 2) larger in value than any other echo. |
| Multiple Structure | A multiple structure is characterized by a "strong" leading echo followed by a series of echos with successively lower values at locations which are separated by a fixed time (sample) interval. |
| Neighbor Echo | Echo #1 is a neighbor of echo #2 if there is no other echo between these two. |
| Spurious Echo | A spurious echo is one that has been generated by some process which is unknown and for which there is no prior information. Most of these are caused by interference of the signals at a surface (peak splitting). They are not pertinent to the interpretation, are normally small and should not be identified as pit echos. |
| Structure | A set of echos having physical and/or acoustical significance (e.g., a multiple structure, front surface echo, pit echo, etc.). | b. General Introduction to Artificial Intelligence (AI)

The general concept of a rule-based system is known in the art. Such systems fall under the general description of "artificial intelligence" systems. The term "artificial intelligence" reflects the fact that AI systems emulate the conscious (and perhaps subconscious) reasoning process actually occurring in the mind of a human expert.

Generally, expert systems are conceived as comprising three major components: the knowledge base (including knowledge sources and a "blackboard"); an inference engine; and a user interface.

The knowledge base comprises the raw declarative and procedural knowledge of a human expert. The procedural knowledge takes the form of "rules". Each rule comprises a set of "IF" conditions and a set of corresponding "THEN" action statements. When all of the "IF" conditions are satisfied, based on analysis of the declarative knowledge (or "blackboard"), then the inference engine may cause the rule to "fire" (be executed). When a rule is fired, the "THEN" actions are performed by the computer, usually resulting in a change of state of some information on the blackboard. Thus, during the operation of the expert system, the amount and nature of knowledge on the blackboard will change.

The second major component of an expert system is the inference engine. As the term "engine" implies, the inference engine is the motive force which actively uses the facts (declarative knowledge) and the rules (procedural knowledge) to arrive at a solution to the problem at hand. Very basically, the inference engine is that part of the expert system that determines which, if any, of the rules have their "IF" conditions met. Based on some predetermined criterion, such as the number of "IF" conditions present in the rule, the inference engine decides which one of rules, all of whose "IF" conditions are met, is fired next. That one rule is said to have "priority".

The third major component of an expert system is the user interface. Briefly, the user interface is the means by which humans communicate with the expert system. More exotic embodiments of user interfaces may be artificial intelligence systems in and of themselves. User interfaces may comprise such "input" (sensory) functions as speech recognition and computer vision (pattern recognition). User interfaces may also comprise such "output" (expressive) functions as speech synthesis.

According to the preferred embodiment of the present invention, it is the knowledge base (the knowledge sources plus the blackboard on which they operate) which is the focus of discussion. A standard inference engine, such as that present in the rule-based programming language OPS5 (available from Digital Equipment Corporation, Maynard, Mass.), may be employed. Also, less exotic embodiments of user interfaces are employed in the preferred embodiment, as will be seen below. However, it is to be understood that other variations of the components of expert systems, whether they be now known or hereafter developed, lie within the contemplation of the present invention.

According to a preferred embodiment of the rule-based approach of the present invention, "forward chaining" of rules is used. That is, conclusions about echo identity and pit characteristics are made on the basis of signal features of the sampled full echo waveform. Initial numeric constraints in the blackboard, as well as various predetermined control functions, determine which rules are activated at any given time.

The rule-based approach to problem solving has two primary advantages over sequential programming techniques. First, the execution of the program is opportunistic, rather than sequential. Processing speed is thereby increased, since no time is consumed as the processor steps through logical tests which do not apply to the present situation. Second, the rules of the expert system according to the present invention are modular, and may be easily modified without changing large amounts of preexisting code. The program can be built up incrementally, simply by adding more rules.

The rule-based system according to a preferred embodiment of the present invention is implemented in OPS5. OPS5 was chosen because it is well suited for forward-chaining. See Brownstone et al., *Programming Expert Systems in OPS5*, Addison-Wesley, Reading, Mass., 1985. The knowledge base according to the preferred embodiment of the present invention may be more easily understood with reference to any of various publications on the general topic. See generally, Rich, *Artificial Intelligence*. McGraw-Hill, Inc., 1983). For a description of the more specific concept of "blackboard systems", see Nii, "Blackboard Systems: The Blackboard Model of Problem Solving and the Evolution of Blackboard Architectures," Part I, *The AI Magazine*, Summer, 1986; "Blackboard Systems, Blackboard Application Systems, Blackboard Systems from a Knowledge Engineering Perspective," Part II, *The AI Magazine*, August, 1986. For a description of an expert system directed toward machine analysis of acoustical signals, see Maksym et al., "Machine Analysis of Acoustical Signals," *Pattern Recognition*, Vol. 16, No. 6, 1983.

c. Overall Software Flow

Figure 12:
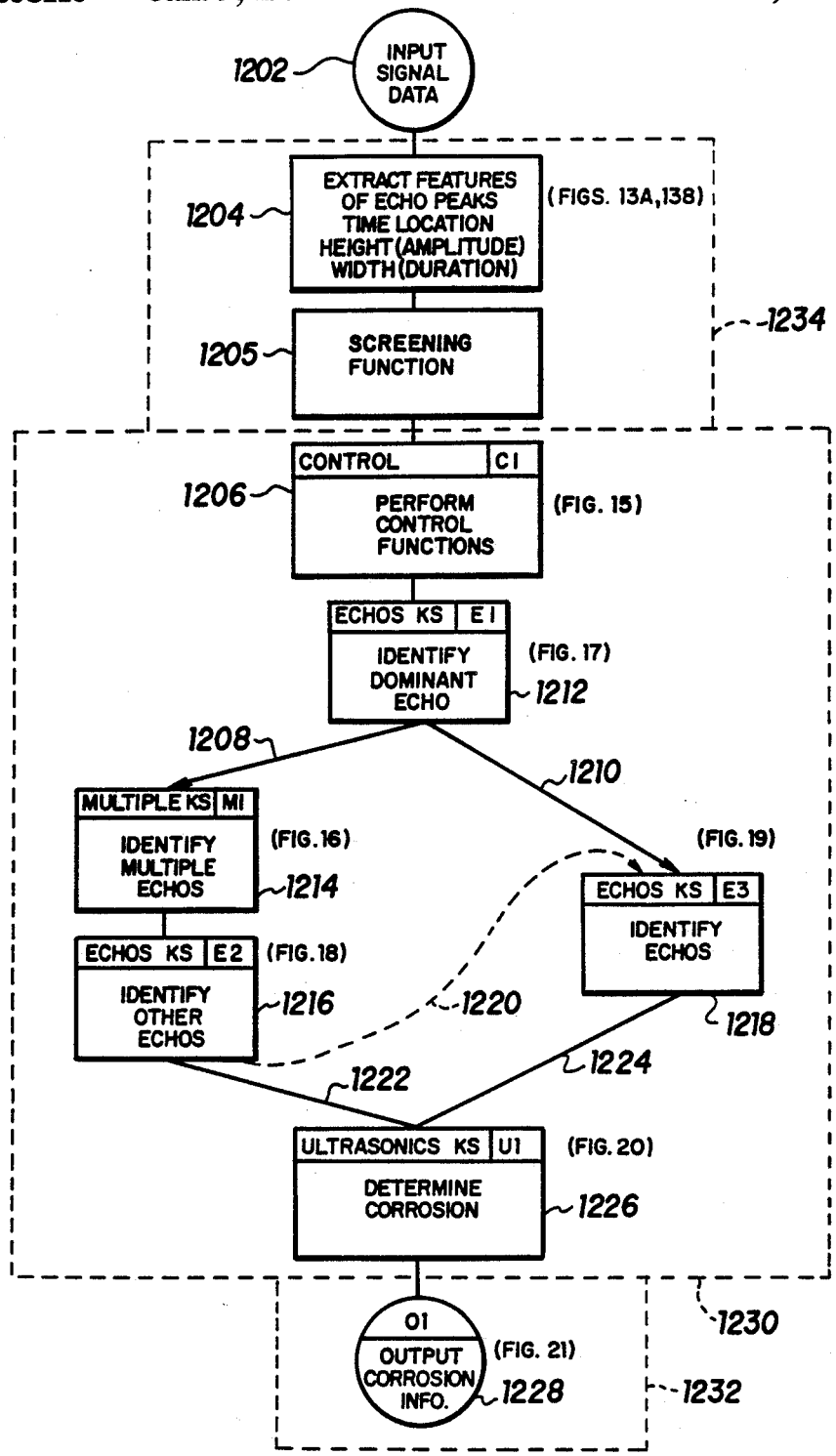
FIG. 12 is a flow diagram illustrating in very general form the relation of knowledge sources in the rule-based system according to the preferred embodiment of the present invention.

The flow diagram for the system is shown in FIG. 12. Each of the rule-based modules is marked with a symbol (C1, E1, E2, E3, M1, U1) that refers to a connection point in later figures (FIGS. 15-20).

Processing begins with the input of sampled waveform values from a file. The first module 1204 extracts specific features of the waveform which are used by the knowledge sources. The height, width and location (in samples) of each echo peak are determined. Echo peaks of height (amplitude) below a set threshold are ignored.

Screening function 1205 eliminates from further consideration the vast majority of waveforms in which there is no trace of structures which could have been caused by corrosion. Such a screening function could eliminate from consideration those waveforms in which a large echo is followed by a single sequence of properly spaced echos, and in which no other echos are present. What echo spacing was deemed "proper" would be determined by the nominal thickness of the tubular, since the spacing of echos in a multiple structure is determined by the two-way travel time of an acoustic pulse between the tubular's inner and outer surfaces. Advantageously, a certain tolerance (e.g. 5 percent of the nominal interpulse spacing) is allowed for the slight irregularities of measured echo spacing to be expected even in a perfectly uncorroded area of tubular.

Advantageously, this screening function may be performed by a streamlined, sequential (non-rule-based) program module, since it is so specialized in nature. However, it is to be understood that this screening module 1205, as well as the echo feature extraction module 1204, could also be implemented using non-sequential, rule-based software.

In FIG. 12, box 1230 surrounds those modules which, in a preferred embodiment, are implemented in rule-based software. Box 1232 surrounds those modules which could be implemented in rule-based software, even though they are preferably implemented with sequential programming techniques. Box 1232 indicates the extension of rule-based software to the User Interface in the interactive output of corrosion information, described below.

In a preferred embodiment, modules 1204 and 1205 are executed downhole, so as to minimize the amount of data that must be transmitted uphole on a wireline communications channel of necessarily limited bandwidth. Of course, one or both of these modules could be executed uphole, perhaps in the same computer which executes the rule-based software in boxes 1230 and 1232.

Control functions are applied at 1206 which direct the application of the knowledge sources to working memory elements.

The ECHOS Knowledge Source (KS) determines at 1212 wether there is present a "dominant echo" (defined in Table 1). Depending on the conclusion reached by the ECHOS KS at 1212, rule activation can follow two paths.

A left path 1208 is taken when the echo features indicate the presence of a dominant echo (and therefore, probably a multiple structure) in the signal. All multiples, the front-surface echo, and any pit echos are identified using the "MULTIPLES" and "ECHOS" knowledge sources at 1214 and 1216. When all echos have been identified, the ULTRASONICS KS determines at 1226 the corrosion characteristics.

If no dominant echos are found, then control passes along the right path 1210 (FIG. 12) so that the ECHOS KS (E3) at 1218 identifies echos when no multiple structure has been found. Again, when all echos are identified the ULTRASONICS KS takes over at 1226.

Execution terminates after the corrosion information is output at 1228. The system is initialized for the next signal.

Although FIG. 12 would appear to indicate sequential processing, the system is highly opportunistic. For example, should the processing along left branch fail to identify a multiple structure, the rules on the right branch would automatically take over, as indicated by dotted line 1220. Likewise, if the initial conditions for a possible multiple structure are not present in the input features, none of the rules involved with multiples would be activated.

i. Echo Feature Extraction

The extraction of echo features (height, width, and location) may be performed for each echo in each signal using a sequential (e.g., Fortran) program. A flow chart for the program is shown in FIG. 13A.

The sampled data is read from an input file at 1302 and the echo features are determined and eventually written to an output file at 1308. The output file is then read by the rule-based program.

Figure 13A:
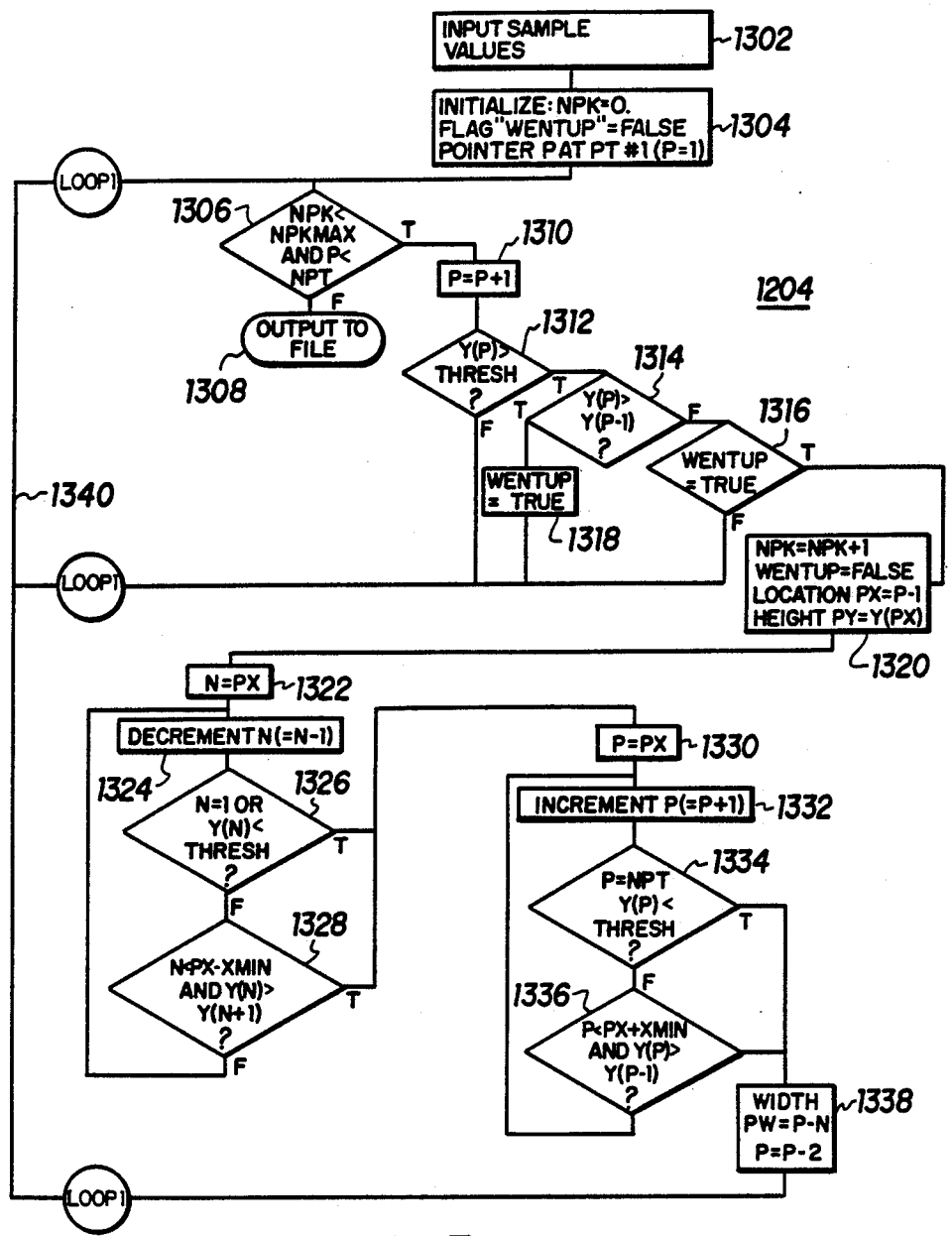
FIG. 13A is a flow chart illustrating the echo feature extraction routine according to the preferred embodiment of the "Extract Features . . . " block in FIG. 12.
Figure 13B:
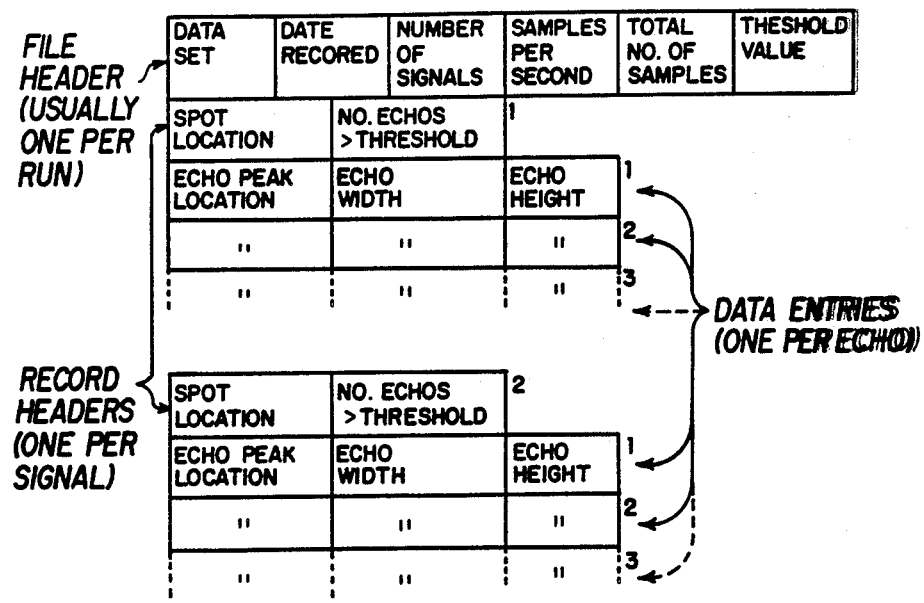
FIG. 13B illustrates a preferred data file structure produced by the echo feature extraction routine diagrammed in FIG. 13A.

The symbols used in FIG. 13A are defined as follows:

| INPUTS: | |
|---|---|
| NPT | Number of points in the waveform. |
| Y(1 to NPTS) | Array of waveform magnitudes at each sample point) |
| THRESH | Threshold below which peaks are ignored. (0 < THRESH < largest Y) |
| XMIN | Criteria used to find WIDTH. Value is a given number of points. Default=3. |
| NPKMAX | Maximum number of peaks to be found (< or = to NPT) |
| OUTPUTS: | |
| NPK | Number of peaks found in the waveform. Will be < or = to NPKMAX. |
| PX(1 to NPK) | LOCATION. Value is a sample index (from 2 to NPTS-1). |
| PY(1 to NPK) | HEIGHT = Y at location PX(i): i = 1 to NPK |
| PW(1 to NPK) | WIDTH in sample points = P - N. N & P are found as follows. |
| N (Neg. pointer) | starts at peak then moves to lower sample indexes until (1) or (2) is true: (1) Y(N) < THRESH or N is at first point (N = 1) |
| or | (2) N is at least XMIN pts from peak XMIN < PX- N AND value has started increasing Y(N) > Y(N-1) |
| P (Pos. pointer) | starts at peak then moves to higher sample indexes until (1) or (2) is true: (1) Y(P) < THRESH, or P is at last point (P = NPT) |
| or | (2) P is at least XMIN pts from peak XMIN < P - PX AND value has started increasing Y(P) > Y(P-1) |

The detection of a peak is based upon a change from positive to negative in the local slope of the values. For a valid peak, the amplitude must exceed a threshold value. This value is typically set to a value midway between the height of the fifth multiple echo and the background noise level when no corrosion is present.

Once a peak is detected, the amplitude at the peak (height) and the location index (sample#) are stored in an array. In a preferred embodiment, the peak width is obtained by marching down the sides of the peak and looking for either of two conditions to be met. The edge of the peak is found when (1) a sample value is below the threshold, *or* (2) a slope change occurs. The width of a peak is taken to be the difference in sample number between its two edges. The routine ends when the array values have been output to a file.

The following is a detailed description of FIG. 13A for Echo Feature Extraction.

The sample values are input from a file as shown by block 1302. Once these values have been input to the program, certain flags and pointers are initialized in block 1304. The number of peaks found in the waveform, NPK, is first set to zero. In addition, flag "WENT-UP" is initialized to false and the positive pointer "P," the index on the current sample value, is set to 1.

The routine then enters the loop indicated by LOOP 1. The test in block 1306 determines if the number of peaks found, NPK, is less than the maximum number of peaks to be found, and if the positive pointer is less than the total number of points in the waveform, NPT. The maximum number of peaks to be found is initially set to the total number of points in the waveform. If this logical test is false, the program immediately outputs all values for the echo attributes to a file in the format described below. If this logical test is true, then the positive pointer on the sample index is incremented by one.

The set of logical tests 1312, 1314 and 1316 are used in the detection of an echo peak. The test indicated by block 1312 determines if the next value Y(P) in the sample data is greater than the given threshold. If this is false, then the program immediately goes to LOOP 1 so that the next sample value can be considered. If the test is true, the program branches to 1314, where a test is made to determine if the new sample value Y(P) is greater than the previous sample value. If this is true, then the flag "WENT-UP" is set to true and branch is made back to LOOP 1. If the test is false, then the flag is tested in 1316. If the flag "WENT-UP" was false at the time of the test indicated in 1314, then a branch is made, again, to LOOP 1.

If the flag "WENT-UP" was equal to true in 1316, several other program variables in block 1320 are initialized and the lower portion of the figure is entered. This means that a new peak has been detected in the signal because the slope of the sampled data changed from positive to negative. Block 1320 increments the counter on the number of peaks found, NPK. In addition, the flag "WENT-UP" is set to false. The location for the new peak in the signal is set to the previous pointer "P" minus one sample index, and the height of this peak PY is set to the value at index PX.

The next step is to set "N," the pointer for the negative direction, equal to the index for the peak. In this lower section of the figure, the pointers begin at the index of the peak and march down both sides of the peak in order to determine the width of the echo just identified.

First, the negative pointer "N" is decremented in 1324. The logical test in 1326 determines if N=1 or if the value at the new negative pointer is less than the threshold. If N=1, then we have progressed to the left to the very beginning of the echo waveform. If the second part of the test is true, then a left edge of this identified echo has been identified. Thus, if N=1 or the second condition is true, we branch to the lower right side of the figure where a right-hand edge is identified. If condition 1326 is false, the following test in 1328 detrrmines if the left-hand, or low-time, edge of the echo can be identified by a change in slope in the signal. This test handles the case where the left edge of the echo does not cross the threshold but rather encounters another peak to the left of the current peak.

To separately identify these peaks, test 1328 tests if the slope going down the left side of the echo changes to a positive slope. If no change in slope is indicated, the logical test fails and we return to block 1324. Here the negative index N is decremented again to consider points further to the left of the current index. Should either logical test 1326 or 1328 be true, then the left-hand edge of the echo has been discovered, and a search for the right-hand point, or high-time point, is then initiated.

For the identification of the right-hand point, the first step is to set the positive pointer index (PX) equal to the location of the peak value (block 1330). A loop is then entered which is identical to that previously described for the negative pointer. Block 1332 successively increments the pointer to look at values at increasing time on the right side of the peak. As in the case for the left-hand edge of the echo, blocks 1334 and 1336 are used to identify the right-hand side of the peak. In this case, the right edge of the echo is identified by a threshold crossing, or a change in slope for successive sample values from negative to positive. If either of these conditions are true, then the right-most edge of the echo has been determined. If both of the conditions are false, the positive pointer is incremented again to consider the next sample value.

Once the right edge of the echo has been determined, the width for the echo is calculated in 1338 as the difference between the positive pointer P and the negative pointer N. In addition, the pointer for the current location in the sample data is set to an index two (2) lower than the rightmost edge of the echo. LOOP 1 is entered again and execution goes back to logical test 1306.

This process continues until all peaks in the signal have been identified and their left- and right-most edges determined. Logical test 1306 tests for the case where the index P is equal to the total number of points in the waveform. At this point, all the echo attributes for peak value, width and location are output to a file and the process terminates.

This ends the detailed discussion of FIG. 13A.

The preferred output file has a file header line (shown in FIG. 13B) which contains: (1) a description of the data set, (2) the date recorded, (3) the number of signals, (4) the number of samples/second. (5) the total number of samples, and (6) the threshold value.

Each sampled signal in the output file has a record header (shown in FIG. 13B) containing data on the location of the spot area on the pipe and the number of echos in the signal which exceed the threshold. Following the header are data entries, each comprising the sample location for the peak echo value, the echo width in samples, and the height (peak digitized voltage value).

The data file thus arranged is ready for analysis by the rule-based analysis system, generally indicated at 1230/1232 (FIG. 12), possibly after records are selectively eliminated by screening function 1205 (FIG. 12).

ii. Initialization and Constraints

When the rule-based system is run, the element classes of working memory ("blackboard") are defined. Once defined, no additional element *classes* can be defined, but any number of working memory *elements* of a given class can be created or modified.

Table 2 shows the element classes and associated attributes used for the system according to the preferred embodiment. For example, the class "echo" (the third entry in Table 2) has 10 attributes (signum echo_num width loc . . . ) which are used to describe individual echos. There is one working memory element of class "echo" for each echo. Each such working memory element has the same pattern as that indicated in Table 2.

TABLE 2

Working Memory Element-Classes and Attributes

| ELEMENT CLASS | ELEMENT ATTRIBUTES |
|---|---|
| signal_set | name date numsig usec/samp numsam threshold x_offset y_offset |
| signal | signum num_of_echos xang ydist max_loc max_height |
| echo | signum echo_num width loc height type status tag multiple_of mark |
| pit | signumber type pitnum depth area osig match depth_match xcen ycen xlow xhigh ylow yhigh |
| control | name status |
| question | name asked answer |
| constraint | name value tag |
| computed | name value |
| dom_echo | signum echo_num loc |
| structure | type generator_num number f_mult status mult_list |
| task | name data1 data2 |
| counter | name count |
| plot | term_type status |
| cur_echo | signum echo_num loc |
| diff_echo | signum ech_1 ech_2 diff offset h_ratio |
| limits | lower upper exact |
| overlap | ech_1 ech_2 lowlim uplim |
| corrosion | type echo_num depth size |

Description of the Attributes

| | |
|---|---|
| SIGNAL SET | One WME with information on measurement parameters from input file |
| name | Identifier for data set containing features of sampled signal |
| date | Date on which sampled data recorded |
| numsig | Number of individual signals in the input file |
| usec/samp | The time interval between sampled values in microseconds |
| numsam | The fixed number of sampled values for each signal |
| threshold | Height below which sampled data values are ignored |
| x_offset | Scan parameter for the circumferential distance between spots |
| y_offset | Scan parameter for the vertical distance between spot areas |
| SIGNAL | WME's of this class hold information on each signal in set |
| signum | The number of a particular signal (1 to numsig) |
| num_of_echos | The number of distinct echos identified in the signal |
| xang | Angular offset of spot center from north on pipe |
| ydist | Depth location of spot center on pipe |
| max_loc | Maximum index value for signal data (=numsam) |
| max_height | Value of height for largest echo |
| ECHO | WME's of this class holds information on echo features and type |
| signum | Signal number to which the echo WME belongs |
| echo_num | The number of the echo (1 to num_of_echos) |
| width | Width feature for the echo (number of samples see features) |
| loc | Location of the echo peak (sample index - 1 to numsam) |
| height | Value of the sampled data at location of echo peak |
| type | Identity of the echo (e.g. pit, front-surface, spurious, etc.) |
| status | Flag for echo plotting by the user-interface |
| tag | If the echo is a multiple, the tag is set to the first echo number |
| mark | Flag used to indicate that the width of the echo has been counted |

TABLE 2-continued
Working Memory Element-Classes and Attributes

| ELEMENT CLASS | ELEMENT ATTRIBUTES |
|---|---|
| PIT | WME to hold information on identified pits |
| signum | The number of a particular signal for which a pit has been found |
| type | Type of pit (e.g., pit within multiple) |
| pitnum | Echo number which indicates presence of pit |
| depth | Depth of pit as found using rules in Ultrasonics KS |
| area | Area of pit as found using rules in Ultrasonics KS |
| xcen | Circumferential location of spot (pit) on pipe |
| ycen | Vertical location of spot (pit) on pipe |
| CONTROL | These WME's are used to control the activation of some rules |
| name | The specific type of control WME (e.g., signal_done ?) |
| status | Flag to indicate status for the control function (Typ. yes/no) |
| QUESTION | These WME's hold process information from the user interface |
| name | Particular question asked |
| asked | Flag to indicate if the question has been asked yet |
| answer | The answer provided by the user |
| CONSTRAINT | These WMEs hold information on physical and measurement variables |
| name | Constraint type (e.g., "pipe_inner_cir" for pipe inner circumference) |
| value | Current value of the constraint |
| tag | Flag used to indicate status of updates for constraint values |
| COMPUTED | This class holds temporary calculated values for each signal |
| name | The name for the value computed by the rule |
| value | The stored value |
| DOM ECHO | A single WME of each signal which identifies the dominant echo |
| signum | The signal number for which the echo is dominant |
| echo_num | The number of the echo which is the dominant echo for the signal |
| loc | The index for the peak value of the echo (same as "loc" above) |
| STRUCTURE | WME class to hold information on identified structures in signal |
| type | Type of structure identified (e.g. "Multiple") |
| generator_num | The number of the echo giving rise to the structure |
| number | Number of echos involved in a "multiple" structure (only) |
| f_mult | The echo number for the first multiple in a "multiple" structure |
| status | Flag to indicate that the labeling of multiple echos is complete |
| mult_list | Array of values holding the echo numbers for each multiple |
| TASK | These WME's focus attention to specific tasks (removed when done) |
| name | The task name ("get_new_signal", "determine_corrosion") |
| COUNTER | These WME's hold results of various counting operations |
| name | Name of specific counter (e.g. "counter_front_surface_average") |
| count | The actual count at any time |
| PLOT | A single WME of this class has information for the user interface |
| term_type | The terminal type is specified here |
| status | Flat to indicate that echo feature plotting has been initialized |
| CUR_ECHO | A single WME for each signal identifies the current echo |
| signum | The number of the signal being investigated |
| echo_num | Number for the current echo (changes when looking for multiples) |
| loc | The location for the current echo |
| DIFF_ECHO | WME's to store time separations between echos for multiple search |
| signum | The number of the signal being investigated |
| ech_1 | The echo number for the echo with lower location value |
| ech_2 | The echo number for the echo with higher location value |
| diff | The difference in location values (higher-lower) |
| offset | The difference between the exact multiple separation and "diff" |
| h_ratio | The quotient of the height of ech_2 and ech_1 |
| LIMITS | One WME of this class for each possible first multiple |
| lower | Location diff. (first mult. - dominant-constraint_loc_multiple) |
| upper | Location diff. (first mult. - dominant + constraint_loc_multiple |
| exact | Location difference (first mult. - dominant) |
| OVERLAP | These WME's hold information used to identify overlapping echos |
| ech_1 | Number for one echo which may overlap another |
| ech_2 | Number for another echo which may overlap ech_1 |
| lowlim | Location of ech_1 minus the average of the two echo widths |
| uplim | Location of ech_1 plus the average of the two echo widths |
| CORROSION | WME's to hold information on the nature of the corroded surfaces |
| type | Descriptor for corrosion nature (e.g. "smooth_front_surface") |
| echo_num | Echo number giving rise to the conclusion on surface nature |
| depth | Maximum depth of any pitting in the spot area |
| size | Maximum size of any pit opening within the spot area |

For example, in OPS5, a particular working memory element of class "echo" might contain the following instances of attributes:

| | | |
|---|---|---|
| signum | 5 | (fifth signal waveform on a run) |
| echo_num | 5 | (fifth echo in that waveform) |
| width | 20 | (20 samples "wide"—time duration) |
| loc | 144 | (144th sample in the waveform) |
| height | 102 | (units of voltage) |
| type | pit | identification—perhaps tentative) |
| status | plotted | (flag for user interface) |
| tag | nil | (as yet undefined) |
| multiple_of_mark | nil | (as yet undefined) |

Constraints are used to guide the activation of rules, controlling the sensitivity of the system during identification of echos and structures. Table 3 shows actual constraints. The numeric values held in element-class "constraints" are applied in the condition part of a rule to determine if it should be activated. These constraint values are part of the heuristic nature of the rules. Both rule-constraints and ultrasonic parameter values are stored as "constraint" elements.

Particular constraint values, such as those in Table 3, are chosen by a system operator. The constraint values may be modified during the actual processing of a signal.

TABLE 3

List of Preprogrammed Constraints for the Rule-Based System

| CONSTRAINT NAME | VALUE |
|---|---|
| Value (height) constraints: | |
| constraint_on_value_dominat | 2 |
| For an echo to be a dominant echo, the height must be this factor greater than any other. | |
| constraint_on_leading_value % | 80 |
| This constraint sets the height value used in the identification of a dominant echo. The constraint is only used when an echo overlaps the maximum height echo. If the height of this other echo exceeds the above percentage of the maximum echo height, and comes before the echo with maximum height, then the echo is identified as the dominant echo (rules "max_overlap, wide_dominant, and wide_dominant_first") | |
| height_ratio_pit/spurious | 2 |
| This constraint sets the height value used in the identification of a spurious echo. The constraint is only used when a pit echo has been identified within a multiple structure. For identification as a spurious echo, the height value of the unidentified echo must be less than the quotient of the pit echo height and the constraint value above. | |
| ratio_max/large_pit | 4 |
| This constraint sets the height value used in the identification of a pit. The constraint is only used when no multiples echos have been identified. For identification as a pit echo, the height value of an unidentified echo must be greater than the quotient of the largest echo height and the constraint value above. | |
| ratio_max/spurious | 5 |
| This constraint sets the height value used in the identification of a spurious echo. The constraint is only used when no multiples echos have been identified. For identification as spurious echo, the height value of an unidentified echo must be greater than the quotient of the largest echo height and the constraint value above. | |
| constraint_on_height_ratio_for_multiple | 2.25 |
| The value of the constraint is used to place an upper limit on the height of the next possible multiple. If the ratio of the heights of (1) the next possible multiple echo and (2) the current multiple exceeds this constraint, then the next echo cannot be identified as a multiple echo. | |
| default_front_surface_height | 175 |
| The value of this constraint is used as default value for the height of the front surface echo. It is only used for the calculation of the area of the pit for the very first signal, should this signal indicate a pit. Later calculations use the running average of front surface echo heights (for no corrosion). | |
| constraint_on_overlap_multiple | 1.6 |
| The value of this constraint is used to test for a pit echo overlapping a multiple echo. | |
| Other constraints: | |
| number_of_echos_for_multiples | 2 |
| This constraint sets the minimum required number of multiple echos for a valid multiple structure. If a lower number of "equal-time-spaced" echos are identified, then no structure is stored. | |
| number_of_echos_for_large_ multiple-set | 4 |
| If the search for a number of potential multiple structures reaches a point where one structure has a number of multiple echos equalling this constraint, the search for other multiple structures is cancelled. | |
| constraint_on_location_for_multiple | 17 |
| This constraint is used to set the tolerance on the spacing between echos in a possible multiple structure. For two echos to be multiples, they must be separated by a fixed number of samples, plus or minus the number of samples given by the constraint. | |
| Physical constraints: | |
| transducer_spot_size(sq.inches) | 0.5625 |
| Actual area of sensor spot for given sensor to pipe wall separation. | |
| pipe_inner_cir(inches) | 22 |
| Pipe inner circumference. | |
| spot_y_offset(inches) | .75 |
| Sensor spot dimension in direction of pipe long axis. | |
| spot_x_offset(inches) | .75 |
| Sensor spot dimension in along circumference of pipe. | |
| default_area_small_pit(sq._inches) | 0.0123 |
| Smallest area to be reported for an identified pit. | |
| min_nominal_wall_thickness(inches) | 0.300 |
| Minimum wall thickness expected for the pipe. | |
| microseconds/sample | 0.02 |
| The time interval between sampled values. | |
| speed_in_steel(inches/microsecond) | 0.223 |
| Sound speed in the pipe material. | |
| speed_in_liquid(inches/microsecond) | 0.0583 |
| Sound speed in the liquid between sensor and pipe wall. | |

As an example of a constraint, the rule "LEADING_PIT_FRONT" (1812, FIG. 18) uses the constraint "min_nominal_wall_thickness" identified as a pit echo. The nature and means of execution of this rule is described below, in the section on Firing of Rules in the Knowledge Base.

iii. Firing of Rules in the Knowledge Base

This section first presents an in-depth description of the process through which an individual rule may be fired. Special attention will be paid to the use of classes and attributes of working memory elements (Table 2) and of preprogrammed constraints (Table 3). Then, this section will present a synopsis of how the rules interact with one another, in preparation for the detailed analysis in Structure of the Knowledge Base, and in the Appendix.

The ECHOS_LEADING_PIT_FRONT rule is exemplary. This rule looks for the case of a large flat pit. In this case, multiples can be generated between the top surface of the pit and the outer wall of the pipe. If a large pit is present, then the remaining wall thickness, as determined from the multiple separation, must be less than the "min_nominal_wall_thickness." An English condensation of the major features of the rule is as follows:

| IF | | There is complete multiple structure (all multiples found) |
|---|---|---|
| | and | an echo has been identified as the leading echo of this structure |
| | and | the constraint "min_nominal_wall_thickness" has value MNWT |
| | and | the remaining wall thickness calculated from the multiples is < MNWT |
| | and | there are no echos except those in the multiple structure |
| THEN | | |
| | | Identify the leading echo as an echo from the pit surface |
| | and | create a working memory element of class "structure" for the pit echo. |

In the preferred embodiment, the rule is implemented in OPS5 as follows:

```
echos_leading_pit_front
    (structure ^type multiple ^generator_num <de#>
     ^f_mult <fmult> ^status labeled)
    {<ech>(echo   signum <s#> ^echo_num <de#>
     ^type leading ^tag <fmult>) }
    (constraint ^name min_nominal_wall_thickness
     ^value <mwt>)
    (computed ^name remaining_wall_thickness
     ^value {< <mwt>})
    -(echo ^signum <s#> ^tag {<> <fmult>})
```

-continued

```
-(echo ^signum <s#> ^type nil)
→
    (modify <ech> ^type pit ^status nil)
    (bind <t>Found_structure_"pit_dominant_as_front_-
    surface"_for_ pit)
    (write (crlf) <t> <de#>)
    (make structure ^type pit_dominant_as_front_surface
    ^generator_num <de#> ^number <de#>)
```

This rule, ECHOS_LEADING_PIT_FRONT, will next be explained in detail so that the use of Table 2 and Table 3 in actual programming by one of ordinary skill will be facilitated. Of course, the particular programming language, rule organization, rule content, rule interaction, working memory element classes and attributes, and constraint identity and value are presented purely by way of illustrative example, and do not limit the scope of the present invention.

As in many rule-based programming languages, OPS5 may be described generally as follows. The rule comprises a left side and a right side. The left side comprises (in our case) four affirmative conditions and two negative conditions. The right side comprises four actions which are performed when all six conditions have been met.

On the left (conditional) side of the rule are located a list of six conditions. Each condition is a pattern which the inference engine attempts to match against the elements of working memory. Each condition is of the form:

Class ^attribute atom/<variable> ^attribute
    atom/<variable>

Reference may be made to the classes and attributes in Table 2 and its accompanying description for a deeper understanding of each of the six conditions in this rule. For example, the four different classes which are invoked by the six conditions of this rule are "structure", "echo" (three occurrences), "constraint", and "computed".

Basically, this first condition ensures that a multiple has already been defined at that point in the execution of the rule-based system.

The first condition is that there must be, somewhere in working memory, a working memory element of class "structure" having the four attributes specified in the rule above, namely: attributes "type", "generator_num", "f_mult", and "status".

The specification of class "structure" eliminates from consideration all working memory elements which are not of that class.

"Type multiple" ensures that, of all working memory elements of class "structure" (see Table 2), only those working memory elements having class "structure" and of type "multiple" are further considered. (Other "types" of structures include pits and front surface.)

Also, for the working memory element of class "structure" matching the pattern demanded by this condition of this rule, the generator number is read into a local variable, <de#>.

For the matching working memory elements, the value of the attribute "f_mult" is placed in the local variable <fmult>.

Finally, the "status" of the working memory element must be the atom "labeled".

A second condition causes the inference engine to look through the working memory for a working memory element of class "echo", as shown immediately to the right of the left parenthesis "(". (The symbol <ech> will be explained below.)

The first attribute of this working memory element can be any value, and is assigned the value <s#> and takes on a value which is used later in the rule. The requirement "echos_num <de#>" performs a test as to whether the particular attribute in the working memory element under consideration has the same value as was read in during processing of the previous condition, in the attribute "generator_num".

The "type leading" requirement ensures that the working memory element under consideration is a leading echo.

Finally, the fourth requirement of the second condition of the rule is that the attribute "tag" be the same as the variable "fmult" read in during the execution of the first condition above.

Basically, this second condition of the rule checks for the consistency that there is a leading echo generated within a multiple structure. This condition effectively labels the particular echo which is identified as the leading echo. This labeling is accomplished by the <ech> which is at the extreme left of the second condition of the rule. This <ech> is used in the first action (on the right hand side of the rule) so that the particular working memory element detected in the second condition is the one whose type is modified from "leading" to "pit".

The third condition of the rule is that there be a working memory element of the class "constraint" (see Table 3) with a name "min_nominal_wall_thickness" having a value "<mwt>".

The fourth condition of the rule is that there be a working memory element of class "computed" having a name "remaining_wall_thickness" and whose value is strictly less than the value "mwt" read in during the third condition. "mwt" is the minimum wall thickness which is to be expected (including a small degree of tolerance, of course).

Basically, conditions 3 and 4 test for the condition that the computed remaining wall thickness (based on a calculation based on multiple separation, carried out in another rule) is less than that which would be expected for an uncorroded pipe. Essentially, this is a crucial test for determining whether a multiple has been created by internal reflections from a pit surface, rather than from the front surface of the tubular.

The fifth and sixth conditions of the rule are negative conditions. That is, none of the actions on the right side of the rule will be executed if the fifth and sixth conditions (to the right of the minus signs) are met.

The fifth condition prevents firing of the rule if the "signum" (echo index number) equals the local variable "s#" read in during the testing of the second condition of this rule. Also, the tag for this "echo" working memory element must not be equal to the value of the variable "fmult" read in during the processing of the first condition of this rule. Basically, the fifth condition of this rule ensures that there are no other echos in this signal except those in the multiple structure. The absence of other echos is ensured because, in another rule, this tag attribute is set equal to the echo number of the first multiple, so that if there are no other echos with tags other than "fmult", there must be no other echos in the signal besides those in the multiple structure.

The sixth condition of the rule, also a negative condition, ensures that there are no unidentified echos in the signal. Unidentified echos are characterized in that their working memory elements have a type "nil". Presence of "nil" indicates that no information has been added to that attribute.

If all six conditions have been met, then all four of the actions (on the right side of the rule) will be taken.

The first action which is taken in the event that all six conditions are met is that the "type" of the working memory element discovered in the matching test performed during the processing of the second condition is modified from "leading" to "pit". The "status" (used for plotting purposes in the user interface) is changed to "nil" so that a bookkeeping rule detects the fact that this echo's status has been changed and plots it as a pit echo rather than a leading echo.

The second and third actions on the right side of the rule are effectively a print command which tells the user that a pit echo (rather than a front surface echo) indicates the presence of the observed multiple structure.

The fourth and final action to be taken when this rule is fired is that a working memory element of class "structure" is created. A structure type is "pit_dominant_as_front_surface" whose "generator_num" and "number" are both the value "de#" assigned during the processing of the first condition of the rule, above.

This concludes the detailed description of the rule ECHOS_LEADING_PIT_FRONT. Tables 2 and 3, the detailed description of the rules given in the Appendix, and the sequence of rule firings in Table 4 facilitates the understanding and practice of the invention. Changes in any of the rules or their interactions may be effected without departing from the scope of the present invention.

Having completed a detailed description of a particular rule, the following exposition is presented as a more global description of the preferred embodiment.

In order to describe the structure and interaction of the rules in the various knowledge bases, "activation-diagrams" are shown in FIGS. 15-20. These diagrams are similar to "and/or" diagrams used to describe search trees See, e.g., Winston, P. H., *Artificial Intelligence.* Addison-Wesley, Reading, Mass., 1977. The activation-diagram is used to specify which rules must have "fired" (been activated) before the conditions for any other rule can be satisfied. In FIGS. 15-20, circles, lines and arcs are used to connect rules. Rule-connection points are indicated by the circles. Lines between two rules indicate a dependence of the lower rule upon the action part of the upper rule. Thus, when a rule is dependent on two or more rules there are two or more lines intersecting at the top of the dependent rule. When these lines are connected by an arc (for example, 1524 in FIG. 15), all of the higher level rules must have been activated (an "AND" function). As an example, consider the conditions for rule COMPUTE_AVERAGE_FRONT_SURFACE_HEIGHT (1522 in FIG. 15). The higher level rule, SET_FRONT_SURFACE_HEIGHT 1510, must fire before this rule 1522 can be activated. In addition, a rule MULTIPLE_NO_CORROSION from 1520 (2024 in FIG. 20) in the ULTRASONICS knowledge source must also have fired. Otherwise, in the absence of any arc any one of the higher level rules could have been activated for the conditions of the lower rule to be met (an "OR" function).

Any one of activation-diagrams in FIGS. 15-20 may contain rules from many knowledge sources. They have not been constructed to show exclusively the activations of single knowledge sources. Rather, they reflect the interactions of the knowledge sources and the opportunistic nature of the rules.

A complete description of the rules in the knowledge sources is given in the Appendix. The basic solution methods used for each KS are described in the following sections.

iv. Output of Corrosion Information—The User Interface

The presentation of corrosion information is a function of the user interface of the expert system. In the preferred embodiment, the output of information may be on any standard output device, such as a cathode ray tube (CRT) or on a printer.

The particular information which is output varies with the degree of confidence which the user has in the reasoning ability of the expert system on a given task. If the user had high confidence in the ability of the expert system to arrive at correct conclusions, the expert system may display or print only its ultimate conclusions, such as whether there is any corrosion in a given section of pipe.

If the user had less confidence in the ability of the expert system to arrive at correct conclusions all of the time, the expert system may be commanded to present its conclusions, as well as the reasoning by which it arrived at those conclusions. The "reasoning of the expert system" is, of course, the path taken through the rules of the knowledge sources to arrive at a given conclusion. Commonly used expert system shells, such as OPS5, have their own means of "expressing their reasoning". These means are commonly called the "explanation facility", any embodiment of which is contemplated by the present invention. A preferred embodiment of the explanation facility is that illustrated in Table 4, described in the section entitled "Processing Example." (See also the discussion of FIG. 21 in that section.)

For example, in areas of the target surface where there is known to be corrosion, the user would likely wish to verify the accuracy of the expert system's conclusion. The actual presentation of the analysis by the expert system of an actual full echo waveform (that of FIG. 10) will be described in detail below, in the section entitled "Processing Example". Of course, the presentation given below is offered to demonstrate only one possible embodiment of the way in which information could be presented to a user. Variation of the structure, sequence, and organization of the method of output of information lies within the contemplation of the present invention.

In addition to presenting its reasoning, the expert system may create a graph of the inspected surface which it has concluded has caused the full echo waveform under consideration. The graph may be either a "facial" (trans-ducer-eye) view, or a cross-sectional view, of the target surface. A facial view advantageously color-codes different areas of the target surface according to the different depths of corrosion pits which have been detected. The user can then judge the credibility of the system's conclusions, perhaps based on his personal experience.

The human user's interactive input of information into the expert system according to the preferred embodiment of the present invention may be accomplished by any of a variety of input devices known in the art, such as a keyboard, "mouse", or any of the more exotic devices described generally above in the section entitled "General Introduction to Artificial Intelligence."

The user interface may allow the user to change certain intermediate conclusions in the reasoning process by which the expert system arrived at its own conclusion, so that the user can investigate hypothetical interpretations at will. The section entitled "Processing Example" illustrates but one example of the means by which a human user can view the process by which the expert system arrived at a set of conclusions regarding a particular full echo waveform. At any point in the sequence of rule firings listed in Table 4, above, the user could interrupt the system and substitute a different constraint or attribute value so that he could view the effect which that change had on the final conclusion arrived at by the expert system. Thus, the ability to input constraints or attribute values during the actual execution facilitates the judicious choice of constraints for future runs. In this way, the expert system acts as its own software development system.

d. Structure of the Knowledge Base

Figure 14:
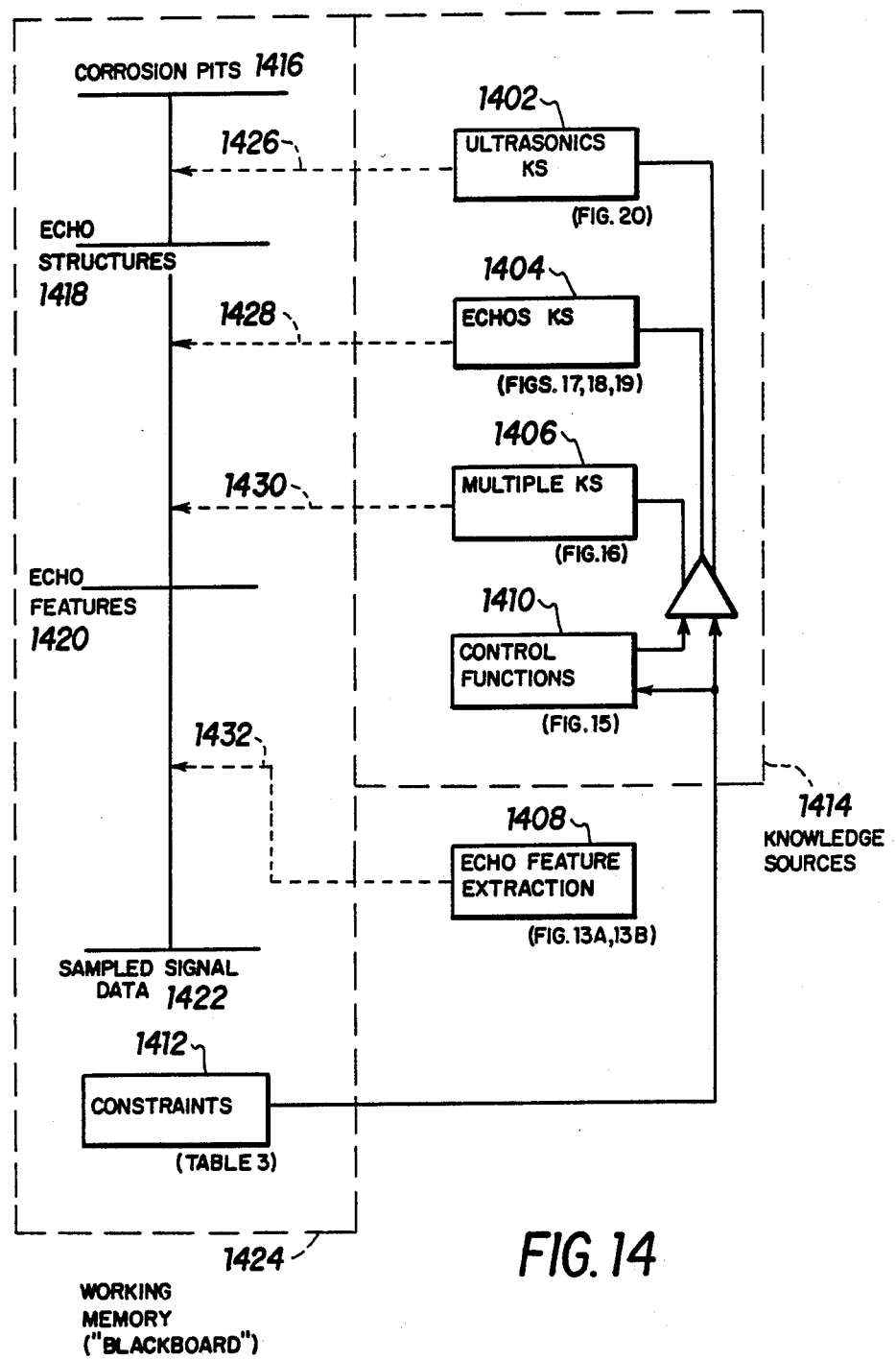
FIG. 14 shows in very general form the structure of the rule-based system according to the preferred embodiment of the present invention, showing the relation of the knowledge sources to the working memory ("blackboard").

FIG. 14 is a diagram indicating the structure of the rule-based system according to the preferred embodiment of the present invention.

Generally, everything that is illustrated in FIG. 14 (except perhaps Echo Feature Extraction routine 1408) may be considered part of the knowledge base of the expert system. The knowledge base comprises two major components. The first component is the "blackboard" (or, more commonly, "working memory"). The second component is the set of knowledge sources generally indicated at 1414. The set of dotted lines with arrows on their ends indicate the means by which information in the working memory is (or may be) modified by rules in the knowledge sources firing.

Working memory 1424 comprises declarative information in the form of constraints 1412, as well as other declarative information 1416, 1418, 1420 and 1422 regarding the signal and the physical structure about which conclusions are to be made.

In the preferred embodiment, the physical structure about which conclusions are to be made is the surface of a borehole tubular in an oil well. The sampled signal data 1422 is the full echo waveform received by the acoustic transducer. The echo features 1420 include the height, width, and location (time of occurrence) of each particular echo pulse. The echo structures 1418 comprise such information as whether individual echos are pit echos, front surface echos, or members of a multiple structure. Corrosion pits 1416 contain the ultimate conclusions as to the nature of any deformities in the target surface, such as the location, depth and area of corrosion pits in the tubular.

Working memory elements are basically discrete items of declarative information which are created, and possibly modified, and even deleted, by the rules as they fire. The progression of the expert sytem from waveform information to target surface conclusions is accomplished by the chain of intelligent firing of the rules. Working memory elements are of the "classes" and patterns of "attributes" listed in Table 2.

A preferred embodiment of the constraints in constraints memory 1412 of the working memory 1424 are listed in Table 3. Generally, constraints take on a single value (although some may be changed during operation). Constraints are usually parameters derived experientially, and lead the expert system to efficiently arrive at its conclusions. Also, the constraints memory 1412 allows flexibility in applying the system to a variety of physical situations. For example, the "pipe_inner_cir" (pipe inner circumference) can be altered simply by changing one value in a constraints memory rather than changing the value throughout all the rules in which the standoff is used.

The knowledge sources act upon the declarative knowledge in the working memory. All of the knowledge sources 1402, 1404, 1406, 1408 and 1410 are described immediately below. These knowledge sources contain the rules, such as those described above in the section Firing of Rules in the Knowledge Base, which effectuate changes in the working memory elements so that concluions as to the nature of the target surface are ultimately reached.

The arrows with dashed lines, indicated as 1426, 1428, 1430, and 1432, indicate the actions taken (on the "right hand side" of the rules). The rules are selectively executed, based on the present contents of the working memory, in a manner well understood in the art.

It should be understood that FIG. 14 is very schematic in nature, and does not represent an exhaustive description of the present invention. It also does not show how even this particular application of the invention need be implemented. It is presented mainly as an aid in understanding the particular descriptions of the knowledge sources presented immediately below, as well as the individual rule descriptions in the Appendix.

FIG. 14 is to be contrasted with FIG. 12, which represents a flow diagram. FIG. 12 indicates generally the timewise order of activation of the various functions of full echo waveform analysis. With this understanding of the structure and flow of the analysis in FIGS. 14 and 12, the following more detailed descriptions may be placed in context.

i. Control Functions

Figure 15:
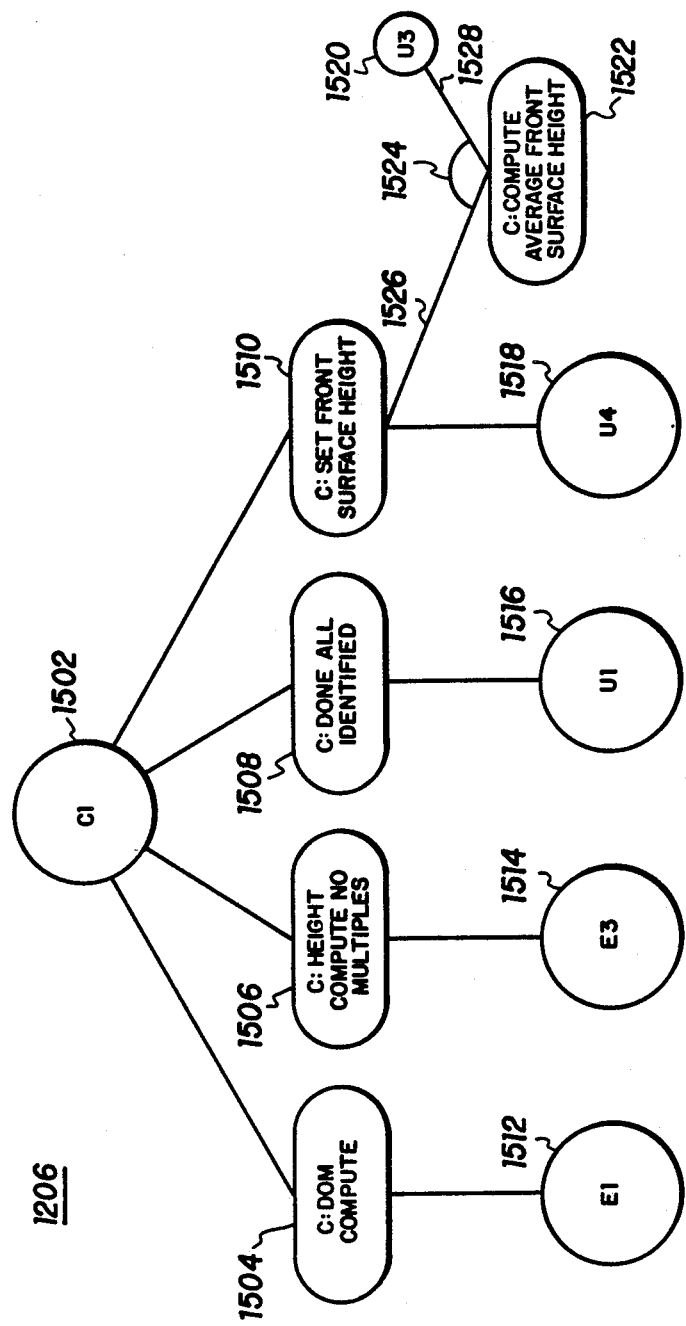
FIG. 15 is an activation diagram for the Control Function knowledge source of FIG. 12.

Once the echo data and constraints are stored as working memory elements, processing begins with the execution of "control" rules (FIG. 15). These rules act to guide further rule activation down the two branches 1208 and 1210 (FIG. 12) discussed previously for the "multiples" and "no multiples" cases.

In addition, rules in the control function are used to determine when all echos have been identified, and to compute the average height for the "front-surface" echo. This average height is advantageously a running average of front surface echo heights for physically successive signals from uncorroded areas.

Also, rules in the Control Function allow predispositions to be built into the rules for the analysis of a given full echo waveform signal, if part of the spot corresponding to the present signal was covered by an overlapping spot from a previously-analyzed signal (note areas of spot overlap in FIG. 6B). For example, suppose that analysis of a first signal indicated the presence of a pit of a given depth, and analysis of a second signal (whose spot overlapped that of the first signal) indicated an ambiguity as to whether a certain echo was a pit echo or a spurious echo. Rules in the control function corroborate the presence of a pit of that depth in the second spot. This corroboration may, for example, take the form of a presumptive initial assignment of an echo "type" attribute of "pit".

ii. MULTIPLES Knowledge Source

The MULTIPLES KS (FIG. 16) is an important element of the rule-based system (FIG. 14). Once a multiple structure is found and eliminated from consideration, further processing is simplified due to the reduced number of echos to be identified. Any echo which is not part of the multiple structure is a potential pit echo.

A "multiple structure", as defined above with respect to FIG. 9, is a series of substantially equally timed echos resulting from acoustic energy reverberating within a target object such as an oil well tubular. If the only information one is seeking is about pit echos, then the echos in a multiple structure may be considered "confounding signal structures" on the full echo waveform, inasmuch as they may masquerade as pit echos (the true, "informational signal structures" on the full echo waveform).

In more general terms, once the confounding signal structure has been detected, identified, and (at least temporarily, or for some purposes, permanently) eliminated from consideration, then the informational signal structures, if any, are laid bare for further analysis, free of the corrupting influence of the confounding signal structure. The substantially equally-spaced echos of a multiple structure are thus but one example of a confounding signal structure.

Other examples of confounding signal structures might include the delayed versions of a received radio or radar signal which are superimposed on the received radio or radar signal itself, in the presence of multipath interference. Detection and subsequent elimination from consideration of these delayed multipath signals is readily accomplished through variation of the particular embodiment described in this disclosure. Instead of focusing on elimination from consideration of equally-timed echos, the rules would focus on elimination from consideration (or perhaps time-correcting and constructive superimposing) of delayed signals on a stronger, primary signal. The primary signal without the delayed signals (or strengthened by the constructive superimposing of the time-corrected delayed signals) would then constitute the informational signal structure.

Similarly, the expert removal of confounding signal structures finds application in seismic exploration. Wave energy returned from geological formations is embodied in complex waveforms which contain signal structures which are confounding signal structures (for example, echos reverberating within certain geological formations at different depths). Isolation, and elimination from consideration, of these mutually confounding signal structures facilitates analysis of the individual, informational signal structures.

A single signal structure may be both a confounding signal structure (for one purpose) and an informational signal structure (for another purpose). Specifically, in the oil well tubular application, multiple structures are confounding signal structures (and pit echos are information signal structures) when the purpose of analysis is, for example, to determine the presence of a small pit. On the other hand, pit echos are the confounding signal structures (and multiple structures are the informational signal structures) when the purpose of analysis is, for example, to determine the remaining wall thickness directly from the separation of multiple structure echos.

With the understanding that the application of the rule based analysis technique to full echo waveforms of acoustic echos returned from the surface of oil well tubulars is merely the preferred embodiment of the invention, the following discussion describes the preferred means of identifying multiple structures for purposes of exemplification, and not limitation.

The identification of a multiple structure is based on the fact that there must be a fixed separation between multiple echos. Once a dominant echo for the possible multiple structure has been identified, the system looks for a series of later echos which occur at a fixed (but as yet unknown) separation. An effective recursive loop 1609 between MULTI_FIND 1608 and MULTI_DIFF 1606 does most of the work. (A description of the rule interactions for the identification of multiples is given below. In addition, the rule firings for the example signal of FIG. 10 are presented in Table 4, and are explained in the section "Processing Example," below.)

The recursion starts with the calculation of the separation between the dominant echo and the next echo. Rule MULTI_DIFF 1606 performs the actual subtraction necessary to calculate the separation. This next echo is marked the *first*-"current echo." Rule MULTI_FIND 1608 then looks for another, later echo which is separated from the "current" by the same separation. If such an echo is found, it becomes the "current" and another, later echo is investigated. If enough of these echos are found, a multiple structure is identified.

As a final step in the recursion, the first-"current" echo after the dominant is marked the "first multiple." If there are no echos after the *first*-"current" echo which are separated by the proper interval, the rule MULTI_START restarts the process. The next echo after the previous first-"current" echo becomes the "current" echo. Possible multiple structures at this new, larger separation are investigated.

Since every echo after the dominant is considered as a possible first multiple, several multiple structures can be identified in a complex signal. Rules within the MULTIPLES K decide which potential multiple structure is the most probable.

Once a single multiple structure has been identified, the individual echos are labeled. The system, according to the preferred embodiment, does not spend any more time trying to identify the labelled multiple structure echos.

iii. ECHOS Knowledge Source

The ECHOS knowledge source is a grouping of rules which are used for echo identification. The three parts of this knowledge source have been shown previously as 1212, 1214, and 1218 in FIG. 12. The parts are connected to other KS's at connection points E1, E2 and E3 as indicated in FIGS. 12 and 17–19.

A. Dominant Echo Identification (E1)

Figure 17:
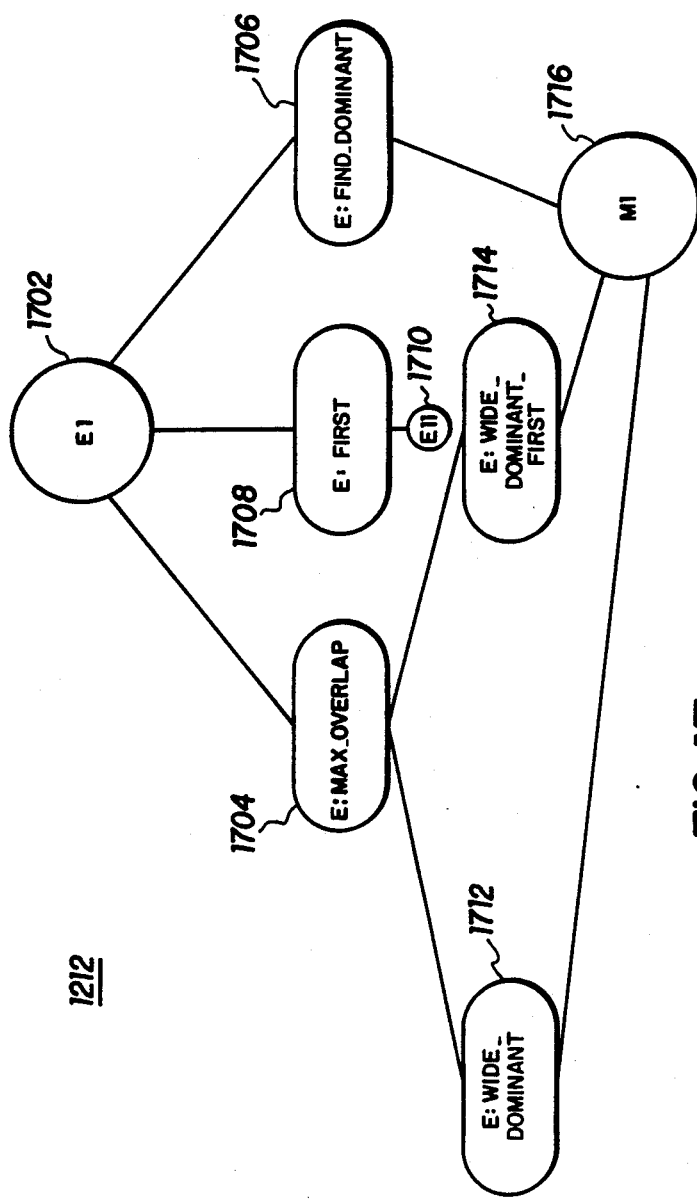
FIG. 17 is an activation diagram for the "E1" portion of the ECHOS knowledge source of FIG. 12 which identifies the dominant echo.

The activation diagram for the first part of the ECHOS KS is given in FIG. 17. This group of rules is primarily involved with the identification of a "dominant echo" (defined in Table 1). The dominant echo is important because its presence in the signal indicates that a multiple structure may be present.

In more general terms, a dominant echo can be conceived as an indicator that a confounding signal structure (in the case of oil well tubulars, a multiple structure) may be present. Different confounding signal structures (for different applications, such as multipath communications or seismic interpretation) may have respectively different confounding signal structure indicators.

A single confounding signal structure may have more than one confounding signal structure indicator. Conversely, a confounding signal structure may be of such a nature that the only confounding signal structure indicator is the confounding signal structure itself. Thus, a preferred embodiment's identification of a "dominant echo" as a confounding signal structure (multiple structure) indicator is presented by way of example, and not limitation.

In a preferred embodiment, the rule FIND_DOMINANT determines if a dominant echo exists. This rule is activated if an echo has a height which is some predetermined factor (e.g., 2) greater than any other. Knowledge about the ultrasonic method would suggest that such a large echo could have been generated by a large flat surface. Similarly, this flat surface may form a multiple reflection path with the outer wall of the pipe.

The other rules in this part test for the presence of several dominant echos. This case can occur when there is minor surface roughness on the inner wall of the pipe. The roughness can result in the generation of large neighboring echos at the beginning of the signal, a phenomenon called peak splitting.

B. Identification of Echos Other than an Identified Multiple Structure (E2)

Figure 18:
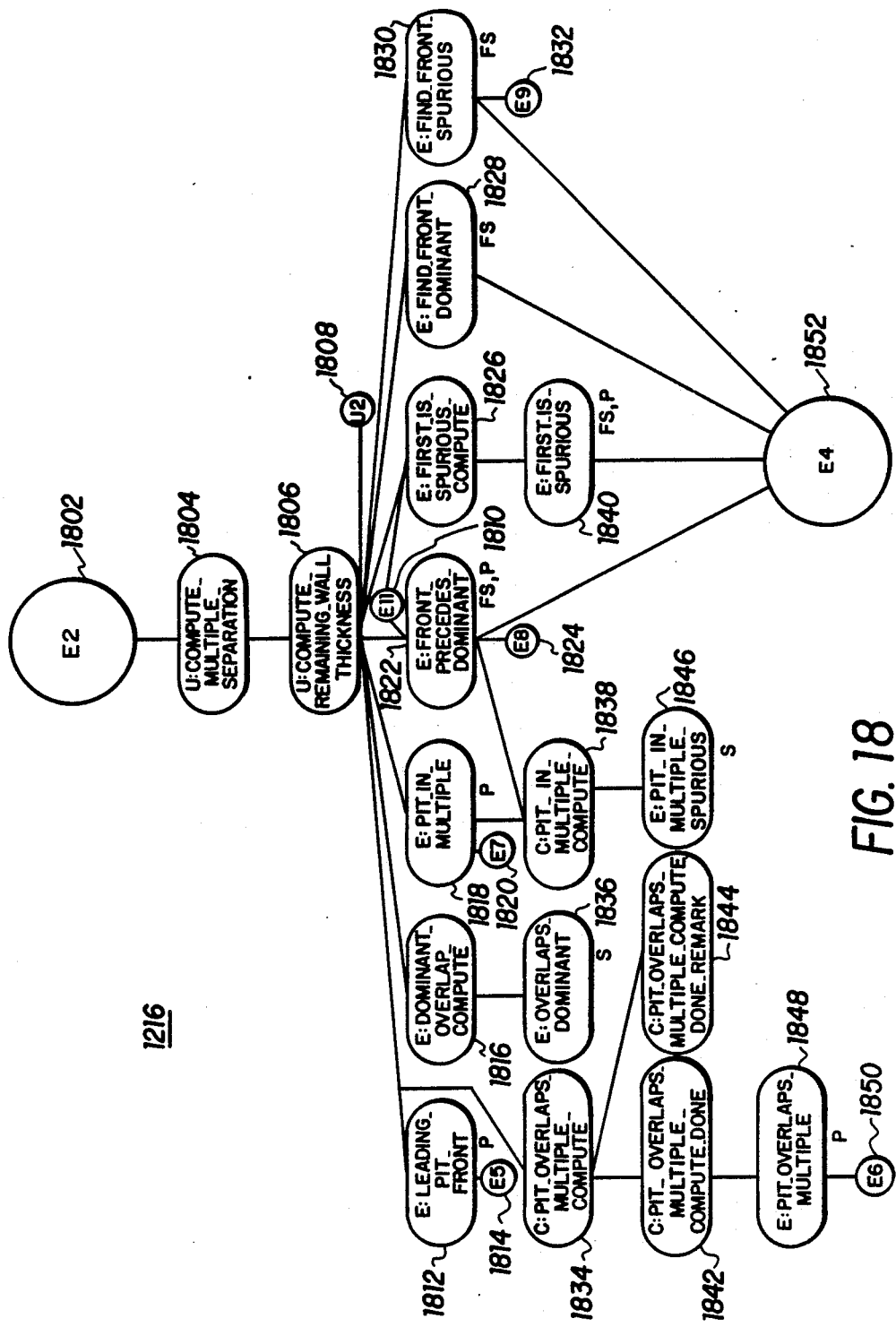
FIG. 18 is an activation diagram for the "E2" portion of the ECHOS knowledge source in FIG. 12 which identifies echos other than multiple structure echos, assuming a multiple structure has been identified.

Once a multiple structure has been found, the second part of the ECHOS KS deals with the identification of all other echos (connection point E2). The activation diagram for this second group of rules is shown in FIG. 18. Two rules 1804 and 1806 from the ULTRASONICS KS must fire before any rules in this portion of the ECHOS knowledge source are activated. These two rules are used to determine the remaining wall thickness, based on the separation between multiples. They are considered part of the ULTRASONICS KS because they contain knowledge concerning the ultrasonic process. However, since the rule-based program is nonsequential, they can fire at any time. The activation of these two rules sets up for the identification of echos within the multiple structure.

In addition to the identification of echos from corrosion pits, both "front-surface" and "spurious" echos are identified. Each rule is used to identify these three echo types in different situations. The letters FS, P, S below a rule indicate the identification of a "front-surface," "pit" or "spurious" echo respectively. The "front-surface" echo is generated by a reflection from the first material surface encountered by the ultrasonic signal. "Spurious" echos are any echos which do not play an important role in the interpretation of the signal. For example, rule OVERLAPS_DOMINANT (1836 in FIG. 18) finds spurious echos which are very near the dominant echo and are normally generated by minor pipe surface-roughness.

C. Identification of Echos in the Absence of Identified Multiple Structures (E3)

Figure 19:
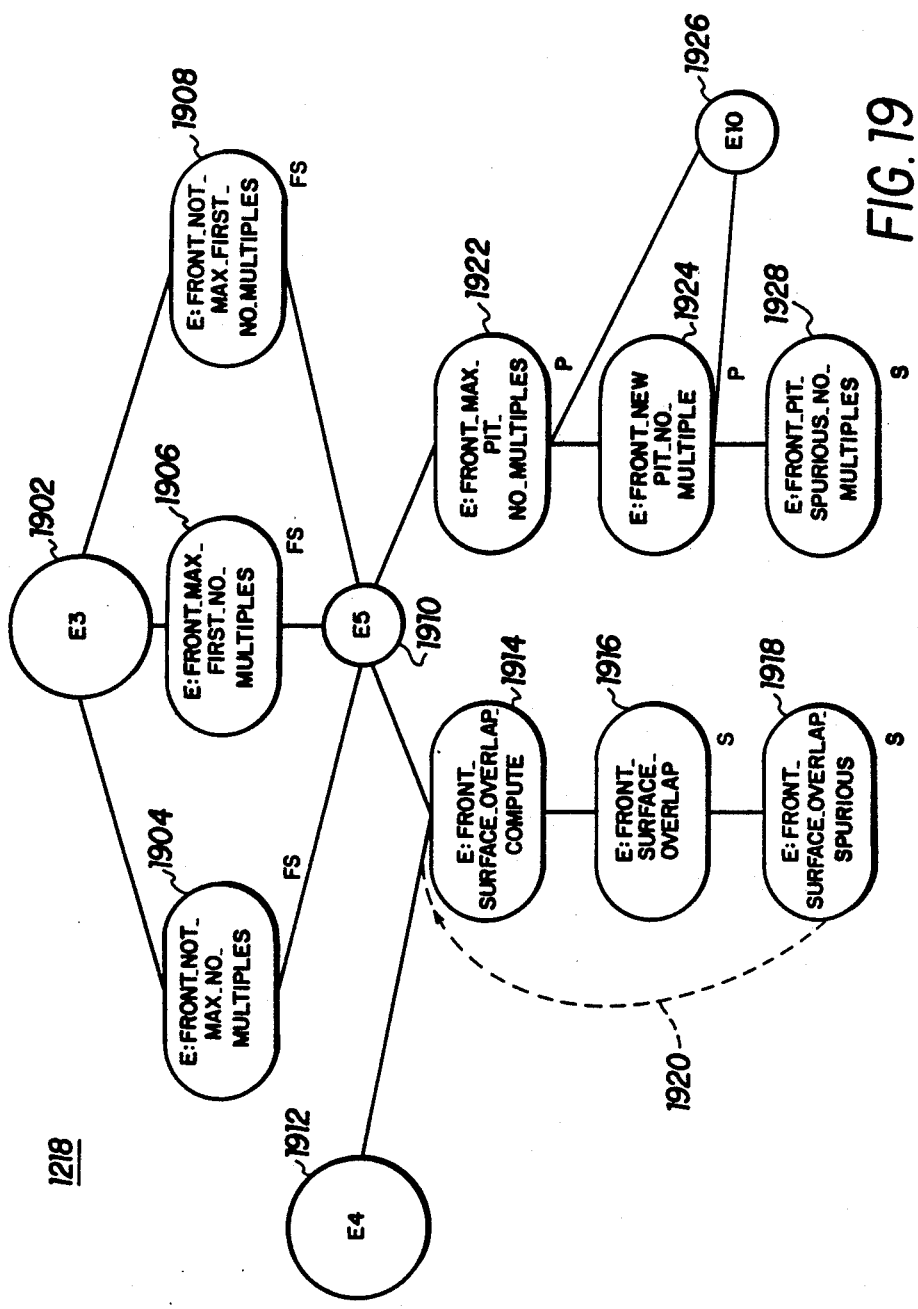
FIG. 19 is an activation diagram for the "E3" portion of the ECHOS knowledge source of FIG. 12 which identifies echos in the absence of any identified multiple structures.

The third part of the ECHOS KS handles the case when no multiple structure has been identified. The activation diagram is shown in FIG. 19. In addition to the identification of front-surface and pit echos, echos which overlap the front-surface echo are investigated. When all echos are identified, control functions return processing to the ULTRASONICS KS.

iv. ULTRASONICS Knowledge Source

The ULTRASONICS KS is a grouping of rules which contain knowledge about the ultrasonic reflection process. In addition, the determination of the characteristics of the corrosion pits is performed by this KS. The activation diagram is shown in FIG. 20 with a connection point U1 to the control functions.

Figure 20:
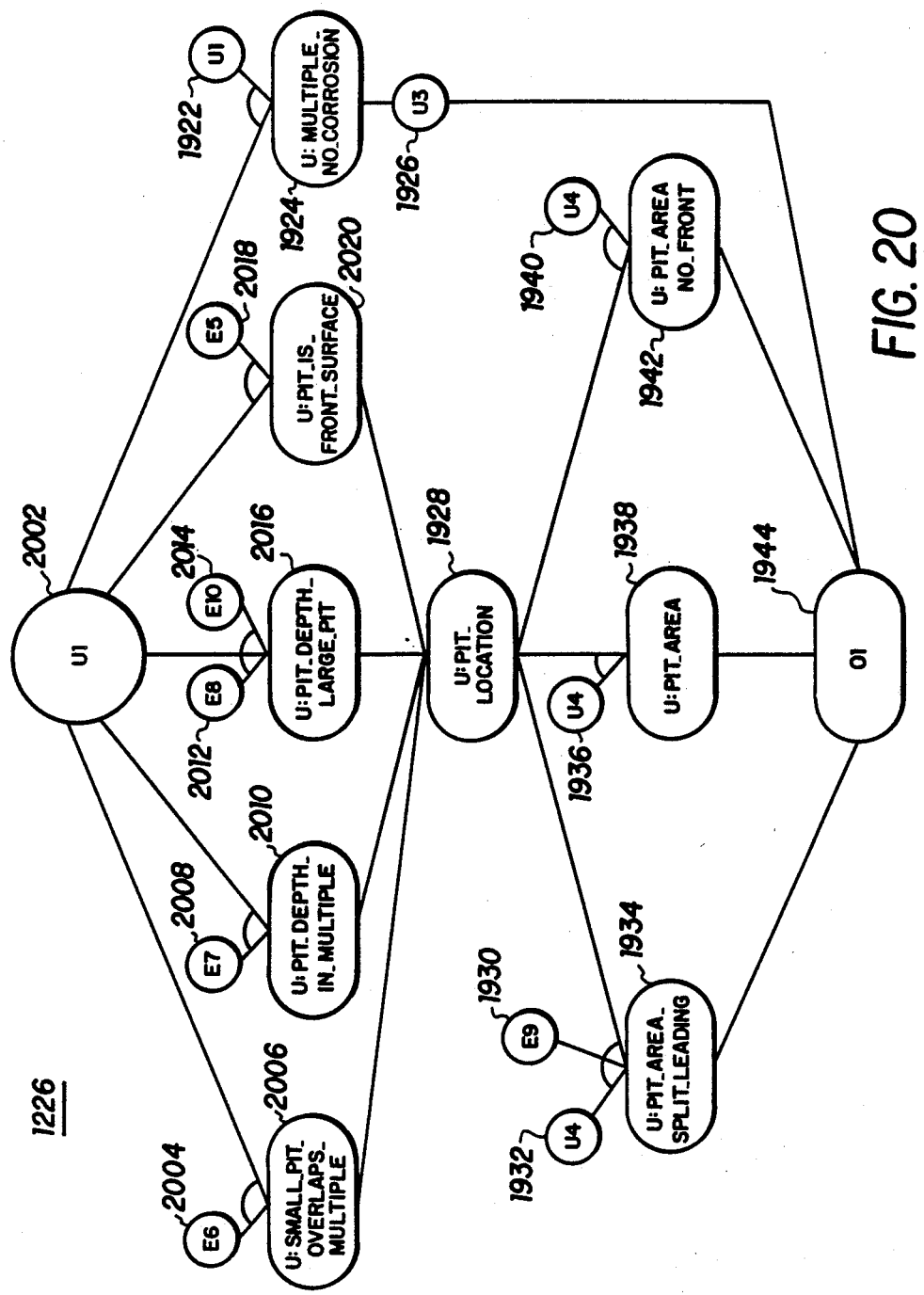
FIG. 20 is an activation diagram for the ULTRASONICS knowledge source of FIG. 12.

The top-level rules in FIG. 20 are used to determine the pit characteristics for various types of pitted surfaces. The "ANDed" connections to the rules in the ECHOS KS indicate the dependence on the type of pit echo identified.

First, the depth of the pit is calculated from the time separation between the front-surface and pit echo using a formula:

$$D_{pit} = 0.5 * V_e * T_{p-f}$$

where $V_e$ is the acoustic velocity in the liquid, and $T_{p-f}$ is the time difference between the pit echo and the front surface echo. See the Principles of Analysis, Pit Depth section above.

Next, the location of the pit on the pipe wall is taken to be the location of the spot area. This location is read in with the echo features.

Finally, the pit area is calculated using a formula:

$$A_{pit} = (1.0 - H_{FSE}/H_{FSE,O}) * A_{spot}$$

where $A_{spot}$ is the spot area, $H_{FSE}$ is the present measured front surface echo height, and $H_{FSE,O}$ is the mean front surface echo height as calculated or determined in the Principles of analysis, Pit Area section above. The front surface echo height is thus used as an indirect measure of the area of the pit.

At this point, memory elements for detected pits have been designated, and the location, depth, area and type attributes assigned. This data is output to a file, and the system is re-initialized for the next signal.

e. Processing Example

This section describes the operation of the rule-based system for the actual signal shown in FIG. 10. The rule activations for this typical real-world signal are listed in Table 4.

In addition, FIG. 21 shows a copy of the user-interface display for this example. This display is a "snapshot" of the display after identification of the corrosion is complete. Each echo of the full waveform has been represented as a rectangle in FIG. 21. The height, width and location (time) of these rectangles correspond to the actual echos shown in FIG. 10. The echos are numbered sequentially as indicated below each rectangle. The identification of the echos changes as the signal interpretation proceeds.

TABLE 4

| KS Rule Name | Function and echos involved |
|---|---|
| | Rule Firings for Example Signal in FIG. 10. |
| SET_FRONT_SURFACE_HEIGHT | Sets average front-surface height to constraint value |
| CONTR_DOM_COMPUTE | Echo 1 used to set constraints on dominance |
| ECHOS_FIRST | Label echo 1 as first echo in signal |

TABLE 4-continued
Rule Firings for Example Signal in FIG. 10.

| KS Rule Name | Function and echos involved |
|---|---|
| ECHOS_FIND_DOMINANT | Echo 1 is found dominant |
| MULTI_START | Echo 1 leading, Echo 2 is current |
| MULTI_DIFF | Compute location difference echo 2 - echo 8 |
| MULTI_DIFF | Compute location difference echo 2 - echo 3 |
| MULTI_DIFF | Compute location difference echo 2 - echo 4 |
| MULTI_DIFF | Compute location difference echo 2 - echo 5 |
| MULTI_DIFF | Compute location difference echo 2 - echo 6 |
| MULTI_DIFF | Compute location difference echo 2 - echo 7 |
| | (no multiple structure found with echo 2 as first multiple) |
| MULTI_START | Echo 1 leading, echo 3 is current |
| MULTI_DIFF | Compute location difference echo 3 - echo 8 |
| MULTI_DIFF | Compute location difference echo 3 - echo 4 |
| MULTI_DIFF | Compute location difference echo 3 - echo 5 |
| MULTI_DIFF | Compute location difference echo 3 - echo 6 |
| MULTI_DIFF | Compute location difference echo 3 - echo 7 |
| | (no multiple structure found with echo 3 as first multiple) |
| MULTI_START | Echo 1 leading, echo 4 is current |
| MULTI_DIFF | Compute location difference echo 4 - echo 8 |
| MULTI_DIFF | Compute location difference echo 4 - echo 5 |
| MULTI_DIFF | Compute location difference echo 4 - echo 6 |
| MULTI_DIFF | Compute location difference echo 4 - echo 7 |
| MULTI_FIND | Possible structure for echos 1-4-6, 6 is current |
| MULTI_DIFF | Compute location difference echo 6 - echo 8 (check) |
| MULTI_FIND_LAST | Found echo 8 as last multiple |
| MULTI_FOUND | Found structure for echos 1-4-6-8 |
| MULTI_START | Echo 1 leading, echo 4 current (Structure for 5?) |
| MULTI_DIFF | Compute location difference echo 5 - echo 8 |
| MULTI_DIFF | Compute location difference echo 5 - echo 6 |
| MULTI_DIFF | Compute location difference echo 5 - echo 7 |
| | (no multiple structure found with echo 5 as first multiple) |
| MULTI_START | Echo 1 leading, echo 6 current (Structure for 6?) |
| MULTI_DIFF | Compute location difference echo 6 - echo 8 |
| MULTI_DIFF | Compute location difference echo 6 - echo 7 |
| | (no multiple structure found with echo 6 as first multiple) |
| MULTI_START | Echo 1 leading, echo 7 current (Structure for 7?) |
| MULTI_DIFF | Compute location difference echo 7 - echo 8 |
| | (no multiple structure found with echo 7 as first multiple) |
| MULTI_START | Echo 1 leading, echo 8 current (Structure for 8?) |
| MULTI_SET_REMOVE_LAST | Remove false structure element for echo 7 |
| MULTI_SET_REMOVE_LAST | Remove false structure element for echo 6 |
| MULTI_SET_REMOVE_LAST | Remove false structure element for echo 5 |
| MULTI_SET_REMOVE_LAST | Remove false structure element for echo 3 |
| MULTI_SET_REMOVE_LAST | Remove false structure element for echo 2 |
| MULTI_SET_REMOVE_MIL | Remove false structure element for echo 8 |
| MULTI_SET_COMPLETE | Label completed structure for echos 1-4-6-8 |
| MULTI_CLEAN_DIFF | Fires 22 times to remove difference elements |
| MULTI_LABEL_START | Sets up counters for labeling multiple echos |
| MULTI_LABEL | Label echo 4 |
| CONTR_PIT_OVERLAPS_MULTIPLE_COMPUTE | Add echo 4 width to sum of multiple widths |
| MULTI_LABEL | Label echo 6 |
| CONTR_PIT_OVERLAPS_MULTIPLE_COMPUTE | Add echo 6 width to sum of multiple widths |
| MULTI_LABEL | Label echo 8 |
| CONTR_PIT_OVERLAPS_MULTIPLE_COMPUTE | Add echo 8 width to sum of multiple widths |
| CONTR_PIT_OVERLAPS_MULTIPLE_COMPUTE_DONE | Compute average multiple width from sum |
| CONTR_PIT_OVERLAPS_MULTIPLE_COMPUTE_DONE_REMARK | Remark echo 4 once width is summed |
| CONTR_PIT_OVERLAPS_MULTIPLE_COMPUTE_DONE_REMARK | Remark echo 6 once width is summed |
| CONTR_PIT_OVERLAPS_MULTIPLE_COMPUTE_DONE_REMARK | Remark echo 8 once width is summed |
| MULTI_LABEL_DONE | Mark the structure as labeled |
| ULTRA_COMPUTE_MULTIPLE_SEPARATION | Compute average multiple separation (1-8 diff.) |
| ULTRA_COMPUTE_REMAINING_WALL_THICKNESS | Compute remaining wall thickness based on separation |
| ECHOS_DOMINANT_OVERLAP_COMPUTE | Compute overlap condition for echos 1-3 |
| ECHOS_DOMINANT_OVERLAP_COMPUTE | Compute overlap condition for echos 1-2 |
| ECHOS_PIT_IN_MULTIPLE | Identify echo 2 as a pit echo |
| CONTR_PIT_IN_MULTIPLE_COMPUTE | Compute constraint on spurious echo height |
| ECHOS_PIT_IN_MULTIPLE_SPURIOUS | Identify echo 7 as a spurious echo |
| ECHOS_PIT_IN_MULTIPLE | Identify echo 3 as a pit echo |

TABLE 4-continued

| Rule Firings for Example Signal in FIG. 10. | |
|---|---|
| KS Rule Name | Function and echos involved |
| ECHOS_PIT_IN_MULTIPLE | Identify echo 5 as a pit echo |
| ECHOS_FIND_FRONT_DOMINANT | Identify echo 1 as the front-surface echo |
| CONTR_DONE_ALL_IDENTIFIED | Now all identified - set up to determine corrosion |
| ULTRA_PIT_DEPTH_IN_MULTIPLE | Calculate depth of pit for echo 5 - make a pit element |
| ULTRA_PIT_LOCATION | Assign location for pit from signal input data |
| ULTRA_PIT_AREA | Calculate the opening area and assign to pit element (5) |
| ULTRA_PIT_DEPTH_IN_MULTIPLE | Calculate depth of pit for echo 3 - make a pit element |
| ULTRA_PIT_DEPTH_IN_MULTIPLE | Calculate depth of pit for echo 2 - make a pit element |
| IDENTIFICATION COMPLETE - OUTPUT PIT ATTRIBUTES | |

The interpretation steps of the systems are best understood by looking at Table 4 and FIG. 21. Once the echo features are extracted and stored as working memory elements, rule activation starts with CONTR_DOM_COMPUTE. Since the example signal was recorded from a pipe area that was only about 50% corroded, multiples from the good pipe surfaces are present. The recursive looping of MULTI_DIFF and MULTI_FIND is used to identify a multiple structure consisting of echos 1-4-6-8. Echos 2, 3 and 5 are identified as echos from pit surfaces, and echo 7 as a spurious echo. Working memory elements for the pits are created, and the deepest of these (5) is sized and located. The deepest pit in a sensed area is of primary concern in a practical embodiment of the invention.

Echo 7 is identified as a spurious echo due to a low height compared to the pit echo heights. This echo was a reflection from a deep valley close to the edge of the sensed area for this signal. Since only a very small portion of this valley was intercepted by the ultrasonic wave, the echo height is small. Thus the interpretation as a spurious echo is appropriate. The sensed area for a later scan would be expected to detect this corrosion valley.

The actual example signal discussed here is representative of the majority of the signals which are produced by real corrosion pitting. The system according to a preferred embodiment of the invention has been tested on a wide variety of signals from both simulated and real pits, and the system's performance appears to be as good as manual interpretation by a human expert.

APPENDIX

The important operational rules of the preferred embodiment of the Expert System are described in this Appendix. Other rules, whose presence and implementation would be well known to those skilled in the art, are not described here. (Such rules include the housekeeping rules which clear or reset attributes before or after activation of the important operational rules. Also, means of inputting and outputting information, either textual or graphic, lies well within the ability of one of ordinary skill and will not be detailed here. Finally, the ability to gain information about the outer surface of the tubular may be gained using extensions of the descriptions contained in this Appendix and in the above Detailed Description section.)

Figure 16:
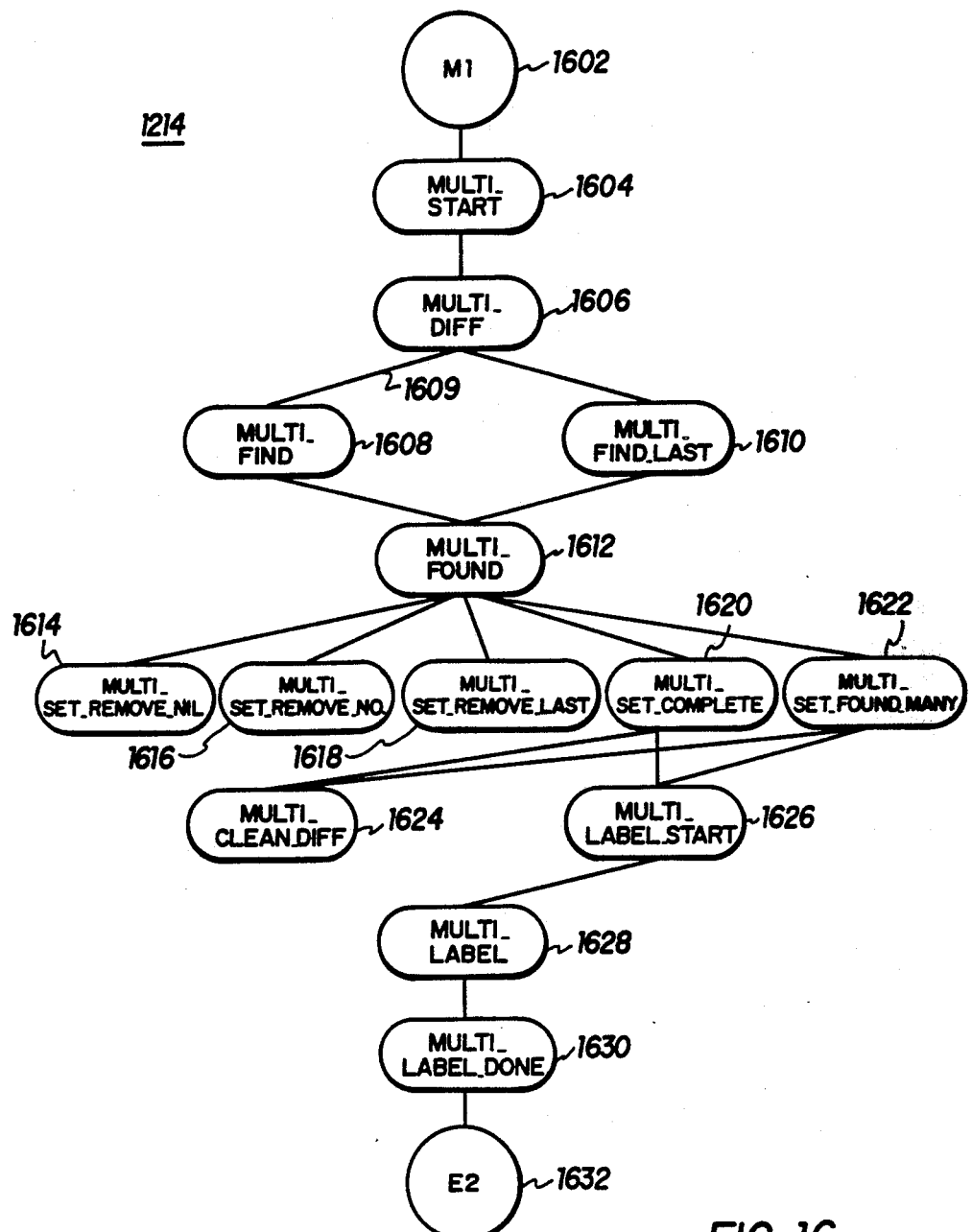
FIG. 16 is an activation diagram for the MULTIPLE knowledge source of FIG. 12.

RULES IN "MULTIPLE" KNOWLEDGE SOURCE (FIG. 16; the "MULTI_" prefix has been omitted for brevity.)

1604. START:

Begins search for a multiple structure within echos after a dominant echo. Sets the current possible multiple to the first un-marked echo after the dominant. Computes a location separation limit equal to the dominant-current echo separation which is used to test later echos for inclusion in multiple structure (DIFF and FIND). Marks the current echo. Creates a working memory element of class "structure", type "multiple" to denote a potential multiple structure defined by this separation limit.

1606. DIFF:

Computes the location difference between the current echo and each successive unidentified echo after the current echo. Location differences are computed sequentially, in order of recency in the working memory, until MULTI_FIND fires.

1608. FIND:

Tests an echo after the current for inclusion in multiple structure by computing the upper location difference with upper and lower location limits. If the location difference computed by DIFF falls within these limits (within a specified constraint defined by "constraint_on_location_for_multiple" (Table 3)), the echo is included in the structure. If several possible echos are within the constraint, the one having a location difference closest to the exact location (ultimately determined by START, above) is chosen. Sets the current echo to the new multiple echo and marks it. This rule forms a recursive structure 1609 with DIFF to search through all echos for a multiple structure associated with the dominant echo.

1610. FIND_LAST:

Completes the identification of multiple echos when there are no echos after the current echo to be considered. This rule looks at the last echo, whereas FIND looked at all but the last. This rule relaxes the condition, present in FIND, of having still another multiple structure echo after the current echo. This rule only looks "backward" to corroborate the last echo's inclusion in a multiple structure.

1612 FOUND:

Completes the search for a multiple structure. There are no unidentified echos between the dominant and first multiple which have not been considered for inclusion in some multiple structure. The number of multiple echos for the current structure must exceed an initial constraint "number_of_echos_for_multiples" (Table 3), which constraint is an integral number of echos, typically 2.

1614. SET_REMOVE_NIL:

Removes from working memory multiple structures which had been generated by START which have no identified multiple echos.

1616. SET_REMOVE_NUMBER:

If there are two or more multiple structures associated with a single leading echo (an impossible circumstance for an uncorroded outer tubular wall), this rule removes the one with fewer identified echos.

1618. SET_REMOVE_LAST:

If (1) there are two or more multiple structures associated with a single leading echo, and (2) these structures have the same number of multiples, remove from working memory the multiple structure with least location separation between the multiple echos.

1620. SET_COMPLETE:

Labels (i.e., changes the "type" attribute) the dominant echo as the leading echo when only one multiple structure for this dominant echo remains.

1622. SET_FOUND_MANY:

Completes the search for multiples and labels the leading echo as soon as the number of identified multiples echos exceeds a given constraint "number_of_echos_for_large_multiple_set" which is an integer number of echos, typically 4.

1624. CLEAN_DIFF:

Removes from working memory the location difference values computed by DIFF after the multiple structure is complete.

1626. LABEL_START:

Initiates the labeling of the identified multiple echos for subsequent rules.

1628. LABEL: Labels (i.e., defines the "type" attribute of) the identified multiple echos in a completed multiple structure.

1630. LABEL_DONE: Completes the labeling process (i.e., sets the "status" attribute to "labelled" in the appropriate working memory element of class "structure").

RULES IN CONTROL FUNCTION (FIGS. 15 and 18; the "C." prefix has been omitted for brevity)

1504. DOM_COMPUTE:

Initiates the search for a dominant echo by computing a constraint on the height of this echo. The constraint is the quotient of the height of the echo with the greatest height and an initial divisor constraint_on_value_dominant (typically 2.0).

1506. HEIGHT_COMPUTE_NO_MULTIPLES:

This rule calculates height values used to test for pit and spurious echos when no multiples are present. The values are the quotient of the maximum echo height and initial divisors. Typical multipliers for pit and spurious echos are 4.0 and 5.0, respectively (constraints "ratio_max/large_pit" and "ratio_max/spurious" in Table 3).

1508. DONE_ALL_IDENTIFIED:

This rule fires as soon as all echos have been identified (i.e., there are no unidentified echos). The ULTRASONICS KS's task of determining the corrosion from the identified echos is initiated.

1510. SET_FRONT_SURFACE_HEIGHT:

If the current signal is the first to be considered, the running average value for the height of the front surface echo is taken to be the value in constraint "default_front_surface_height". This value is obtained rom readings on signals previously determined to be from uncorroded pipe. The average front-surface height is used in the ULTRASONICS KS to estimate the pit opening area for pits in subsequent signals. This rule fires only once, to define the initial default value for the average front surface height.

1522. COMPUTE_AVERAGE_FRONT_SURFACE_HEIGHT:

The average front-surface echo height is updated when the current signal indicates that no corrosion is present. The difference between the current front-surface height and the average is computed and divided by the accumulated count on the number of updates. This quotient is then added to the past average to give the new average, and the update count is incremented by one.

1834. PIT_OVERLAPS_MULTIPLE_COMPUTE (FIG. 18):

If (1) no pit has been identified and (2) a multiple structure has been identified, then compute the sum of the widths of the multiples, and mark each multiple as the width is summed. This rule is preparatory for the following rule, 1842.

1842. PIT_OVERLAPS_MULTIPLE_COMPUTE_DONE (FIG. 18):

If the sum of the multiple widths has been computed, then compute a value to be used to test for a pit overlapping a multiple. The value is calculated by dividing the sum by the number of multiple echos, and multiplying by the constraint "constraint_on_overlap_-multiple" (typ. 1.6). The computed value is used by ECHOS: PIT_OVERLAPS_MULTIPLE (1848 in FIG. 18).

1844. PIT_OVERLAPS_MULTIPLE_COMPUTE_DONE_REMARK (FIG. 18):

Un-marks multiple echos (i.e., sets the "mark" working attribute of the echo element to "nil") once the sum of the multiple widths has been computed.

1838. PIT_IN_MULTIPLE_COMPUTE (FIG. 18):

If a multiple structure and pit echo have been found, compute a constraint ("spurious_height_in_multiple") on the height of a spurious echo within the structure. The constraint is computed as the quotient of the pit echo height and the constraint "height_ratio_pit/spurious" (typically 2).

RULES IN "Echos KNOWLEDGE SOURCE"

(FIGS. 17, 18, 19; the "E:" prefix has been omitted for brevity)

1708. FIRST

If an echo has the smallest location attribute value for any echos in the signal, then change the value of the "type" attribute to "first".

1706. FIND_DOMINANT:

If the height of an echo exceeds the current constraint on dominance (as computed by DOM_COMPUTE 1504), the echo is identified as both the dominant echo and the current echo. This rule initiates the search for multiples associated with the dominant echo.

1704. MAX_OVERLAP:

If both a maximum height echo and a neighboring echo exist with heights exceeding the current constraint on the dominant, prepare for testing of an overlap condition. Both upper and lower values are computed as follows. The upper value is the location of the maximum height echo plus the average of the echo widths. The lower value is the location of the maximum height echo minus the average of the echo widths. If the location of the lower height echo falls within these bounds, the echo is determined to overlap the first (maximum height) echo.

1712. WIDE_DOMINANT:

If a neighboring echo overlaps the maximum height echo, the neighboring echo is identified as a spurious echo and the maximum height echo is labeled the dominant. The neighboring echo must be less than some percentage of the maximum height echo ("constraint_on_leading_value" (Table 3), and is typically 80%) but greater than the constraint on dominant value ("constraint_on_value_dominant" from DOM_COMPUTE 1504). This rule initiates the search for multiples associated with the dominant echo.

1714. WIDE_DOMINANT_FIRST:

If (1) a neighboring echo overlaps the maximum height echo, and (2) the neighboring echo is greater than some multiple of the maximum height typ. 0.8, from "constraint_on_value_dominant" from DOM_COMPUTE 1504), then identify the neighboring echo as the dominant echo and label the maximum height echo spurious. This rule initiates the search for multiples associated with the dominant echo.

1812. LEADING_PIT_FRONT:

If (1) the remaining wall thickness calculated by COMPUTE_REMAINING_WALL_THICKNESS 1806 for a multiple structure is less than a constraint determined by "min_nominal_wall_thickness", typically 0.3 inches and (2) there are no echos except those associated with the multiple structure, then identify the leading echo as a pit surface. This is the rule analyzed in detail in the section entitled "Firing of Rules in the Knowledge Base".

1848. PIT_OVERLAPS_MULTIPLE:

This rule identifies a pit echo which occurs at a location so close to that of a multiple that no distinct pit echo is detected. If (1) there are no echos in the signal other than those already ascribed to a multiple structure, and (2) a multiple echo has a width which exceeds the value computed by CONTROL: PIT_OVERLAPS_MULTIPLE_COMPUTE_DONE 1842, then identify the multiple echo as a pit echo.

1816. DOMINANT_OVERLAP_COMPUTE:

When (1) a multiple structure and dominant echo exist and (2) an unidentified echo neighbors the dominant, then compute the overlap conditions for these echos (see MAX_OVERLAP 1704).

1836. OVERLAPS_DOMINANT:

If (1) an unidentified echo neighbors the dominant echo in a multiple structure, and (2) the neighboring echo overlaps the dominant (overlap conditions satisfied), then identify the neighboring echo as spurious.

1818. PIT_IN_MULTIPLE:

If (1) an echo exists within a multiple structure, and (2) it is the largest unidentified echo, then identify this echo as a pit echo (i.e., change its working memory element's "type" attribute to "pit").

1846. PIT_IN_MULTIPLE_SPURIOUS:

If (1) a pit echo and an unidentified echo exist within the same signal as a multiple structure, and (2) the height of the unidentified echo is less than the constraint "spurious_height_in_multiple", then identify the echo as spurious. The constraint is typically set to 0.2 times the height of the largest echo for the signal (see CONTROL: PIT_IN_MULTIPLE_COMPUTE 1838).

1822. FRONT_PRECEDES_DOMINANT:

When (1) the first echo of a signal is located before the leading echo of a multiple structure and (2) this first echo is of lower height than the leading echo, then identify the echo as the front-surface echo. However, the rule FIRST_IS_SPURIOUS_COMPUTE (1826, described below) has the "higher priority" then this rule (fires first if the conditions of both rules are satisfied).

1826. FIRST_IS_SPURIOUS_COMPUTE:

When the first echo is located before the leading echo of a multiple structure, compute a location constraint for the echo to be identified as spurious. The constraint value is calculated as:

$$\frac{2 * (\text{nominal wall thickness} - \text{remaining wall thickness}) * (\text{samples/second})}{(\text{speed of sound in liquid})}$$

This constraint value is the location difference between (1) a possible front-surface echo and (2) the leading echo calculated on the basis of the measured remaining wall thickness. The nominal wall thickness, samples/second, and speed of sound in liquid are preprogrammed, as described in the discussion related to Table 3. The remaining wall thickness is calculated by U_COMPUTE_REMAINING_WALL_THICKNESS 1806.

1840. FIRST_IS_SPURIOUS:

If the separation between the first echo and the leading echo exceeds the constraint calculated in FIRST_IS_SPURIOUS_COMPUTE (1826, above), then the first echo cannot be a front-surface echo. (If it were from the front surface, then the leading echo would have to have come from a surface beyond the pipe outer wall, which is impossible.) The first echo is identified as spurious and the leading echo is marked as the front surface echo.

1828. FIND_FRONT_DOMINANT:

If there are (1) no unidentified echos and (2) no echos before the leading echo of a multiple structure, then identify the leading echo as the front-surface echo.

1830. FIND_FRONT_SPURIOUS:

If (1) there are no unidentified echos and (2) there is a single spurious echo before the leading, then identify this echo as the front-surface echo and generate a structure "spurious_as_front_surface." The rule FIRST_IS_SPURIOUS_COMPUTE 1826 has higher priority.

1904. FRONT_NOT_MAX_NO_MULTIPLES: (No Multiple Structure)

If (1) there is an echo before the echo with maximum height with a height which exceeds the constraint in pit height computed in HEIGHT_COMPUTE_NO_MULTIPLES (1506, FIG. 15), and (2) there are no echos before this echo with heights greater than the constraint "spurious_height_no_multiples" (from HEIGHT_COMPUTE_NO_MULTIPLES 1506), then identify the echo as the front-surface echo.

1906. FRONT_MAX_FIRST_NO_MULTIPLES: (No Multiple Structure)

If there are no echos before the echo with maximum height which have heights greater than the constraint "spurious_height_no_multiples" (from HEIGHT_COMPUTE_NO_MULTIPLES 1506), then identify the maximum height echo as the front-surface echo.

1908. FRONT_NOT_MAX_FIRST_NO_MULTIPLES: (No Multiple Structure)

If there is an echo before the echo with maximum height which has a height greater than the constraint "spurious_height_no_multiples" (from HEIGHT_COMPUTE_NO_MULTIPLES 1506), then identify this echo as the front surface echo.

1914. FRONT_SURFACE_OVERLAP_COMPUTE:

If (1) a front-surface echo (or spurious echo after the front-surface) have been found, and (2) there is an echo which precedes or is after this echo, then compute the location for echo overlap with the front-surface or spurious echo (see MAX_OVERLAP 1704).

1916. FRONT_SURFACE_OVERLAP:

If (1) a front-surface echo has been identified and (2) there is an echo which precedes the front-surface or is after the front-surface and (3) its location is within the limits for overlap with the front-surface, then (1) mark the echo as a spurious echo and (2) add a working memory element of class "structure" with type "wide_front_surface." The limits for overlap are computed by FRONT_SURFACE_OVERLAP_COMPUTE 1914.

1918. FRONT_SURFACE_OVERLAP_SPURIOUS:

If (1) there is an overlap between a front-surface echo and following spurious echo and (2) there is an echo which follows the spurious and overlaps it, then mark the echo as a spurious echo and (add a working memory element of class "structure") and type "wide_front_surface." Note this rule forms a recursive structure 1920 with FRONT_SURFACE_OVERLAP_COMPUTE.

1922. FRONT_MAX_PIT_NO_MULTIPLES: (No Multiple Structure)

If (1) a front-surface echo has been identified, (2) no structure has been found other than "wide_front-surface," (3) an echo of height greater than the constraint "pit_height_no_multiples" occurs after the front surface echo (CONTROL: HEIGHT_COMPUTE_NO_MULTIPLES 1506) and (4) there are no unidentified echos with greater height than this echo, then identify the echo as a pit echo and generate a structure (i.e., add a working memory element of class "structure") "large_pit_after_front_surface_no_multiples".

1924. FRONT_NEW_PIT_NO_MULTIPLES: (No Multiple Structure)

If (1) a structure, "large_pit_after_front_surface_no_multiples" (from 1922) has been identified and (2) there is an echo after the front surface with a height *greater* than the constraint "spurious_height_no_multiples" (from HEIGHT_COMPUTE_NO_MULTIPLES 1506), then identify this as a "pit echo".

1928. FRONT_PIT_SPURIOUS_NO_MULTIPLES: (No Multiple Structure)

If (1) a structure, "large_pit_after_front_surface_no_multiples" has been identified (in 1922) and (2) there is an echo after the front_surface with a height less than the constraint "spurious_height_no_multiples," then identify these this as a spurious echo.

RULES IN "ULTRASONICS KNOWLEDGE SOURCE"

(FIGS. 18 and 20; the "U:" prefix is omitted for brevity)

For the following rules, the depth of the pitted surface giving rise to an identified pit echo is determined as:

$$\frac{((\text{pit echo location in samples}) - (\text{front-surface echo location}))}{(2.0 * (\text{samples/second}) / (\text{speed of sound in liquid}))} \quad [A1]$$

The factor of two accounts for the "round-trip" path taken by the signal as it travels between the front-surface and the pit bottom through the liquid.

The pit opening area is calculated as follows:

$$(1.0 - ((\text{front-surface height})/(\text{average f-s height})))*(\text{spot-area}) \quad [A2]$$

1804. COMPUTE_MULTIPLE_SEPARATION:

This rule computes the average location separation between echos in a multiple structure once a multiple structure has been found. The separation is computed as the difference between the last multiple echo and the leading echo of the multiple structure, divided by the total number of multiples.

1806. COMPUTE_REMAINING_WALL_THICKNESS:

Once the multiple structure's echo separation has been computed (1804), the remaining wall thickness can be calculated based on the multiple structure. If the average multiple separation is given in terms of the number of equal-spaced time samples, the remaining wall thickness can be calculated as:

$$\frac{(\text{average separation in samples}) * (\text{speed of sound in pipe material})}{(2.0 * (\text{number of time samples per second}))}$$

The factor of 2.0 in the denominator corrects for the fact that the signal passes through the pipe wall twice for each multiple reflection.

2006. SMALL_PIT_OVERLAPS_MULTIPLE:

If both a multiple structure and a structure "pit_overlaps_multiple" have been found, then use formula A1, above, to determine the depth of the pit from the location difference between the front surface and the overlapped multiple. Create a working memory element of class "pit" with this calculated depth inserted into the "depth" attribute (i.e., store the depth as a new pit attribute).

2010. PIT_DEPTH_IN_MULTIPLE:

If a pit echo has been identified within a multiple structure which does not overlap an echo in the multiple structure, then determine the depth of pit from location difference between the front-surface and pit echo. Create a working memory element of class "pit" with this calculated depth inserted into the "depth" attribute (i.e., store the depth as a new pit attribute).

2016. PIT_DEPTH_LARGE_PIT:

If a structure "large_pit_after_front_surface" or "large_pit_after_front_surface_no_multiples" has been found, then determine the depth of pit from the location difference between the front surface echo and pit echo. Create a working memory element of class "pit" with this calculated depth inserted into the "depth" attribute (i.e., store the depth as a new pit attribute).

2020. PIT_IS_FRONT_SURFACE:

If a structure "pit_dominant_as_front_surface" has been found, then compute the depth of the large pit as the difference between the nominal pipe wall thickness and the measured remaining wall thickness. In addition mark the pit as type "front_surface." Create a working memory element of class "pit" with this calculated depth inserted into the "depth" attribute (i.e., store the depth as a new pit attribute).

2024. MULTIPLE_NO_CORROSION:

If (1) a multiple structure has been found and (2) there are no identified pits and (3) the remaining wall thickness is greater than the nominal wall thickness, then conclude that there is no corrosion, and create a new working memory element of class "corrosion" and attribute "no__corrosion".

2028. PIT__LOCATION:

If (1) a pit has been found and (2) it is the deepest for the signal, then store the location of the center of the sensor spot-area as a pit attribute. (The sensor spot center is obtained when the signal data is read into the program at 1202 (FIG. 12).

2038. PIT__AREA:

If (1) a pit has been found and (2) it is the deepest for the signal then compute the opening area of the pit as a fraction of the sensor spot-area according to the formula given above. Store the opening area as a pit attribute.

2034. PIT__AREA__SPLIT__LEADING:

If (1) a pit has been found and (2) it is the deepest for the signal and (3) the front-surface echo overlaps the leading echo (a working memory element of structure "spurious__as__front__surface" has been previously identified), then add the heights of the spurious echo to the front-surface height before computing the opening area of the pit. Store the opening area as a pit attribute.

2042. PIT__AREA__NO__FRONT:

If a pit of type "front-surface" has been found, then set the opening area to 100% of the spot area. Store the opening area as a pit attribute.

CONCLUSION

While various features of particular embodiments according to the present invention have been presented above, it is to be understood that they have been presented by way of example, and not limitation. Thus, the breadth and scope of the invention are to be defined not by the above exemplary embodiments, but only in accordance with the following claims and their equivalents.

What I claim is:

1. A method for preprocessing and transmitting echo waveform information derived from an echo of an acoustic wave reflected from a target surface, comprising the steps of:
    digitizing an echo waveform produced in response to a launching of an acoustic wave;
    detecting amplitude of said echo waveform;
    continuously storing said digitized echo waveform in a recirculating memory;
    freezing information stored in said recirculating memory during a predetermined time period beginning after the detected amplitude of said echo waveform rises above a predetermined threshold;
    measuring a time interval between said launching of the acoustic wave and the rise of said detected amplitude of said echo waveform above said predetermined threshold; and
    multiplexing the time interval measured in said measured step and the waveform information frozen in said recalculating memory in said freezing step for transmission to a location remote from said acoustic wave.

2. A method for preprocessing and transmitting echo waveform information derived from the echo of an acoustic wave reflected from a target surface, comprising the steps of:
    converting an echo waveform produced in response to a launching of an acoustic wave to a monopolar waveform;
    smoothing said monopolar waveform, whereby a smoothed monopolar waveform is formed;
    compressing the dynamic range of the magnitude of said smoothed monopolar waveform, whereby a compressed, smoothed monopolar waveform is formed;
    digitizing said compressed, smoothed, monopolar waveform, whereby a digitized waveform is formed;
    storing said digitized waveform in a recirculating memory for transmission to a location remote from said acoustic wave; and
    freezing after a predetermined time period, information stored in said recirculating memory, said predetermined time period beginning when the amplitude of said monopolar waveform, after said launching of said acoustic wave, exceeds a predetermined threshold.

3. The method of claim 1 including, before digitizing said echo waveform, sensing the magnitude of said waveform, determining the gain required to adjust said magnitude to a desired range, amplifying said waveform by the determined gain and digitizing the determined gain value.

4. The method of claim 3 including multiplexing said digitized, determined gain value with said time interval and said stored waveform.

5. The method of claim 3 including, after amplifying said waveform by said determined gain, but before digitizing said waveform, logarithmically amplifying said waveform, whereby the dynamic amplitude range of different waveforms digitized is compressed.

6. The method of claim 3 including, before digitizing said waveform, reducing the bandwidth of said amplified waveform by passing it through an envelope detector.

7. The method of claim 6 including, before digitizing said waveform, further reducing the bandwidth of said amplified and envelope-detected waveform by rectifying said envelope-detected waveform and filtering it through a low-pass frequency filter.

8. The method of claim 1 including, before digitizing said waveform, logarithmically amplifying said waveform, whereby the dynamic amplitude range of different waveforms is compressed.

9. The method of claim 1 including resetting said recirculating memory, after said multiplexing step, for continuously storing incoming waveform information.

10. A method for preprocessing and transmitting echo waveform information derived from the echo of an acoustic wave reflected from a target surface, comprising the steps of:
    digitizing a full echo waveform produced in response to a launching of the acoustic wave, whereby digital waveform data is formed;
    detecting amplitude of said full echo waveform;
    continuously storing said digital waveform data in a recirculating memory for transmission to a location remote from said acoustic wave; and
    halting said continuously storing step after a predetermined time period beginning when the amplitude of said monopolar waveform, after said launching of said acoustic wave, exceeds a predetermined threshold, whereby a digital representation of said full echo waveform is frozen in said recirculating memory.

11. The method of claim 2 including, before said converting step, measuring the magnitude of said wave form, determining the gain required to adjust said magnitude to a desired range and amplifying said waveform by the determined gain.

12. The method of claim 2 including converting said echo waveform to a monopolar waveform by passing it through an envelope detector.

13. The method of claim 2 including smoothing said monopolar waveform by rectifying it and filtering said rectified waveform through a low-pass frequency filter.

14. The method of claim 2 including compressing the dynamic range of said smoothed, monopolar wave form by logarithmically amplifying it.

* * * * *

UNITED STATES PATENT AND TRADEMARK OFFICE
CERTIFICATE OF CORRECTION

PATENT NO. : 4,893,286

DATED : January 9, 1990

INVENTOR(S) : Wesley N. Cobb

It is certified that error appears in the above-identified patent and that said Letters Patent is hereby corrected as shown below:

Column 59, lines 60 and 61: "measured" should read --measuring--;
Column 59, line 62: "recalculating" should read --recirculating--.

Signed and Sealed this

Seventeenth Day of December, 1991

Attest:

HARRY F. MANBECK, JR.

*Attesting Officer*     *Commissioner of Patents and Trademarks*